(12) United States Patent
Bull et al.

(10) Patent No.: US 8,329,729 B2
(45) Date of Patent: Dec. 11, 2012

(54) QUINUCLIDINE DERIVATIVES AS MUSCARINIC M3 RECEPTOR ANTAGONISTS

(75) Inventors: Richard James Bull, Harlow (GB); Rhonan Lee Ford, Loughborough (GB); Antonio Mete, Loughborough (GB)

(73) Assignees: Astrazeneca AB, Sodertalje (SE); Pulmagen Therapeutics Synergy Ltd., Fulmer, Slough (GB)

(*) Notice: Subject to any disclaimer, the term of this patent is extended or adjusted under 35 U.S.C. 154(b) by 10 days.

(21) Appl. No.: 12/992,045

(22) PCT Filed: May 13, 2008

(86) PCT No.: PCT/GB2008/001647
§ 371 (c)(1),
(2), (4) Date: Mar. 7, 2011

(87) PCT Pub. No.: WO2009/138707
PCT Pub. Date: Nov. 19, 2009

(65) Prior Publication Data
US 2011/0172237 A1    Jul. 14, 2011

(51) Int. Cl.
*A61K 31/44* (2006.01)
(52) U.S. Cl. .............. 514/305; 546/137; 546/304
(58) Field of Classification Search ............... 514/305; 546/137, 304
See application file for complete search history.

(56) References Cited

U.S. PATENT DOCUMENTS

| | | | |
|---|---|---|---|
| 2,404,588 | A | 7/1946 | Martin et al. |
| 4,579,854 | A | 4/1986 | Iwakuma et al. |
| 5,482,934 | A | 1/1996 | Calatayud et al. |
| 2002/0169208 | A1 | 11/2002 | Druzgala |
| 2002/0173536 | A1 | 11/2002 | Noe et al. |
| 2005/0222144 | A1 | 10/2005 | Konetzki et al. |
| 2010/0029713 | A1 | 2/2010 | Ford et al. |

FOREIGN PATENT DOCUMENTS

| | | |
|---|---|---|
| DE | 2104179 C3 | 10/1980 |
| DE | 4129535 A1 | 3/1992 |
| DE | 10216333 A1 | 10/2003 |
| EP | 1785421 A1 | 5/2007 |
| EP | 1894568 A1 | 3/2008 |
| FR | 2123519 A1 | 9/1972 |
| FR | 2155927 A1 | 5/1973 |
| FR | 2168881 A1 | 9/1973 |
| FR | 2208649 A1 | 6/1974 |
| GB | 1320069 A | 6/1973 |
| WO | WO-92/05147 A1 | 4/1992 |
| WO | WO-98/04517 A1 | 2/1998 |
| WO | WO-98/21183 | 5/1998 |
| WO | WO-01/04118 | 1/2001 |
| WO | WO-02/00679 A2 | 1/2002 |
| WO | WO-02/053564 A2 | 7/2002 |
| WO | WO-02/076933 A1 | 10/2002 |
| WO | WO-02/088167 A1 | 11/2002 |
| WO | WO-02/096855 A2 | 12/2002 |
| WO | WO-03/042164 A1 | 5/2003 |
| WO | WO-03/087094 A2 | 10/2003 |
| WO | WO-2004/032921 A1 | 4/2004 |
| WO | WO-2004/096800 A2 | 11/2004 |
| WO | WO-2005/000815 A2 | 1/2005 |
| WO | WO-2005/025555 A2 | 3/2005 |
| WO | WO-2005/041980 A1 | 5/2005 |
| WO | WO-2006/035303 A1 | 4/2006 |
| WO | WO-2006/046916 A1 | 5/2006 |
| WO | WO-2006/048225 A1 | 5/2006 |
| WO | WO-2006/066928 A1 | 6/2006 |
| WO | WO-2006/112778 A1 | 10/2006 |
| WO | WO-2007/015664 A1 | 2/2007 |
| WO | WO-2007/015667 A1 | 2/2007 |
| WO | WO-2007/017669 A1 | 2/2007 |
| WO | WO-2007/017670 A1 | 2/2007 |
| WO | WO-2007/018461 A1 | 2/2007 |
| WO | WO-2007/027134 A1 | 3/2007 |
| WO | WO-2007/068929 A1 | 6/2007 |
| WO | WO-2007/123465 A1 | 11/2007 |
| WO | WO-2008/010765 A1 | 1/2008 |
| WO | WO-2008/017824 A1 | 2/2008 |
| WO | WO-2008/017827 A2 | 2/2008 |
| WO | WO-2008/023157 A1 | 2/2008 |
| WO | WO-2008/059239 A1 | 5/2008 |
| WO | WO-2008/059245 A1 | 5/2008 |
| WO | WO-2008/075005 A1 | 6/2008 |

(Continued)

OTHER PUBLICATIONS

Jordan, V. C. Nature Reviews: Drug Discovery, 2, 2003, 205.*
Hackam, et al. JAMA, 296(14), 2006, 1731-1732.*
Cazzola, M., et al., "Ultra long-acting β2-agonists in development for asthma and chronic obstructive pulmonary disease," *Expert Opin. Investig. Drugs* (2005), vol. 14, No. 7, pp. 775-783.
Lee, A.M., et al., "Selective muscarinic receptor antagonists for airway diseases," *Current Opinion in Pharmacology* (2001), vol. 1, pp. 223-229.
Stubbins, J.F., et al., "Muscarinic $M_1$ and $M_2$ binding affinity of cyclic amine derivatives of caramiphen and dicyclomine," *Med Chem Res* (1992), vol. 2, pp. 384-393.
"8,8-Dimethyl-3α-isovaleryloxy-6β-(1-phenylcyclopentylcarbonyloxy)-8-azoniabicyclo[3.2.1]octan", XP-002469597, Beilstein Registry No. 1558578, Boll. Chim. Farm. (1964), vol. 103, pp. 576-582, abstract.
Mikhlina, E.E., et al., "Synthesis and cholinolytic properties of esters of 3-hydroxyquinuclidine," *Pharmaceutical Chemistry Journal* (1981), vol. 15, No. 8, pp. 569-572, example IX.
International Search Report of PCT/GB2008/001647, mailed Mar. 9, 2009.

(Continued)

*Primary Examiner* — Douglas M Willis
(74) *Attorney, Agent, or Firm* — Astrazeneca AB

(57) ABSTRACT

The invention provides named compounds of formula (I), wherein R4 is a N-substituted quinuclidine (I) pharmaceutical compositions containing them and a process for preparing the pharmaceutical compositions. Their use in therapy for the treatment of conditions mediated by M3 muscarinic receptors, such as chronic obstructive pulmonary disease is also disclosed.

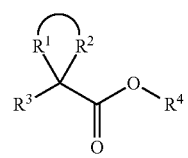

(I)

7 Claims, 1 Drawing Sheet

FOREIGN PATENT DOCUMENTS

Figure 1:
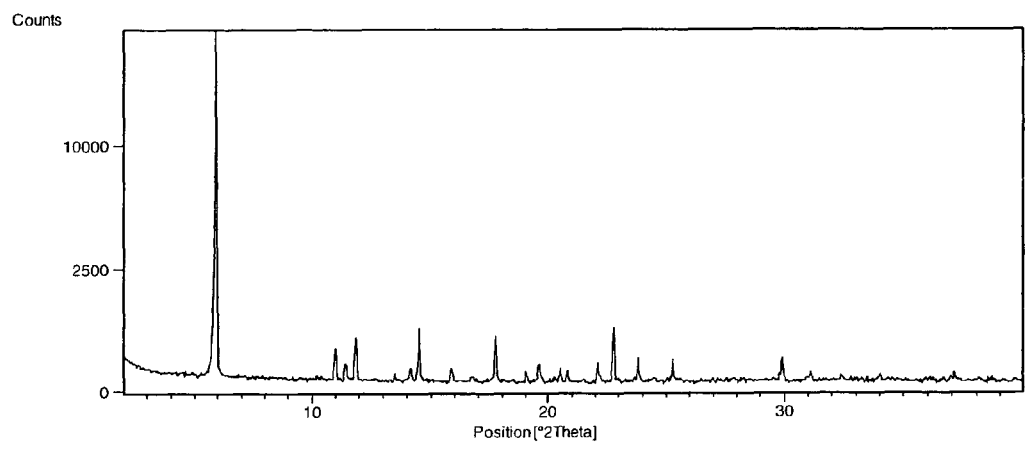

| | | |
|---|---|---|
| WO | WO-2008/075006 A1 | 6/2008 |
| WO | WO-2008/075026 A1 | 6/2008 |
| WO | WO-2008/096093 A1 | 8/2008 |
| WO | WO-2008/096094 A1 | 8/2008 |
| WO | WO-2008/096111 A1 | 8/2008 |
| WO | WO-2008/096121 A1 | 8/2008 |
| WO | WO-2008/096126 A1 | 8/2008 |
| WO | WO-2008/096127 A2 | 8/2008 |
| WO | WO-2008/096128 A1 | 8/2008 |
| WO | WO-2008/096129 A1 | 8/2008 |
| WO | WO-2008/096136 A1 | 8/2008 |
| WO | WO-2008/096143 A1 | 8/2008 |
| WO | WO-2008/096149 A2 | 8/2008 |
| WO | WO-2008/099186 A1 | 8/2008 |
| WO | WO-2008/104790 A1 | 9/2008 |
| WO | WO-2008/149053 A1 | 12/2008 |
| WO | WO-2008/149110 A1 | 12/2008 |
| WO | WO-2009/098448 A1 | 8/2009 |
| WO | WO-2009/098453 A1 | 8/2009 |
| WO | WO-2009/098455 A1 | 8/2009 |
| WO | WO-2009/138707 A1 | 11/2009 |
| WO | WO-2009/139707 A1 | 11/2009 |
| WO | WO-2009/139708 A1 | 11/2009 |
| WO | WO-2009/139709 A1 | 11/2009 |
| WO | WO-2009/139710 A1 | 11/2009 |
| WO | WO-2009/153536 A1 | 12/2009 |
| WO | WO-2009/154554 A1 | 12/2009 |
| WO | WO-2009/154555 A1 | 12/2009 |
| WO | WO-2010/015792 A1 | 2/2010 |
| WO | WO-2010/018352 A1 | 2/2010 |
| WO | WO-2010/019097 A1 | 2/2010 |
| WO | WO-2010/019098 A1 | 2/2010 |
| WO | WO-2010/019099 A1 | 2/2010 |

OTHER PUBLICATIONS

Casarosa et al.; The Constitutive Activity of the Human Muscarinic M3 Receptor Unmasks Differences in the Pharmacology of Anticholinergics. The Journal of Pharmacology and Experimental Therapeutics; 2010; pp. 201-209; vol. 333, No. 1.

Navratil et al; Solvent Extraction of some Incapacitating Agents; Journal of Radioanalytical and Nuclear Chemistry; 2004; pp. 429-432; vol. 262, No. 2.

* cited by examiner

QUINUCLIDINE DERIVATIVES AS MUSCARINIC M3 RECEPTOR ANTAGONISTS

CROSS-REFERENCE TO RELATED APPLICATIONS

This application is the U.S. National Stage under 35 U.S.C. §371 of International Application No. PCT/GB2008/001647, filed May 13, 2008 and is incorporated herein by reference in its entirety.

NEW COMPOUNDS 273

The present invention relates to cycloalkyl-substituted alkyl esters of polycyclic amino alcohols, a process for their preparation, pharmaceutical compositions containing them, a process for preparing pharmaceutical compositions, their use in therapy and intermediates of use in their preparation.

BACKGROUND TO THE INVENTION

Muscarinic receptors are a G-protein coupled receptor (GPCR) family having five family members $M_1$, $M_2$, $M_3$, $M_4$ and $M_5$. Of the five muscarinic subtypes, three ($M_1$, $M_2$ and $M_3$) are known to exert physiological effects on human lung tissue.

Parasympathetic nerves are the main pathway for reflex bronchoconstriction in human airways and mediate airway tone by releasing acetylcholine onto muscarinic receptors Airway tone is increased in patients with respiratory disorders such as asthma and chronic obstructive pulmonary disease (COPD), and for this reason muscarinic receptor antagonists have been developed for use in treating airway diseases. Muscarinic receptor antagonists often called anticholinergics in clinical practice, have gained widespread acceptance as a first-line therapy for individuals with COPD, and their use has been extensivley reviewed in the literature (e.g. Lee et al, Current Opinion in Pharmacology 2001, 1, 223-229).

When used to treat respiratory disorders, muscarinic receptor antagonists are typically administered by inhalation. However, when administered by inhalation a significant proportion of the muscarinic receptor antagonist is often absorbed into the systemic circulation resulting in reported side effects such as dry mouth. Additionally, the majority of muscarinic antagonists have a relatively short duration of action requiring that they be administered several times a day. Such a multiple-daily dosing regime is not only inconvenient to the patient but also creates a significant risk of inadequate treatment due to patient non-compliance associated with the frequent repeat dosing schedule.

There therefore remains a need for novel compounds that are capable of blocking muscarinic receptors. In particular, a need exists for new muscarinic antagonists that have high potency and reduced systemic side effects when administered by inhalation. Moreover, a need exists for new muscarinic antagonists that exhibit a long duration of action when dosed by inhalation, and which are amenable to either once or twice daily dosing.

WO 98/04517 describes arylcyclopropane, arylcyclobutane, arylcyclopentane and arylcyclohexane carboxylic esters having antimuscarinic activity on the urinary bladder smooth muscle.

Our co-pending application PCT/GB2007/004350 relates to compounds of formula (I)

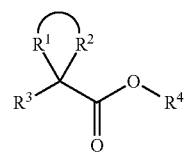

wherein $R^1$ and $R^2$ together with the carbon atom to which they are both directly attached form a 7 membered aliphatic carbocyclic ring which may be optionally substituted by one or more substituents independently selected from halogen, hydroxyl, $C_{1-6}$ alkoxy, $NH_2$, $NH(C_{1-6}$ alkyl), $N(C_{1-6}$ alkyl)$_2$ and $C_{1-6}$ alkyl which $C_{1-6}$ alkyl may be optionally substituted by one or more substituents independently selected from halogen and hydroxyl;

$R^3$ represents phenyl or a 5 to 6 membered heteroaryl ring, each of which may be optionally substituted by one or more substituents independently selected from halogen cyano, nitro, SH, $S(O)_{0-2}R^9$, $NR^{10}R^{11}$, $S(O)_2NR^{12}R^{13}$, $C(O)NR^{14}R^{15}$, $C(O)_2R^{16}$, $NR^{17}S(O)_2R^{18}$, $NR^{19}C(O)R^{20}$, $NR^{21}C(O)_2R^{22}$, $NR^{23}C(O)NR^{24}R^{25}$, $OR^{26}$ and $C_{1-6}$ alkyl which $C_{1-6}$ alkyl may be optionally substituted by one or more substituents independently selected from halogen, hydroxyl, $C_{1-6}$ alkoxy, $NH_2$, $NH(C_{1-6}$ alkyl) and $N(C_{1-6}$ alkyl)$_2$;

$R^4$ represents a group of formula (II) or (IIIa) or (IIIb);

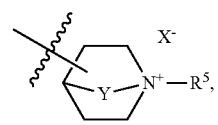

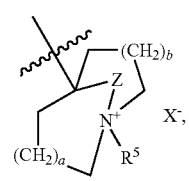

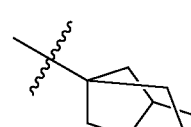

wherein

Y is —$CH_2$—, —$CH_2CH_2$— or —$CH_2CH_2CH_2$— and the substitution on the ring in group (II) may be in the 3 or 4 positions;

a is 1 or 2;

b is 1 or 2;

Z is —$CH_2$—;

$R^5$ represents a group of formula (IV)

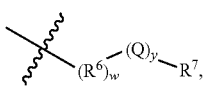

(IV)

wherein
w is 0 or 1;
$R^6$ represents $C_{1-4}$ alkylene optionally substituted by one or more substituents independently selected from halogen, hydroxyl, $C_{1-6}$ alkoxy, $NH_2$, $NH(C_{1-6}$ alkyl) and $N(C_{1-6}$ alkyl$)_2$;
when w is 0, y is 0; when w is 1, y is 0 or 1;
Q represents O, $S(O)_{0-2}$, $NR^8$, —$CONR^8$—, —$SO_2NR^8$—, —$NR^8CO$—, —$NR^8SO_2$—, —$OC(O)$—, —$C(O)O$—, —HC=CH— or ethynylene;
$R^7$ represents a cyclic group $Cyc^1$ or a $C_{1-4}$ alkyl group which $C_{1-4}$ alkyl group may be optionally substituted by one or more substituents independently selected from halogen, hydroxyl, $C_{1-4}$ alkoxy, $NH_2$, $NH(C_{1-4}$ alkyl), $N(C_{1-4}$ alkyl$)_2$, a cyclic group $Cyc^2$ and —$OCyc^2$; and $R^7$ may additionally represent hydrogen when Q represents O, $NR^8$, —$CONR^8$—, —$SO_2NR^8$—, —$C(O)O$—, —HC=CH— or ethynylene;
$Cyc^1$ and $Cyc^2$ each independently represent aryl, heteroaryl, a 3 to 8 membered aliphatic carbocyclic ring or a 4 to 8 membered aliphatic heterocyclic ring, each of which may be optionally substituted by one or more substituents independently selected from halogen, cyano, nitro, SH, $S(O)_{0-2}R^9$, $NR^{10}R^{11}$, $S(O)_2NR^{12}R^{13}$, $C(O)NR^{14}R^{15}$, $C(O)_2R^{16}$, $NR^{17}S(O)_2R^{18}$, $NR^{19}C(O)R^{20}$, $NR^{21}C(O)_2R^{22}$, $NR^{23}C(O)NR^{24}R^{25}$, $OR^{26}$, phenyl and $C_{1-6}$ alkyl which phenyl or $C_{1-6}$ alkyl may be optionally substituted by one or more substituents independently selected from halogen, hydroxyl, $C_{1-6}$ alkoxy, $NH_2$, $NH(C_{1-6}$ alkyl) and $N(C_{1-6}$ alkyl$)_2$;
$R^8$ represents hydrogen or $C_{1-6}$ alkyl;
$R^9$ and $R^{18}$ each independently represent $C_{1-6}$ alkyl, which $C_{1-6}$ alkyl may be optionally substituted by one or more substituents independently selected from halogen, hydroxyl, $C_{1-6}$ alkoxy, $NH_2$, $NH(C_{1-6}$ alkyl) and $N(C_{1-6}$ alkyl$)_2$; and
$R^{10}$, $R^{11}$, $R^{12}$, $R^{13}$, $R^{14}$, $R^{15}$, $R^{16}$, $R^{17}$, $R^{19}$, $R^{20}$, $R^{21}$, $R^{22}$, $R^{23}$, $R^{24}$, $R^{25}$ and $R^{26}$ each independently represent hydrogen or $C_{1-6}$ alkyl, which $C_{1-6}$ alkyl may be optionally substituted by one or more substituents independently selected from halogen, hydroxyl, $C_{1-6}$ alkoxy, $NH_2$, $NH(C_{1-6}$ alkyl) and $N(C_{1-6}$ alkyl$)_2$; or any of $R^{10}$ and $R^{11}$, $R^{12}$ and $R^{13}$, $R^{14}$ and $R^{15}$ or $R^{24}$ and $R^{25}$, together with the nitrogen atom to which they are both attached, may form a 4 to 8 membered aliphatic heterocyclic ring, which heterocyclic ring may be optionally substituted by one or more substituents independently selected from halogen, hydroxyl and $C_{1-6}$ alkyl, which $C_{1-6}$ alkyl may be optionally substituted by one or more substituents independently selected from halogen and hydroxyl;
and X represents a pharmaceutically acceptable anion of a mono or polyvalent acid.

SUMMARY OF THE INVENTION

The present invention provides compounds falling within the scope of, but not specifically disclosed in, our co-pending application PCT/GB2007/004350 referred to above.

Thus, the present invention provides a compound which has a quaternary ammonium species selected from the group consisting of:
(R)-1-[(6-Methyl-pyridin-3-ylcarbamoyl)-methyl]-3-(1-phenyl-cycloheptanecarbonyloxy)-1-azonia-bicyclo [2.2.2]octane X;
(R)-1-[(6-Methyl-pyrazin-2-ylcarbamoyl)-methyl]-3-(1-phenyl-cycloheptanecarbonyloxy)-1-azonia-bicyclo [2.2.2]octane X;
(R)-3-(1-Phenyl-cycloheptanecarbonyloxy)-1-[(6-trifluoromethyl-pyridazin-3-ylcarbamoyl)-methy;]-1-azonia-bicyclo[2.2.2]octane X;
(R)-1-(Benzo[d]isoxazol-3-ylcarbamoylmethyl)-3-(1-phenyl-cycloheptanecarbonyloxy)-1-azonia-bicyclo[2.2.2] octane X;
(R)-1-(Pyridazin-3-ylcarbamoylmethyl)-3-(1-thiophen-2-yl-cycloheptanecarbonyloxy)-1-azonia-bicyclo[2.2.2]octane X;
(R)-1-[(5-Methyl-isoxazol-3-ylcarbamoyl)-methyl]-3-(1-thiophen-2-yl-cycloheptanecarbonyloxy)-1-azonia-bicyclo[2.2.2]octane X;
(R)-1-[(3-Methyl-isoxazol-5-ylcarbamoyl)-methyl]-3-(1-thiophen-2-yl-cycloheptanecarbonyloxy)-1-azonia-bicyclo[2.2.2]octane X;
(R)-1-[(3-Fluoro-phenylcarbamoyl)-methyl]-3-(1-thiophen-2-yl-cycloheptanecarbonyloxy)-1-azonia-bicyclo[2.2.2] octane X;
(R)-1-[(5-Methyl-pyrazin-2-ylcarbamoyl)-methyl]-3-(1-thiophen-2-yl-cycloheptanecarbonyloxy)-1-azonia-bicyclo[2.2.2]octane X;
(R)-1-(Benzo[d] isoxazol-3-ylcarbamoylmethyl)-3-(1-thiophen-2-yl-cycloheptanecarbonyloxy)-1-azonia-bicyclo[2.2.2]octane X;
(R)-1-(Pyrazin-2-ylcarbamoylmethyl)-3-(1-thiophen-2-yl-cycloheptanecarbonyloxy)-1azonia-bicyclo[2.2.2]octane X;
(R)-3-[1-(3-Fluoro-phenyl)-cycloheptanecarbonyloxy]-1-(pyrazin-2-ylcarbamoylmethyl)-1-azonia-bicyclo[2.2.2] octane X;
(R)-3-[1-(3-Fluoro-phenyl)-cycloheptanecarbonyloxy]-1-(isoxazol-3-ylcarbamoylmethyl)1-azonia-bicyclo[2.2.2] octane X;
(R)-3-(1-Phenyl-cycloheptanecarbonyloxy)-1-(pyridin-2-ylcarbamoylmethyl)-1-azonia-bicyclo[2.2.2]octane X;
(R)-3-(1-Phenyl-cycloheptanecarbonyloxy)-1-(pyridin-4-ylcarbamoylmethyl)-1-azonia-bicyclo[2.2.2]octane X;
(R)-1-[(5-Fluoro-pyridin-2-ylcarbamoyl)-methyl]-3-(1-phenyl-cycloheptanecarbonyloxy)-1-azonia-bicyclo[2.2.2] octane X;
(R)-1-[(5-Methyl-pyridin-2-ylcarbamoyl)-methyl]-3-(1-phenyl-cycloheptanecarbonyloxy)-1-azonia-bicyclo [2.2.2]octane X;
(R)-3-(1-Phenyl-cycloheptanecarbonyloxy)-1-(pyridin-3-ylcarbamoylmethyl)-1-azonia-bicyclo[2.2.2]octane X;
(R)-1-[(2-Methyl-pyridin-4-ylcarbamoyl)-methyl]-3-(1-phenyl-cycloheptanecarbonyloxy)azonia-bicyclo[2.2.2] octane X;
(R)-1-Phenylcarbamoylmethyl-3-(1-phenyl-cycloheptanecarbonyloxy)-1-azonia-bicyclo[2.2.2]octane X;
(R)-3-(1-Phenyl-cycloheptanecarbonyloxy)-1-(pyrimidin-4-ylcarbamoylmethyl)-1-azonia-bicyclo[2.2.2]octane X;
(R)-1-[(2-Fluoro-phenylcarbamoyl)-methyl]-3-(1-phenyl-cycloheptanecarbonyloxy)-1-azonia-bicyclo[2.2.2]octane X;
(R)-1-[(2,3-Difluoro-phenylcarbamoyl)-methyl]-3-(1-phenyl-cycloheptanecarbonyloxy)-1-azonia-bicyclo[2.2.2] octane X;

(R)-1-[2-(2,3-Dihydro-benzofuran-5-yl)-ethyl]-3-(1-phenyl-cycloheptanecarbonyloxy)-1-azonia-bicyclo[2.2.2]octane X;
(R)-1-[2-(4-Fluoro-phenoxy)-ethyl]-3-(1-phenyl-cycloheptanecarbonyloxy)-1-azonia-bicyclo[2.2.2]octane X;
(R)-3-(1-phenyl-cycloheptanecarbonyloxy)-1-(pyridazin-4-ylcarbamoylmethyl)-1-azonia-bicyclo[2.2.2]octane X;
(R)-1-[(5-Fluoro-pyridin-3-ylcarbamoyl)-methyl]-3-(1-phenyl-cycloheptanecarbonyloxy)-1-azonia-bicyclo[2.2.2]octane X;
(R)-3-(1-phenyl-cycloheptanecarbonyloxy)-1-[2-(pyridin-3-yloxy)-ethyl]-1-azonia-bicyclo[2.2.2]octane X;
(R)-1-[(6-Methyl-pyridin-2-ylcarbamoyl)-methyl]-3-(1-phenyl-cycloheptanecarbonyloxy)-1-azonia-bicyclo[2.2.2]octane X;
(R)-3-(1-Phenyl-cycloheptanecarbonyloxy)-1-(o-tolylcarbamoyl-methyl)-1-azonia-bicyclo[2.2.2]octane X;
(R)-3-(1-Phenyl-cycloheptanecarbonyloxy)-1-(2-pyrazin-2-yl-ethyl)-1-azonia-bicyclo[2.2.2]octane X;
(S)-1-(3-Phenoxy-propyl)-3-(1-phenyl-cycloheptanecarbonyloxy)-1-azonia-bicyclo[2.2.2]octane X;
(R)-1-([2-(3-Fluoro-phenoxy)-ethylcarbamoyl]-methyl)-3-(1-phenyl-cycloheptanecarbonyloxy)-1-azonia-bicyclo[2.2.2]octane X;
(R)-1-[(3,5-Difluoro-phenylcarbamoyl)-methyl]-3-(1-phenyl-cycloheptanecarbonyloxy)-1azonia-bicyclo[2.2.2]octane X;
(R)-1-[2-(4-methoxy-benzyloxy)-ethyl]-3-(1-phenyl-cycloheptanecarbonyloxy)-1-azonia-bicyclo[2.2.2]octane X;
(R)-1-(2-Phenethyloxy-ethyl)-3-(1-phenyl-cycloheptanecarbonyloxy)-1-azonia-bicyclo[2.2.2]octane X;
(R)-1-[(2,6-Difluoro-phenylcarbamoyl)-methyl]-3-(1-phenyl-cycloheptanecarbonyloxy)-1-azonia-bicyclo[2.2.2]octane X;
(R)-1-[(Methyl-phenyl-carbamoyl)-methyl]-3-(1-phenyl-cycloheptanecarbonyloxy)-1-azonia-bicyclo[2.2.2]octane X;
(R)-1-[3-(4-Cyano-phenoxy)-propyl]-3-(1-phenyl-cycloheptanecarbonyloxy)-1-azonia-bicyclo[2.2.2]octane X;
(R)-1-[(2,5-Difluoro-phenylcarbamoyl)-methyl]-3-(1-phenyl-cycloheptanecarbonyloxy)-1-azonia-bicyclo[2.2.2]octane X;
(R)-1-[2-(4-Cyano-benzyloxy)-ethyl]-3-(1-phenyl-cycloheptanecarbonyloxy)-1-azonia-bicyclo[2.2.2]octane X;
(R)-3-(1-Phenyl-cycloheptanecarbonyloxy)-1-[(6-trifluoromethyl-pyridin-2-ylcarbamoyl)-methyl]-1-azonia-bicyclo[2.2.2]octane X;
(R)-1-[(4-Methyl-pyridin-2-ylcarbamoyl)-methyl]-3-(1-phenyl-cycloheptanecarbonyloxy)-1-azonia-bicyclo[2.2.2]octane X;
(R)-1-[(5-Chloro-pyridin-2-ylcarbamoyl)-methyl]-3-(1-phenyl-cycloheptanecarbonyloxy)-1-azonia-bicyclo[2.2.2]octane X;
(R)-3-(1-Phenyl-cycloheptanecarbonyloxy)-1-(p-tolylcarbamoyl-methyl)-1-azonia-bicyclo[2.2.2]octane X;
(R)-3-(1-Phenyl-cycloheptanecarbonyloxy)-1-(m-tolylcarbamoyl-methyl)-1-azonia-bicyclo[2.2.2]octane X;
(R)-1-(Oxazol-2-ylcarbamoylmethyl)-3-(1-phenyl-cycloheptanecarbonyloxy)-1-azonia-bicyclo[2.2.2]octane X;
(R)-1-[(6-Methyl-pyridazin-3-ylcarbamoyl)-methyl]-3-(1-phenyl-cycloheptanecarbonyloxy)-1-azonia-bicyclo[2.2.2]octane X;
(R)-3-(1-Phenyl-cycloheptanecarbonyloxy)-1-(pyrimidin-2-ylcarbamoylmethyl)-1-azonia-bicyclo[2.2.2]octane X;
(R)-1-[(5-Cyano-pyridin-2-ylcarbamoyl)-methyl]-3-(1-phenyl-cycloheptanecarbonyloxy)-1-azonia-bicyclo[2.2.2]octane X;
(R)-3-(1-Phenyl-cycloheptanecarbonyloxy)-1-(pyrimidin-5-ylcarbamoylmethyl)-1-azonia-bicyclo[2.2.2]octane X;
(R)-1-[(3-Fluoro-pyridin-2-ylcarbamoyl)-methyl]-3-(1-phenyl-cycloheptanecarbonyloxy)-1-azonia-bicyclo[2.2.2]octane X;
(R)-1-[(3-Fluoro-pyridin-4-ylcarbamoyl)-methyl]-3-(1-phenyl-cycloheptanecarbonyloxy)-1-azonia-bicyclo[2.2.2]octane X;
(R)-3-(1-Phenyl-cycloheptanecarbonyloxy)-1-{2-[(pyrazine-2-carbonyl)-amino]-ethyl}-1-azonia-bicyclo[2.2.2]octane X;
(R)-3-(1-Phenyl-cycloheptanecarbonyloxy)-1-([1,2,4]thiadiazol-5-ylcarbamoylmethyl)-1-azonia-bicyclo[2.2.2]octane X;
(R)-3-(1-Phenyl-cycloheptanecarbonyloxy)-1-{3-[(pyridine-2-carbonyl-amino]-propyl}-1-azonia-bicyclo[2.2.2]octane X;
(R)-1-[(2-Methyl-pyrimidin-4-ylcarbamoyl)-methyl]-3-(1-phenyl-cycloheptanecarbonyloxy)-1-azonia-bicyclo[2.2.2]octane X;
(R)-1-[(6-Methyl-pyrimidin-4-ylcarbamoyl)-methyl]-3-(1-phenyl-cycloheptanecarbonyloxy)-1-azonia-bicyclo[2.2.2]octane X;
(R)-3-(1-Phenyl-cycloheptanecarbonyloxy)-1-{2-[(pyridine-2-carbonyl)-amino]-ethyl}-1-azonia-bicyclo[2.2.2]octane X; and
(R)-3-(1-Phenyl-cycloheptanecarbonyloxy)-1-(3-pyridin-4-yl-propyl)-1-azonia-bicyclo[2.2.2]octane X;

wherein X represents a pharmaceutically acceptable anion of a mono or polyvalent acid.

The compounds of formula (I), referred to above, and those of the present invention comprise an anion X associated with the positive charge on the quaternary nitrogen atom The anion X may be any pharmaceutically acceptable anion of a mono or polyvalent (e.g. bivalent) acid. In an embodiment of the invention X may be an anion of a mineral acid, for example chloride, bromide, iodide, sulfate, nitrate or phosphate; or an anion of a suitable organic acid, for example acetate, maleate, fumarate, citrate, oxalate, succinate, tartrate, methanesulphonate, p-toluenesulphonate, benzenesulphonate, napadisylate (naphthalene-1,5-disulfonate) (e.g. a heminapadisylate), 2,5-dichlorobenzenesulphonate, 1-hydroxynaphthalene-2-sulphonate or xinafoate (1-hydroxy-2-naphthoate).

According to the invention, there is also provided a compound selected from the group consisting on:

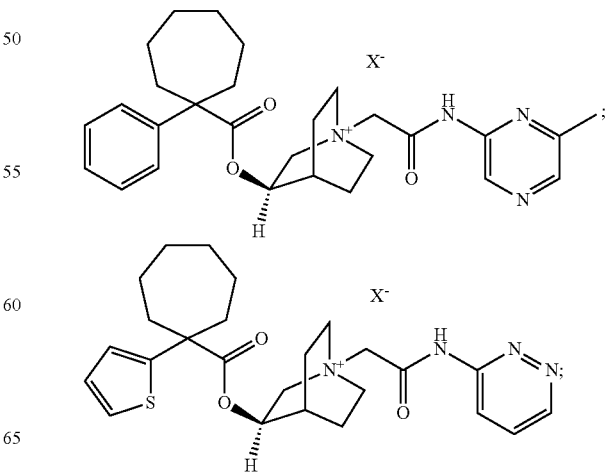

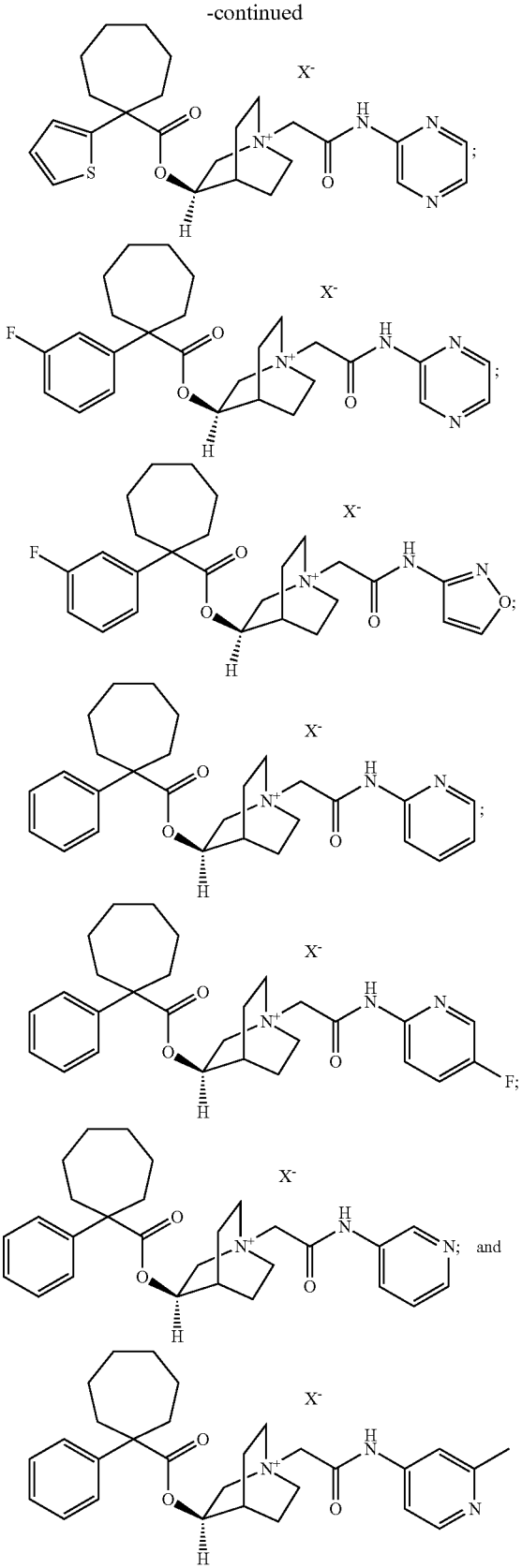

wherein X represents a pharmaceutically acceptable anion of a mono or polyvalent acid.

It will be understood that certain compounds of the present invention may exist in solvated, for example hydrated, as well as unsolvated forms. It is to be understood that the present invention encompasses all such solvated forms. Certain compounds of the present invention may exist as tautomers. Tautomers and mixtures thereof also form an aspect of the present invention.

The compounds of the present invention display beneficial pharmaceutical properties. For example, the compounds of the invention display activity as antagonists of muscarinic receptors, particularly muscarinic $M_3$ receptors. Moreover, the compounds also display desirable plasma protein binding properties. Plasma protein binding may be an advantageous property for compounds administered via inhalation as it can lessen the impact of any systemic effect the compound may have.

The compounds of the invention have activity as pharmaceuticals, in particular as anticholinergic agents including muscarinic receptor (M1, M2, and M3) antagonists, in particular M3 antagonists. Diseases and conditions which may be treated with the compounds include:

1. respiratory tract: obstructive diseases of the airways including: asthma, including bronchial, allergic, intrinsic, extrinsic, exercise-induced, drug-induced (including aspirin and NSAID-induced) and dust-induced asthma, both intermittent and persistent and of all severities, and other causes of airway hyper-responsiveness; chronic obstructive pulmonary disease (COPD); bronchitis, including infectious and eosinophilic bronchitis; emphysema; bronchiectasis; cystic fibrosis; sarcoidosis; farmer's lung and related diseases; hypersensitivity pneumonitis; lung fibrosis, including cryptogenic fibrosing alveolitis, idiopathic interstitial pneumonias, fibrosis complicating anti-neoplastic therapy and chronic infection, including tuberculosis and aspergillosis and other fungal infections; complications of lung transplantation; vasculitic and thrombotic disorders of the lung vasculature, and pulmonary hypertension; antitussive activity including treatment of chronic cough associated with inflammatory and secretory conditions of the airways, and iatrogenic cough; acute and chronic rhinitis including rhinitis medicamentosa, and vasomotor rhinitis; perennial and seasonal allergic rhinitis including rhinitis nervosa (hay fever); nasal polyposis; acute viral infection including the common cold, and infection due to respiratory syncytial virus, influenza, coronavirus (including SARS) and adenovirus;

2. bone and joints: arthritides associated with or including osteoarthritis/osteoarthrosis, both primary and secondary to, for example, congenital hip dysplasia; cervical and lumbar spondylitis, and low back and neck pain; rheumatoid arthritis and Still's disease; seronegative spondyloarthropathies including ankylosing spondylitis, psoriatic arthritis, reactive arthritis and undifferentiated spondarthropathy; septic arthritis and other infection-related arthopathies and bone disorders such as tuberculosis, including Potts' disease and Poncet's syndrome; acute and chronic crystal-induced synovitis including urate gout, calcium pyrophosphate deposition disease, and calcium apatite related tendon, bursal and synovial inflammation; Behcet's disease; primary and secondary Sjogren's syndrome; systemic sclerosis and limited scleroderma; systemic lupus erythematosus, mixed connective tissue disease, and undifferentiated connective tissue disease; inflammatory myopathies including dermatomyositits and polymyositis; polymalgia rheumatica; juvenile arthritis including idiopathic inflammatory arthritides of whatever joint distribution and associated syndromes, and rheumatic fever and its systemic complications; vasculitides including giant cell arteritis, Takayasu's arteritis, Churg-Strauss syndrome, polyarteritis nodosa, microscopic polyarteritis, and vasculitides associated with viral infection, hypersensitivity reactions, cryoglobulins, and paraproteins; low back pain; Familial Mediterranean fever, Muckle-Wells syndrome, and Familial Hibernian Fever, Kikuchi disease; drug-induced arthalgias, tendonititides, and myopathies;

3. pain and connective tissue remodelling of musculoskeletal disorders due to injury [for example sports injury] or disease: arthitides (for example rheumatoid arthritis, osteoarthritis, gout or crystal arthropathy), other joint disease (such as intervertebral disc degeneration or temporomandibular joint degeneration), bone remodelling disease (such as osteoporosis, Paget's disease or osteonecrosis), polychondritits, scleroderma, mixed connective tissue disorder, spondyloarthropathies or periodontal disease (such as periodontitis);

4. skin: psoriasis, atopic dermatitis, contact dermatitis or other eczematous dermatoses, and delayed-type hypersensitivity reactions; phyto- and photodermatitis; seborrhoeic dermatitis, dermatitis herpetiformis, lichen planus, lichen sclerosus et atrophica, pyoderma gangrenosum, skin sarcoid, discoid lupus erythematosus, pemphigus, pemphigoid, epidermolysis bullosa, urticaria, angioedema, vasculitides, toxic erythemas, cutaneous, eosinophilias, alopecia areata, male-pattern baldness, Sweet's syndrome, Weber-Christian syndrome, erythema multiforme; cellulitis, both infective and non-infective; panniculitis; cutaneous lymphomas, non-melanoma skin cancer and other dysplastic lesions; drug-induced disorders including fixed drug eruptions;

5. eyes: blepharitis; conjunctivitis, including perennial and vernal allergic conjunctivitis; iritis; anterior and posterior uveitis; choroiditis; autoimmune; degenerative or inflammatory disorders affecting the retina; ophthalmitis including sympathetic ophthalmitis; sarcoidosis; infections including viral, fungal, and bacterial;

6. gastrointestinal tract: glossitis, gingivitis, periodontitis; oesophagitis, including reflux; eosinophilic gastro-enteritis, mastocytosis, Crohn's disease, colitis including ulcerative colitis, proctitis, pruritis ani; coeliac disease, irritable bowel syndrome, and food-related allergies which may have effects remote from the gut (for example migraine, rhinitis or eczema);

7. abdominal: hepatitis, including autoimmune, alcoholic and viral; fibrosis and cirrhosis of the liver; cholecystitis; pancreatitis, both acute and chronic;

8. genitourinary: nephritis including interstitial and glomerulonephritis; nephrotic syndrome; cystitis including acute and chronic (interstitial) cystitis and Hunner's ulcer; acute and chronic urethritis, prostatitis, epididymitis, oophoritis and salpingitis; vulvo-vaginitis; Peyronie's disease; erectile dysfunction (both male and female);

9. allograft rejection: acute and chronic following, for example, transplantation of kidney, heart, liver, lung, bone marrow, skin or cornea or following blood transfusion; or chronic graft versus host disease;

10. CNS: Alzheimer's disease and other dementing disorders including CJD and nvCJD; amyloidosis; multiple sclerosis and other demyelinating syndromes; cerebral atherosclerosis and vasculitis; temporal arteritis; myasthenia gravis; acute and chronic pain (acute, intermittent or persistent, whether of central or peripheral origin) including visceral pain, headache, migraine, trigeminal neuralgia, atypical facial pain, joint and bone pain, pain arising from cancer and tumor invasion, neuropathic pain syndromes including diabetic, post-herpetic, and HIV-associated neuropathies; neurosarcoidosis; central and peripheral nervous system complications of malignant, infectious or autoimmune processes;

11. other auto-immune and allergic disorders including Hashimoto's thyroiditis, Graves' disease, Addison's disease, diabetes mellitus, idiopathic thrombocytopaenic purpura, eosinophilic fasciitis, hyper-IgE syndrome, antiphospholipid syndrome;

12. other disorders with an inflammatory or immunological component; including acquired immune deficiency syndrome (AIDS), leprosy, Sezary syndrome, and paraneoplastic syndromes;

13. cardiovascular: atherosclerosis, affecting the coronary and peripheral circulation; pericarditis; myocarditis, inflammatory and auto-immune cardiomyopathies including myocardial sarcoid; ischaemic reperfusion injuries; endocarditis, valvulitis, and aortitis including infective (for example syphilitic); vasculitides; disorders of the proximal and peripheral veins including phlebitis and thrombosis, including deep vein thrombosis and complications of varicose veins;

14. oncology: treatment of common cancers including prostate, breast, lung, ovarian, pancreatic, bowel and colon, stomach, skin and brain tumors and malignancies affecting the bone marrow (including the leukaemias) and lymphoproliferative systems, such as Hodgkin's and non-Hodgkin's lymphoma; including the prevention and treatment of metastatic disease and tumour recurrences, and paraneoplastic syndromes; and, 15. gastrointestinal tract: Coeliac disease, proctitis, eosinopilic gastro-enteritis, mastocytosis, Crohn's disease, ulcerative colitis, microscopic colitis, indeterminant colitis, irritable bowel disorder, irritable bowel syndrome, non-inflammatory diarrhea, food-related allergies which have effects remote from the gut, e.g., migraine, rhinitis and eczema.

Accordingly, the present invention further provides a compound of the present invention, as hereinbefore defined, for use in therapy.

In another aspect, the invention provides the use of a compound of the present invention, as hereinbefore defined, in the manufacture of a medicament for use in therapy.

In the context of the present specification, the term "therapy" also includes "prophylaxis" unless there are specific indications to the contrary. The terms "therapeutic" and "therapeutically" should be construed accordingly.

A further aspect of the invention provides a method of treating a disease state in a mammal suffering from, or at risk of, said disease, which comprises administering to a mammal in need of such treatment a therapeutically effective amount of a compound of the present invention, as hereinbefore defined.

The present invention also provides a compound of the present invention, as hereinbefore defined, for treating chronic obstructive pulmonary disease (COPD) (such as irreversible COPD).

The present invention also provides a compound of the present invention, as hereinbefore defined, for treating asthma.

The present invention also provides the use of a compound of the present invention, as hereinbefore defined, in the treatment of chronic obstructive pulmonary disease (COPD) (such as irreversible COPD).

The present invention also provides the use of a compound of the present invention, as hereinbefore defined, in the treatment of asthma.

The present invention also provides the use of a compound of the present invention, as hereinbefore defined, in the manufacture of a medicament for use in the treatment of chronic obstructive pulmonary disease (COPD) (such as irreversible COPD).

The present invention also provides the use of a compound of the present invention, as hereinbefore defined, in the manufacture of a medicament for use in the treatment of asthma.

The present invention further provides a method of treating chronic obstructive pulmonary disease (COPD) (such as irreversible COPD), in a warm-blooded animal, such as man which comprises administering to a mammal in need of such treatment an effective amount of a compound of the present invention, as hereinbefore defined.

The present invention further provides a method of treating asthma in a warm-blooded animal, such as man, which comprises administering to a mammal in need of such treatment an effective amount of a compound of the present invention, as hereinbefore defined.

In order to use a compound of the invention for the therapeutic treatment of a warm-blooded animal, such as man, said ingredient is normally formulated in accordance with standard pharmaceutical practice as a pharmaceutical composition.

Therefore in another aspect the present invention provides a pharmaceutical composition that comprises a compound of the invention as hereinbefore defined and a administration, inhalation being a particularly useful method for administering the invention provides a process for the preparation of said composition, which comprises mixing active ingredient with a pharmaceutically acceptable adjuvant, diluent or carrier. Depending on the mode of administration, the pharmaceutical composition will, for example, comprise from 0.05 to 99% w (percent by weight), such as from 0.05 to 80% w, for example from 0.10 to 70% w, such as from 0.10 to 50% w, of active ingredient, all percentages by weight being based on total composition.

The pharmaceutical compositions of this invention may be administered in standard manner for the disease condition that it is desired to treat, for example by topical (such as to the lung and/or airways or to the skin), oral, rectal or parenteral administration. For these purposes the compounds of this invention may be formulated by means known in the art into the form of, for example, aerosols, dry powder formulations, tablets, capsules, syrups, powders, granules, aqueous or oily solutions or suspensions, (lipid) emulsions, dispersible powders, suppositories, ointments, creams, drops and sterile injectable aqueous or oily solutions or suspensions.

A suitable pharmaceutical composition of this invention is one suitable for oral administration in unit dosage form, for example a tablet or capsule, which contains between 0.1 mg and 1 g of active ingredient.

In another aspect a pharmaceutical composition of the invention is one suitable for intravenous, subcutaneous or intramuscular injection. Each patient may receive, for example, an intravenous, subcutaneous or intramuscular dose of 0.01 $mgkg^{-1}$ to 100 $mgkg^{-1}$ of the compound, for example in the range of 0.1 $mgkg^{-1}$ to 20 $mgkg^{-1}$ of this invention, the composition being administered 1 to 4 times per day. The intravenous, subcutaneous and intramuscular dose may be given by means of a bolus injection. Alternatively the intravenous dose may be given by continuous infusion over a period of time. Alternatively each patient will receive a daily oral dose, which is approximately equivalent to the daily parenteral dose, the composition being administered 1 to 4 times per day Another suitable pharmaceutical composition of this invention is one suitable for inhaled administration, inhalation being a particularly useful method for administering the compounds of the invention when treating respiratory diseases such as chronic obstructive pulmonary disease (COPD) or asthma. When administered by inhalation the compounds of the present invention may be used effectively at doses in the μg range, for example 0.1 to 500 μg, 0.1 to 50 μg, 0.1 to 40 μg, 0.1 to 30 μg, 0.1 to 20 μg, 0.1 to 10 μg, 5 to 10 μg, 5 to 50 μg, 5 to 40 μg, 5 to 30 μg, 5 to 20 μg, 5 to 10 μg, 10 to 50 μg, 10 to 40 μg 10 to 30 μg, or 10 to 20 μg of active ingredient.

In an embodiment of the invention, there is provided a pharmaceutical composition comprising a compound of the invention as hereinbefore defined, in association with a pharmaceutically acceptable adjuvant, diluent or carrier, which is formulated for inhaled administration.

When administered by inhalation, metered dose inhaler devices may be used to administer the active ingredient, dispersed in a suitable propellant and with or without additional excipients such as ethanol, surfactants, lubricants or stabilising agents. Suitable propellants include hydrocarbon, chlorofluorocarbon and hydrofluoroalkane (e.g. heptafluoroalkane) propellants, or mixtures of any such propellants. Preferred propellants are P134a and P227, each of which may be used alone or in combination with other propellants and/or surfactant and/or other excipients. Nebulised aqueous suspensions or, preferably, solutions may also be employed, with or without a suitable pH and/or tonicity adjustment, either as a unit-dose or multi-dose formulations.

Dry powder inhalers may be used to administer the active ingredient, alone or in combination with a pharmaceutically acceptable carrier, in the later case either as a finely divided powder or as an ordered mixture. The dry powder inhaler may be single dose or multi-dose and may utilise a dry powder or a powder-containing capsule.

Metered dose inhaler, nebuliser and dry powder inhaler devices are well known and a variety of such devices are available.

The invention further relates to combination therapies wherein a compound of the invention or a pharmaceutical composition or formulation comprising a compound of the invention, is administered concurrently or sequentially or as a combined preparation with another therapeutic agent or agents, for the treatment of one or more of the conditions listed.

In particular, for the treatment of the inflammatory diseases such as (but not restricted to) rheumatoid arthritis, osteoarthritis, asthma, allergic rhinitis, chronic obstructive pulmonary disease (COPD), psoriasis, and inflammatory bowel disease, the compounds of the invention may be combined with agents listed below.

Non-steroidal anti-inflammatory agents (hereinafter NSAIDs) including non-selective cyclo-oxygenase COX-1/COX-2 inhibitors whether applied topically or systemically (such as piroxicam, diclofenac, propionic acids such as naproxen, flurbiprofen, fenoprofen, ketoprofen and ibuprofen, fenamates such as mefenamic acid, indomethacin, sulindac, azapropazone, pyrazolones such as phenylbutazone, salicylates such as aspirin); selective COX-2 inhibitors (such as meloxicam, celecoxib, rofecoxib, valdecoxib, lumarocoxib, parecoxib and etoricoxib); cyclo-oxygenase inhibiting nitric oxide donors (CINODs); glucocorticosteroids (whether administered by topical, oral, intramuscular, intravenous, or intra-articular routes); methotrexate; leflunomide; hydroxychloroquine; d-penicillamine; auranofin or other parenteral or oral gold preparations; analgesics; diacerein; intra-articular therapies such as hyaluronic acid derivatives; and nutritional supplements such as glucosamine.

The present invention still further relates to the combination of a compound of the invention together with a cytokine or agonist or antagonist of cytokine function, (including agents which act on cytokine signalling pathways such as modulators of the SOCS system) including alpha-, beta-, and gamma-interferons; insulin-like growth factor type I (IGF-1) interleukins (IL) including IL1 to 17, and interleukin antagonists or inhibitors such as anakinra; tumour necrosis factor alpha (TNF-$\alpha$) inhibitors such as anti-TNF monoclonal antibodies (for example infliximab; adalimumab, and CDP-870) and TNF receptor antagonists including immunoglobulin molecules (such as etanercept) and low-molecular -weight agents such as pentoxyfylline.

In addition the invention relates to a combination of a compound of the invention with a monoclonal antibody targeting B-Lymphocytes (such as CD20 (rituximab), MRA-aIL16R and T-Lymphocytes, CTLA4-Ig, HuMax Il-15).

The present invention still further relates to the combination of a compound of the invention with a modulator of chemokine receptor function such as an antagonist of CCR1, CCR2, CCR2A, CCR2B, CCR3, CCR4, CCR5, CCR6, CCR7, CCR8, CCR9, CCR10 and CCR11 (for the C—C family); CXCR1, CXCR2, CXCR3, CXCR4 and CXCR5 (for the C—X—C family) and $CX_3CR1$ for the C—$X_3$—C family.

The present invention further relates to the combination of a compound of the invention with an inhibitor of matrix metalloprotease (MMPs), i.e., the stromelysins, the collagenases, and the gelatinases, as well as aggrecanase; especially collagenase-1 (MMP -1), collagenase-2 (MMP-8), collagenase-3 (MMP-13), stromelysin-1 (MMP-3), stromelysin-2 (MMP-10), and stromelysin-3 (MMP-11) and MMP-9 and MMP-12, including agents such as doxycycline.

The present invention still further relates to the combination of a compound of the invention and a leukotriene biosynthesis inhibitor, 5-lipoxygenase (5-LO) inhibitor or 5-lipoxygenase activating protein (FLAP) antagonist such as; zileuton; ABT-761; fenleuton; tepoxalin; Abbott-79175; Abbott-85761; a N-(5-substituted)-thiophene-2-alkylsulfonamide; 2,6-di-tert-butylphenolhydrazones; a methoxytetrahydropyrans such as Zeneca ZD-2138; the compound SB-210661; a pyridinyl-substituted 2-cyanonaphthalene compound such as L-739,010; a 2-cyanoquinoline compound such as L-746,530; or an indole or quinoline compound such as MK-591, MK-886, and BAY×1005.

The present invention further relates to the combination of a compound of the invention and a receptor antagonist for leukotrienes (LT) B4, LTC4, LTD4, and LTE4 selected from the group consisting of the phenothiazin-3-1s such as L-651, 392; amidino compounds such as CGS-25019c; benzoxalamines such as ontazolast; benzenecarboximidamides such as BIIL 284/260; and compounds such as zafirlukast, ablukast, montelukast, pranlukast, verlukast (MK-679), RG-12525, Ro-245913, iralukast (CGP 45715A), and BAY× 7195.

The present invention still further relates to the combination of a compound of the invention and a phosphodiesterase (PDE) inhibitor such as a methylxanthanine including theophylline and aminophylline; a selective PDE isoenzyme inhibitor including a PDE4 inhibitor an inhibitor of the isoform PDE4D, or an inhibitor of PDE5.

The present invention further relates to the combination of a compound of the invention and a histamine type 1 receptor antagonist such as cetirizine, loratadine, desloratadine, fexofenadine, acrivastine, terfenadine, astemizole, azelastine, levocabastine, chlorpheniramine, promethazine, cyclizine, or mizolastine; applied orally, topically or parenterally.

The present invention still further relates to the combination of a compound of the invention and a proton pump inhibitor (such as omeprazole) or a gastroprotective histamine type 2 receptor antagonist.

The present invention further relates to the combination of a compound of the invention and an antagonist of the histamine type 4 receptor.

The present invention still further relates to the combination of a compound of the invention and an alpha-1/alpha-2 adrenoceptor agonist vasoconstrictor sympathomimetic agent, such as propylhexedrine, phenylephrine, phenylpropanolamine, ephedrine, pseudoephedrine, naphazoline hydrochloride, oxymetazoline hydrochloride, tetrahydrozoline hydrochloride, xylometazoline hydrochloride, tramazoline hydrochloride or ethylnorepinephrine hydrochloride.

The present invention still further relates to the combination of a compound of the invention and a beta-adrenoceptor agonist (including beta receptor subtypes 1-4) such as isoprenaline, salbutamol, formoterol, salmeterol, terbutaline, orciprenaline, bitolterol mesylate, pirbuterol, or indacaterol or a chiral enantiomer thereof.

The present invention further relates to the combination of a compound of the invention and a chromone, such as sodium cromoglycate or nedocromil sodium.

The present invention still further relates to the combination of a compound of the invention with a glucocorticoid, such as flunisolide, triamcinolone acetonide, beclomethasone dipropionate, budesonide, fluticasone propionate, ciclesonide or mometasone furoate.

The present invention further relates to the combination of a compound of the invention with an agent that modulates a nuclear hormone receptor such as PPARs.

The present invention still further relates to the combination of a compound of the invention together with an immunoglobulin (Ig) or Ig preparation or an antagonist or antibody modulating Ig function such as anti-IgE (for example omalizumab).

The present invention further relates to the combination of a compound of the invention and another systemic or topically-applied anti-inflammatory agent, such as thalidomide or a derivative thereof, a retinoid, dithranol or calcipotriol.

The present invention still further relates to the combination of a compound of the invention and combinations of aminosalicylates and sulfapyridine such as sulfasalazine, mesalazine, balsalazide, and olsalazine; and immunomodulatory agents such as the thiopurines, and corticosteroids such as budesonide.

The present invention further relates to the combination of a compound of the invention together with an antibacterial agent such as a penicillin derivative, a tetracycline, a macrolide, a beta-lactam, a fluoroquinolone, metronidazole, an inhaled aminoglycoside; an antiviral agent including acyclovir, famciclovir, valaciclovir, ganciclovir, cidofovir, amantadine, rimantadine, ribavirin, zanamavir and oseltamavir; a protease inhibitor such as indinavir, nelfinavir, ritonavir, and saquinavir; a nucleoside reverse transcriptase inhibitor such as didanosine, lamivudine, stavudine, zalcitabine or zidovudine; or a non-nucleoside reverse transcriptase inhibitor such as nevirapine or efavirenz.

The present invention still further relates to the combination of a compound of the invention and a cardiovascular agent such as a calcium channel blocker, a beta-adrenoceptor blocker, an angiotensin-converting enzyme (ACE) inhibitor, an angiotensin-2 receptor antagonist; a lipid lowering agent such as a statin or a fibrate; a modulator of blood cell morphology such as pentoxyfylline; thrombolytic, or an anticoagulant such as a platelet aggregation inhibitor.

The present invention further relates to the combination of a compound of the invention and a CNS agent such as an antidepressant (such as sertraline), an anti-Parkinsonian drug (such as deprenyl, L-dopa, ropinirole, pramipexole, a MAOB inhibitor such as selegine and rasagiline, a comP inhibitor such as tasmar, an A-2 inhibitor, a dopamine reuptake inhibitor, an NMDA antagonist, a nicotine agonist, a dopamine agonist or an inhibitor of neuronal nitric oxide synthase), or an anti-Alzheimer's drug such as donepezil, rivastigmine, tacrine, a COX-2 inhibitor, propentofylline or metrifonate.

The present invention still further relates to the combination of a compound of the invention and an agent for the treatment of acute or chronic pain, such as a centrally or peripherally-acting analgesic (for example an opioid or derivative thereof), carbamazepine phenyloin, sodium valproate, amitryptiline or other anti-depressant agent-s, paracetamol, or a non-steroidal anti-inflammatory agent.

The present invention further relates to the combination of a compound of the invention together with a parenterally or topically-applied (including inhaled) local anaesthetic agent such as lignocaine or a derivative thereof.

A compound of the present invention can also be used in combination with an anti-osteoporosis agent including a hormonal agent such as raloxifene, or a biphosphonate such as alendronate.

The present invention still further relates to the combination of a compound of the invention together with a: (i) tryptase inhibitor; (ii) platelet activating factor (PAF) antagonist; (iii) interleukin converting enzyme (ICE) inhibitor; (iv) IMPDH inhibitor; (v) adhesion molecule inhibitors including VLA-4 antagonist; (vi) cathepsin; (vii) kinase inhibitor such as an inhibitor of tyrosine kinase (such as Btk, Itk, Jak3 or MAP, for example Gefitinib or Imatinib mesylate), a serine/threonine kinase (such as an inhibitor of a MAP kinase such as p38, JNK, protein kinase A, B or C, or IKK), or a kinase involved in cell cycle regulation (such as a cylin dependent kinase); (viii) glucose-6 phosphate dehydrogenase inhibitor; (ix) kinin-B1.- or B2.-receptor antagonist; (x) anti-gout agent, for example colchicine; (xi) xanthine oxidase inhibitor, for example allopurinol; (xii) uricosuric agent, for example probenecid, sulfinpyrazone or benzbromarone; (xiii) growth hormone secretagogue; (xiv) transforming growth factor (TGFβ); (xv) platelet-derived growth factor (PDGF); (xvi) fibroblast growth factor for example basic fibroblast growth factor (bFGF); (xvii) granulocyte macrophage colony stimulating factor (GM-CSF); (xviii) capsaicin cream; (xix) tachykinin NK1 or NK3 receptor antagonist such as NKP-608C, SB-233412 (talnetant) or D-4418; (xx) elastase inhibitor such as UT-77 or ZD-0892; (xxi) TNF-alpha converting enzyme inhibitor (TACE); (xxii) induced nitric oxide synthase (iNOS) inhibitor; (xxiii) chemoattractant receptor-homologous molecule expressed on TH2 cells, (such as a CRTH2 antagonist); (xxiv) inhibitor of P38; (xxv) agent modulating the function of Toll-like receptors (TLR), (xxvi) agent modulating the activity of puringeric receptors such as P2x7; or (xxvii) inhibitor of transcription factor activation such as NFkB, API, or STATS.

A compound of the invention can also be used in combination with an existing therapeutic agent for the treatment of cancer, for example suitable agents include:
(i) an antiproliferative/antineoplastic drug or a combination thereof, as used in medical oncology, such as an alkylating agent (for example cis-platin, carboplatin, cyclophosphamide, nitrogen mustard, melphalan, chlorambucil, busulphan or a nitrosourea); an antimetabolite (for example an antifolate such as a fluoropyrimidine like 5-fluorouracil or tegafur, raltitrexed, methotrexate, cytosine arabinoside, hydroxyurea, gemcitabine or paclitaxel); an antitumour antibiotic (for example an anthracycline succh as adriamycin, bleomycin, doxorubicin, daunomycin, epirubicin, idarubicin, mitomycin-C dactinomycin or mithramycin); an antimitotic agent (for example a vinca alkaloid such as vincristine, vinblastine, vindesine or vinorelbine, or a taxoid such as taxol or taxotere); or a topoisomerase inhibitor (for example an epipodophyllotoxin such as etoposide, teniposide, amsacrine, topotecan or a camptothecin);
(ii) a cytostatic agent such as an antioestrogen (for example tamoxifen, toremifene, raloxifene, droloxifene or iodoxyfene), an oestrogen receptor down regulator (for example fulvestrant), an antiandrogen (for example bicalutamide, flutamide, nilutamide or cyproterone acetate), a LHRH antagonist or LHRH agonist (for example goserelin, leuprorelin or buserelin), a progestogen (for example megestrol acetate), an aromatase inhibitor (for example as anastrozole, letrozole, vorazole or exemestane) or an inhibitor of 5α-reductase such as finasteride;
(iii) an agent which inhibits cancer cell invasion (for example a metalloproteinase inhibitor like marimastat or an inhibitor of urokinase plasminogen activator receptor function);
(iv) an inhibitor of growth factor function, for example: a growth factor antibody (for example the anti-erbb2 antibody trastuzumab, or the anti-erbb1 antibody cetuximab [C225]), a farnesyl transferase inhibitor, a tyrosine kinase inhibitor or a serine/threonine kinase inhibitor, an inhibitor of the epidermal growth factor family (for example an EGFR family tyrosine kinase inhibitor such as N-(3-chloro-4-fluorophenyl)-7-methoxy-6-(3- morpholinopropoxy)quinazolin-4-amine (gefitinib, AZD 1839), N-(3-ethynylphenyl)-6,7-bis(2-methoxyethoxy) quinazolin-4-amine (erlotinib, OSI-774) or 6-acrylamido-N-(3-chloro-4-fluorophenyl)-7-(3-morpholinopropoxy) quinazolin-4-amine (CI 1033)), an inhibitor of the platelet-derived growth factor family, or an inhibitor of the hepatocyte growth factor family;
(v) an antiangiogenic agent such as one which inhibits the effects of vascular endothelial growth factor (for example the anti-vascular endothelial cell growth factor antibody bevacizumab, a compound disclosed in WO 97/22596, WO 97/30035, WO 97/32856 or WO 98/13354), or a compound that works by another mechanism (for example linomide, an inhibitor of integrin αvβ3 function or an angiostatin);
(vi) a vascular damaging agent such as combretastatin A4, or a compound disclosed in WO 99/02166, WO 00/40529, WO 00/41669, WO 01/92224, WO 02/04434 or WO 02/08213;
(vii) an agent used in antisense therapy, for example one directed to one of the targets listed above, such as ISIS 2503, an anti-ras antisense;
(viii) an agent used in a gene therapy approach, for example approaches to replace aberrant genes such as aberrant p53 or aberrant BRCA1 or BRCA2, GDEPT (gene-directed enzyme pro-drug therapy) approaches such as those using cytosine deaminase, thymidine kinanase or a bacterial nitroreductase enzyme and approaches to increase patient tolerance to chemotherapy or radiotherapy such as multidrug resistance gene therapy; or
(ix) an agent used in an immunotherapeutic approach, for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

In a further embodiment the present invention provides a pharmaceutical product comprising, in combination, a first active ingredient which is a compound of the present invention, as hereinbefore described, and at least one further active ingredient selected from:—
- a phosphodiesterase inhibitor,
- a β2. adrenoceptor agonist,
- a modulator of chemokine receptor function,
- an inhibitor of kinase function,
- a protease inhibitor,
- a steroidal glucocorticoid receptor agonist, and a
- a non-steroidal glucocorticoid receptor agonist.

The pharmaceutical product according to this embodiment may, for example, be a pharmaceutical composition comprising the first and further active ingredients in admixture. Alternatively, the pharmaceutical product may, for example, comprise the first and further active ingredients in separate pharmaceutical preparations suitable for simultaneous, sequential or separate administration to a patient in need thereof. The pharmaceutical product of this embodiment is of particular use in treating respiratory diseases such as asthma, COPD or rhinitis.

Examples of a phosphodiesterase inhibitor that may be used in the pharmaceutical product according to this embodiment include a PDE4 inhibitor such as an inhibitor of the isoform PDE4D, a PDE3 inhibitor and a PDE5 inhibitor. Examples include the compounds
- (Z)-3-(3,5-dichloro-4-pyridyl)-2-[4-(2-indanyloxy-5-methoxy-2-pyridyl]propenenitrile,
- N-[9-amino-4-oxo-1-phenyl-3,4,6,7-tetrahydropyrrolo[3,2,1-jk][1,4]benzodiazepin-3(R) -yl]pyridine-3-carboxamide (CI-1044)
- 3-(benzyloxy)-1-(4-fluorobenzyl)-N-[3-(methylsulphonyl) phenyl]-1H-indole-2-carboxamide,
- (1S-exo)-5-[3-(bicyclo[2.2.1]hept-2-yloxy)-4-methoxyphenyl]tetrahydro-2(1H)-pyrimidinone (Atizoram),
- N-(3,5dichloro-4-pyridinyl)-2-[1-(4-fluorobenzyl)-5-hydroxy-1H-indol-3-yl]-2-oxoacetamide (AWD-12-281),
- β-[3-(cyclopentyloxy)-4-methoxyphenyl]-1,3-dihydro-1,3-dioxo-2H-isoindole-2-propanamide (CDC-801),
- N-[9-methyl-4-oxo-1-phenyl-3,4,6,7-tetrahydropyrrolo[3,2,1-jk][1,4]benzodiazepin-3(R)-yl]pyridine-4-carboxamide (CI-1018),
- cis-[4-cyano-4-(3-cyclopentyloxy-4-methoxyphenyl)cyclohexane-1-carboxylic acid (Cilomilast)
- 8-amino-1,3-bis(cyclopropylmethyl)xanthine (Cipamfylline)
- N-(2,5-dichloro-3-pyridinyl)-8-methoxy-5-quinolinecarboxamide (D-4418),
- 5-(3,5-di-tert-butyl-4-hydroxybenzylidene)-2-iminothiazolidin-4-one (Darbufelone),
- 2-methyl-1-[2-(1-methylethyl)pyrazolo[1,5-a]pyridin-3-yl]-1-propanone (Ibudilast),
- 2-(2,4-dichlorophenylcarbonyl)-3-ureidobenzofuran-6-yl methanesulphonate (Lirimilast),
- (−)-(R)-5-(4-methoxy-3-propoxyphenyl)-5-methyloxazolidin-2-one (Mesopram),
- (−)-cis-9-ethoxy-8-methoxy-2-methyl-1,2,3,4,4a,10b-hexahydro-6-(4-diisopropylaminocarbonylphenyl)-benzo[c][1,6]naphthyridine (Pumafentrine),
- 3-(cyclopropylmethoxy)-N-(3,5-dichloro-4-pyridyl)-4-(difluoromethoxy)benzamide (Roflumilast),
- the N-oxide of Roflumilast,
- 5,6-diethoxybenzo[b]thiophene-2-carboxylic acid (Tibenelast)
- 2,3,6,7-tetrahydro-2-(mesitylimino)-9,10-dimethoxy-3-methyl-4H-pyrimido[6,1-a]isoquinolin-4-one (trequinsin) and
- -3-[[3-(cyclopentyloxy)-4-methoxyphenyl]-methyl]-N-ethyl-8-(1-methylethyl)-3H-purine-6-amine (V-11294A).

Examples of a β₂-adrenoceptor agonist that may be used in the pharmaceutical product according to this embodiment include metaproterenol, isoproterenol, isoprenaline, albuterol, salbutamol (e.g. as sulphate), formoterol (e.g. as fumarate), salmeterol (e.g. as xinafoate), terbutaline, orciprenaline, bitolterol (e.g. as mesylate), pirbuterol or indacaterol. The β₂-adrenoceptor agonist of this embodiment may be a long-acting β-agonists, for example salmeterol (e.g. as xinafoate), formoterol (e.g. as fumarate), bambuterol (e.g. as hydrochloride), carmoterol (TA 2005, chemically identified as 2(1H)-Quinolone, 8-hydroxy-5-[1-hydroxy-2-[[2-(4-methoxy-phenyl)-1-methylethyl]-amino]ethyl]-monohydrochloride, [R—(R*,R*)] also identified by Chemical Abstract Service Registry Number 137888-11-0 and disclosed in U.S. Pat. No. 4,579,854), indacaterol (CAS no 312753-06-3; QAB-149), formanilide derivatives e.g. 3-(4-{[6-({(2R)-2-[3-(formylamino)-4-hydroxyphenyl]-2-hydroxyethyl}amino)hexyl]oxy}-butyl)-benzenesulfonamide as disclosed in WO 2002/76933, benzenesulfonamide derivatives e.g. 3-(4-{[6-({(2R)-2-hydroxy-2-[4-hydroxy-3-(hydroxy-methyl)phenyl]ethyl}amino)-hexyl]oxy}butyl) benzenesulfonamide as disclosed in WO 2002/88167, aryl aniline receptor agonists as disclosed in WO 2003/042164 and WO 2005/025555, indole derivatives as disclosed in WO 2004/032921 and US 2005/222144, and compounds GSK 159797, GSK 159802, GSK 597901, GSK 642444 and GSK 678007.

Examples of a modulator of chemokine receptor function that may be used in the pharmaceutical product according to this embodiment include a CCR1 receptor antagonist.

Examples of an inhibitor of kinase function that may be used in the pharmaceutical product according to this embodiment include a p38 kinase inhibitor and an IKK inhibitor.

Examples of a protease inhibitor that may be used in the pharmaceutical product according to this embodiment include an inhibitor of neutrophil elastase or an inhibitor of MMP12.

Examples of a steroidal glucocorticoid receptor agonist that may be used in the pharmaceutical product according to this embodiment include budesonide, fluticasone (e.g. as propionate ester), mometasone (e.g. as furoate ester), beclomethasone (e.g. as 17-propionate or 17,21-dipropionate esters), ciclesonide, loteprednol (as e.g. etabonate), etiprednol (as e.g. dicloacetate), triamcinolone (e.g. as acetonide), flunisolide, zoticasone, flumoxonide, rofleponide, butixocort (e.g. as propionate ester), prednisolone, prednisone, tipredane, steroid esters e.g. 6α,9α-difluoro-17α-[(2-furanylcarbonyl)oxy]-11β-hydroxy -16α-methyl-3-oxo-androsta-1,4-diene-17β-carbothioic acid S-fluoromethyl ester, 6α,9α-difluoro-11β-hydroxy-16α-methyl-3-oxo-17α-propionyloxy-androsta-1,4-diene-17β-carbothioic acid S-(2-oxo-tetrahydro-furan-3S-yl)ester and 6α,9α-difluoro-11β-hydroxy -16α-methyl-17α-[(4-methyl-1,3-thiazole-5-carbonyl)oxy]-3-oxo-androsta-1,4-diene-17β-carbothioic acid S-fluoromethyl ester, steroid esters according to DE 4129535, steroids according to WO 2002/00679, WO 2005/041980, or steroids GSK 870086, GSK 685698 and GSK 799943.

Examples of a modulator of a non-steroidal glucocorticoid receptor agonist that may be used in the pharmaceutical product according to this embodiment include those described in WO2006/046916.

The invention is illustrated by the following Examples. In the Examples the following Figures are presented:

FIG. 1: X-ray powder diffraction pattern of Form A of Example 14.

Figure 2:
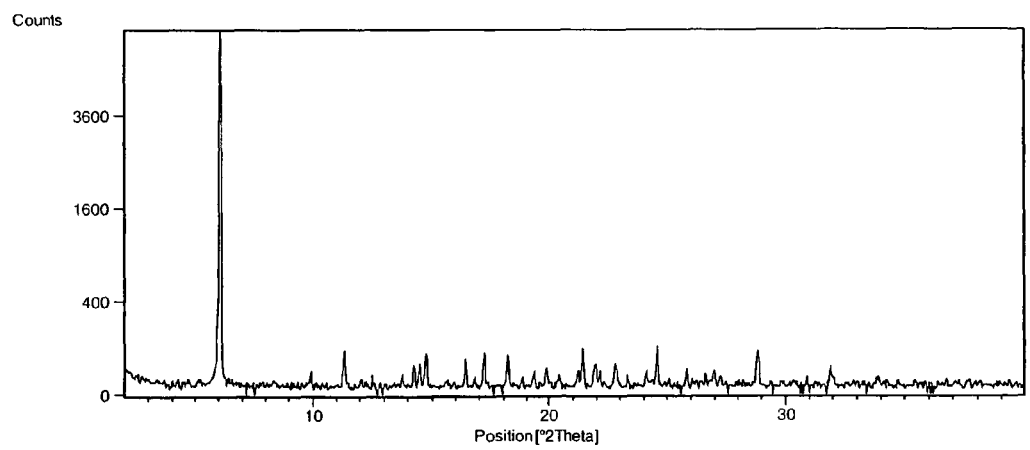

FIG. 2: X-ray powder diffraction pattern of Form A of Example 15.

In the examples the NMR spectra were measured on a Varian Unity Inova spectrometer at a proton frequency of either 300 or 400 or 500 MHz, or on a Bruker DRX spectrometer at a proton frequency of 400 or 500 MHz, or on a Bruker Avance spectrometer with a proton frequency of 600 MHz or on a Bruker Avance DPX 300 spectrometer with a proton frequency of 300 MHz. The MS spectra were measured on either an Agilent 1100 MSD G1946D spectrometer or a Hewlett Packard HP1100 MSD G1946A spectrometer or a Waters Micromass ZQ2000 spectrometer. Names were generated using the Autonom 2000 (version 4.01.305) software supplied by MDL.

XRPD data were collected using either a PANalytical CubiX PRO machine or a PANalytical X-Pert machine.

XRPD—PANalytical CubiX PRO

Data was collected with a PANalytical CubiX PRO machine in θ-θ configuration over the scan range 2° to 40° 2θ with 100-second exposure per 0.02° increment. The X-rays were generated by a copper long-fine focus tube operated at 45 kV and 40 mA. The wavelength of the copper X-rays was 1.5418 Å. The Data was collected on zero background holders on which ~2 mg of the compound was placed. The holder was made from a single crystal of silicon, which had been cut along a non-diffracting plane and then polished on an optically flat finish. The X-rays incident upon this surface were negated by Bragg extinction.

PANalytical X-Pert

Data was collected using a PANalytical X-Pert machine in 2θ-θ configuration over the scan range 2° to 40° 2θ with 100-second exposure per 0.02° increment. The X-rays were generated by a copper long-fine focus tube operated at 45 kV and 40 mA. The wavelengths of the copper X-rays was 1.5418 Å. The Data was collected on zero background holders on which ~2 mg of the compound was placed. The holder was made from a single crystal of silicon, which had been cut along a non-diffracting plane and then polished on an optically flat finish. The X-rays incident upon this surface were negated by Bragg extinction.

DSC thermograms were measured using a TA Q1000 Differential Scanning Calorimeter, with aluminium pans and pierced lids. The sample weights varied between 0.5 to 5 mG. The procedure was carried out under a flow of nitrogen gas (50 mL/min) and the temperature studied from 25 to 300° C. at a constant rate of temperature increase of 10° C. per minute.

TGA thermograms were measured using a TA Q500 Thermogravimetric Analyser, with platinum pans. The sample weights varied between 1 and 5 mg. The procedure was carried out under a flow of nitrogen gas (60 mL/min) and the temperature studied from 25 to 300° C. at a constant rate of temperature increase of 10° C. per minute.

GVS profiles were measured using a Dynamic Vapour Sorption DVS-1 instrument. The solid sample ca. 1-5 mg was placed into a glass vessel and the weight of the sample was recorded during a dual cycle step method (40 to 90 to 0 to 90 to 0% relative humidity (RH), in steps of 10% RH).

Abbreviations used in the experimental section:
Aq=aqueous
DCE=1,2-dichloroethane
DCM=dichloromethane
is DMF=dimethylformamide
DMSO=Dimethylsulfoxide
EtOAc=ethyl acetate
EtOH=ethanol
GVS=Gravimetric vapour sorption
HATU=O-(7-Azabenzotriazol-1-yl)-N,N,N',N'-tetramethyluronium hexafluorophosphate
MeCN—Acetonitrile
MeOH=methanol
RT=RT
Rt=retention time
THF=tetrahydrofuran
Satd=saturated
DSC=Differential Scanning Calorimetry
TGA=Thermogravimetric analysis
XRPD=X-Ray Powder Diffraction

EXAMPLE 1

(R)-1-[(6-Methyl-pyridin-3-ylcarbamoyl)-methyl]-3-(1-phenyl-cycloheptanecarbonyloxy)-1-azonia-bicyclo[2.2.2]octane chloride a) 1-Phenyl-cycloheptanol

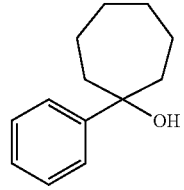

To magnesium (1.2 g) in anhydrous tetrahydrofuran (60 mL) under an environment of nitrogen was added a crystal of iodine followed by bromobenzene (7.85 g) at such a rate that the reaction maintained a steady reflux. The reaction mixture was stirred for 20 minutes then cycloheptanone (4.48 g) was added with care. After stirring for 10 minutes saturated aqueous ammonium chloride (10 mL) was added and the reaction was partitioned to between water (100 mL) and isohexane (100 mL). The organic layer was dried (MgSO$_4$) and evaporated to afford the sub-titled compound (7.6 g) as an oil.

$^1$H-NMR (300 MHz, CDCl$_3$) δ 7.53-7.47 (m, 2H), 7.36-7.29 (m, 2H), 7.26-7.19 (m, 1H), 2.07 (ddd, 2H), 1.97-1.50 (m, 11H).

b) 1-Methoxy-1-phenyl-cycloheptane

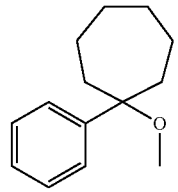

1-Phenyl-cycloheptanol (Example 1a) (7.6 g) was dissolved in tetrahydrofuran (100 mL) and sodium hydride (60% in oil, 2.0 g) added. The reaction was stirred at 60° C. for 5 minutes and iodomethane (7.1 g) added. The mixture was maintained at 60° C. overnight and then further quantities of sodium hydride (60% in oil, 2.0 g) and iodomethane (7.1 g) were added and the reaction was refluxed for 70 hours. The reaction mixture was partitioned between water (100 mL) and isohexane (100 mL) and the organic layer separated, dried (MgSO$_4$) and evaporated to afford the sub-titled compound (11.31 g).

¹H NMR (300 MHz, CDCl₃) δ 7.43-7.37 (m, 2H), 7.37-7.30 (m, 2H), 7.24-7.19 (m, 1H), 2.98 (s, 3H), 2.12-1.88 (m, 4H), 1.88-1.45 (m, 8H).

c) 1-Phenyl-cycloheptanecarboxylic acid

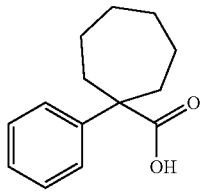

Potassium (2.62 g) and sodium (0.52 g) were heated together at 120° C. in mineral oil under an environment of nitrogen for 30 minutes and then cooled to room temperature. The oil was removed and replaced with ether (100 mL) and 1-methoxy-1-phenyl-cycloheptane (Example 1b) (4.9 g) was added and the reaction was stirred under nitrogen overnight at room temperature. The reaction was cooled to −78° C. and solid carbon dioxide (~20 g) was added with stirring. The reaction was allowed to warm to room temperature and water (150 mL) was added carefully under an environment of nitrogen. The aqueous layer was separated, neutralised with concentrated hydrochloric acid and extracted with diethyl ether (150 mL). The organic layer was dried (MgSO₄) and evaporated afford to the sub-titled compound (4.15 g) as an oil.

¹H NMR (300 MHz, CDCl₃) δ 7.40-7.20 (m, 5H), 2.49-2.35 (m, 2H), 2.16-2.03 (m, 2H), 1.76-1.47 (m, 8H).

d) 1-Phenyl-cycloheptanecarboxylic acid methyl ester

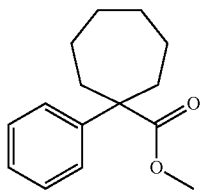

1-Phenyl-cycloheptanecarboxylic acid (Example 1c) (4.15 g) was refluxed in methanol (150 mL) and concentrated hydrochloric acid (5 mL) for 24 hours. The solvent was evaporated and the residue was dissolved in ether (100 mL) which was washed with water (100 mL), saturated sodium bicarbonate (50 mL) and water (100 mL), dried (MgSO₄) and evaporated to afford the sub-titled compound (3.5 g) as an oil.

¹H NMR (300 MHz, CDCl₃) δ 7.37-7.18 (m, 5H), 3.63 (s, 3H), 2.47-2.35 (m, 2H), 2.08-1.97 (m, 2H), 1.70-1.48 (m, 8H).

e) 1-Phenyl-cycloheptanecarboxylic acid (R)-(1-aza-bicyclo[2.2.2]oct-3-yl)ester

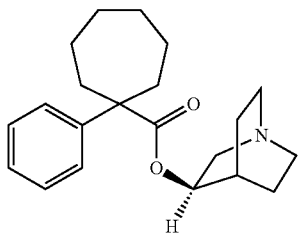

1-Phenyl-cycloheptanecarboxylic acid methyl ester (Example 1d) (1.0 g) and (R)-quinuclidin-3-ol (0.39 g) were refluxed in heptane (50 mL) containing sodium (~5 mg in a Dean and Stark apparatus for 24 hours. Heptane (20 mL) was replaced with toluene (20 mL) and the reflux was continued for 3 days. The reaction was partitioned between water (50 mL) and ether (50 mL) and the ether layer was separated, dried (MgSO₄) and evaporated. The crude product was purified by column chromatography on silica elutting with ethyl acetate/triethylamine (99/1) to afford the titled compound as an oil (0.83 g).

m/e 328 [M+H]⁺

¹NMR (300 MHz, CDCl₃) δ 7.35-7.27 (m, 4H), 7.23-7.16 (m, 1H), 4.78-4.71 (m, 1H), 3.12 (ddd, 1H), 2.79-2.32 (m, 7H), 2.16-1.98 (m, 2H), 1.91-1.80 (m, 1H), 1.70-1.34 (m, 12H).

f) 2-Chloro-N-(6-methyl-pyridin-3-yl)-acetamide

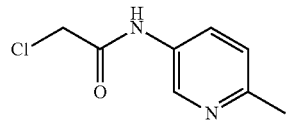

A mixture of 6-methylpyridin-3-amine (1 g) and triethylamine (2.2 mL) in dry THF (20 mL) was stirred and cooled to −60° C. 2-Chloroacetyl chloride (1.567 g) was added via syringe to the stirred mixture forming a yellow suspension. The mixture was stirred at −60° C. until analysis showed complete disappearance of starting material. The reaction slurry was poured into water and the products extracted with ethyl acetate (2×150 ml). The combined organic extracts were dried over magnesium sulphate and concentrated to dryness. The crude brown solid was recrystallised from ether to afford the subtitled compound (700 mg).

¹H NMR (400 MHz, DMSO-D₆) δ 10.40 (1H, s), 8.60 (1H, d), 7.91 (1H, dd), 7.22 (1H, d), 4.27 (2H, s), 2.42 (3H, s).

EXAMPLE 1

(R)-1-[(6-Methyl-pyridin-3-ylcarbamoyl)-methyl]-3-(1-phenyl-cycloheptanecarbonyloxy)-1-azonia-bicyclo[2.2.2]octane chloride

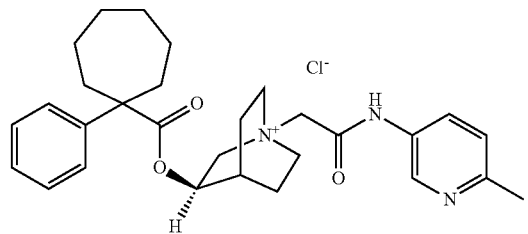

1-Phenyl-cycloheptanecarboxylic acid (R)-(1-aza-bicyclo[2.2.2]oct-3-yl)ester (Example 1e)(52 mg) was dissolved in acetonitrile (2 mL) and 2-chloro-N-(6-methylpyridin-3-yl) acetamide (Example f) (29 mg) was added. The reaction mixture was stirred for 10 days and diluted with ethyl acetate (4 mL) and isohexane (14 mL). The mixture was left standing for 5 days, whereupon the resulting crystals were separated and washed with diethyl ether (0.5 mL) to afford the titled compound as a solid (36 mg).

m/e 476 [M]⁺

¹H-NMR (400 MHz, DMSO-D₆) δ 11.33 (s, 1H), 8.70 (d, 1H), 7.91 (dd, 1H), 7.38-7.30 (m, 4H), 7.27 (d, 1H), 7.28-7.20 (m, 1H), 5.16-5.07 (m, 1H), 4.36 (d, 1H), 4.31 (d, 1H), 4.16-

4.07 (m, 1H), 3.72-3.54 (m, 4H), 3.44-3.34 (m, 2H), 2.44 (s, 3H), 2.42-2.28 (m, 2H), 2.22-2.10 (m, 2H), 2.01-1.86 (m, 3H), 1.83-1.71 (m, 1H), 1.69-1.41 (m, 8H).

EXAMPLE 2

(R)-1-[(6-Methyl-pyrazin-2-ylcarbamoyl)-methyl]-3-(1-phenyl-cycloheptanecarbonyloxy)-1-azonia-bicyclo[2.2.2]octane bromide a) 2-Bromo-N-(6-methyl-pyrazin-2-yl)-acetamide

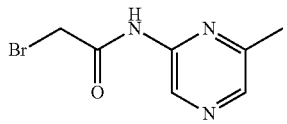

6-Methyl-pyrazin-2-ylamine (150 mg) and potassium carbonate (571 mg) were added to dichloromethane (25 mL). 2-Bromoacetyl bromide (0.120 mL) was added to the suspension with stirring. The reaction was stirred overnight then water (0.1 mL) was added with further stirring. Further quantities of potassium carbonate (571 mg), 2-bromoacetyl bromide (0.120 mL) and water (0.1 mL) were added over 2 hours until the reaction had proceeded to completion. The reaction was diluted with water (100 mL), carefully acidified with hydrochloric acid and extracted with dichloromethane (2×50 mL) which was dried and evaporated to afford the sub-titled compound which was used crude (365 mg).

$^1$H NMR (400 MHz, CDCl$_3$) δ 9.45 (s, 1H), 9.37 (s, 1H), 8.33 (s, 1H), 4.05 (s, 2H), 2.51 (s, 3H).

EXAMPLE 2

(R)-1-[(6-Methyl-pyrazin-2-ylcarbamoyl)-methyl]-3-(1-phenyl-cycloheptanecarbonyloxy)-1-azonia-bicyclo[2.2.2]octane bromide

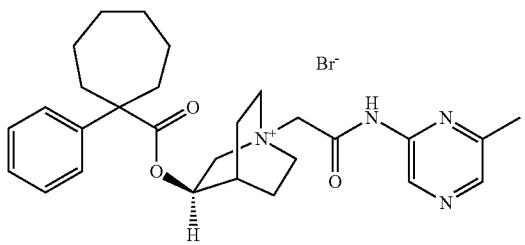

1-Phenyl-cycloheptanecarboxylic acid (R)-(1-aza-bicyclo[2.2.2]oct-3-yl)ester (Example 1e) (70 mg) and 2-bromo-N-(6-methylpyrazin-2-yl) acetamide (Example 2a) (49.2 mg) were dissolved in acetonitrile (1 mL) and left to stand overnight. Crystals separated on standing and were filtered and washed with acetonitrile (2×1 mL), ethyl acetate (2×3 mL) and diethyl ether (2×3 mL) and dried to yield the titled compound (24 mg).

m/e 477 [M]$^+$ $^1$H NMR (400 MHz, DMSO-D$_6$) δ 11.33 (s, 1H), 9.09 (s, 1H), 8.37 (s, 1H), 7.38-7.31 (m, 4H), 7.27-7.22 (m, 1H), 5.15-5.09 (m, 1H), 4.36-4.25 (m, 2H), 4.16-4.07 (m, 1H), 3.68-3.56 (m, 4H), 3.46-3.33 (m, 1H), 2.47 (s, 3H), 2.42-2.29 (m, 2H), 2.24-2.11 (m, 2H), 2.04-1.87 (m, 3H), 1.83-1.73 (m, 1H), 1.68-1.45 (m, 9H).

EXAMPLE 3

(R)-3-(1-Phenyl-cycloheptanecarbonyloxy)-1-[(6-trifluoromethyl-pyridazin-3-ylcarbamoyl)-methyl]-1-azonia-bicyclo[2.2.2]octane bromide a) 2-Bromo-N-(6-trifluoromethyl-pyridazin-3-yl)-acetamide

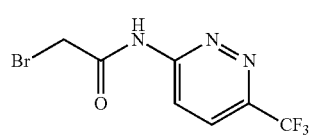

6-Trifluoromethyl-pyridazin-3-ylamine (0.042 g) (prepared by a procedure similar to that described in WO2007048779) was dissolved in dichloromethane (40 mL) and stirred with potassium carbonate (0.214 g). 2-Bromoacetyl bromide (0.12 mL) was added and stirring continued for 1.5 hours. Water (0.24 mL) was added and the reaction mixture was stirred for 1.5 hours after which water (40 mL) was added and the reaction mixture stirred for a further 1.5 hours. The dichloromethane was separated, dried (MgSO$_4$) and evaporated to afford the sub-titled compound as a white solid (0.053 g).

m/e 284/286 [M+H]$^+$ $^1$H NMR (400 MHz, DMSO-D$_6$) δ 11.04 (s, 1H), 8.79 (d, 1H), 7.91 (d, 1H), 4.31 (s, 2H).

EXAMPLE 3

(R)-3-(1-Phenyl-cycloheptanecarbonyloxy)-1-[(6-trifluoromethyl-pyridazin-3-ylcarbamoyl)-methyl]-1-azonia-bicyclo[2.2.2]octane bromide

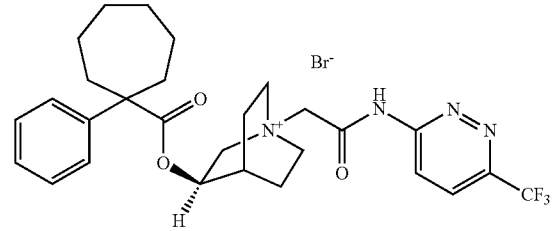

1-Phenyl-cycloheptanecarboxylic acid (R)-(1-aza-bicyclo[2.2.2]oct-3-yl)ester (Example 1e) (61.1 mg) and 2-bromo-N-(6-trifluoromethyl-pyridazin-3-yl)-acetamide (Example 3a) (53.0 mg) were dissolved in acetonitrile (2 mL) and left overnight. The solvent was evaporated and the product was purified by column chromatography on silica eluting with 10% methanol in dichloromethane to afford the titled compound (107 mg).

m/e 531 [M]$^+$ $^1$H NMR (400 MHz, DMSO-D$_6$) δ 12.17 (s, 1H), 8.50 (d, 1H), 8.36 (d, 1H), 7.40-7.32 (m, 4H), 7.28-7.23 (m, 1H), 5.17-5.10 (m, 1H), 4.57-4.42 (m, 2H), 4.22-4.14 (m, 1H), 3.76-3.61 (m, 4H), 3.47 (dd, 1H), 2.43-2.30 (m, 2H), 2.25-2.12 (m, 2H), 2.07-1.88 (m, 3H), 1.86-1.73 (m, 1H), 1.72-1.44 (m, 9H).

EXAMPLE 4

(R)-1-(Benzo[d]isoxazol-3-ylcarbamoylmethyl)-3-(1-phenyl-cycloheptanecarbonyloxy)-1-azonia-bicyclo[2.2.2]octane bromide a) N-Benzo[d]isoxazol-3-yl-2-chloro-acetamide

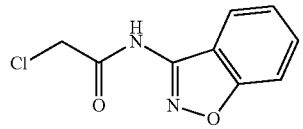

To a mixture of benzo[d]isoxazol-3-ylamine (1 g) and cesium carbonate (2.42 g) in dry DMF (20 mL), stirred at rt, was added bromoacetyl chloride (0.62 mL) by dropwise addition. After stirring the mixture for 8 hours, the reaction was poured into water (100 mL) and the products extracted into ether (2×200 mL). The combined extracts were dried over magnesium sulfate and concentrated to dryness. The crude product was purified on silica gel using ether/isohexane (4/6) to afford the sub-titled compound as a colourless solid (0.5 g).

m/e 210 [M+H]$^+$

EXAMPLE 4

(R)-1-(Benzo[d]isoxazol-3-ylcarbamoylmethyl)-3-(1-phenyl-cycloheptanecarbonyloxy)-1-azonia-bicyclo[2.2.2]octane chloride

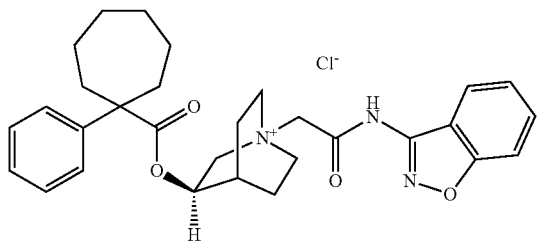

1-Phenyl-cycloheptanecarboxylic acid (R)-(1-aza-bicyclo[2.2.2]oct-3-yl)ester (Example 1e) (114 mg) and N-benzo[d]isoxazol-3-yl-2-chloro-acetamide (Example 4a) (89 mg) were dissolved in acetonitrile (10 mL) and left for one week. The resulting crystals were filtered off and washed with diethyl ether (3×10 mL) to afford the titled compound as a solid (120 mg).

m/e 502 [M]$^+$ $^1$H NMR (400 MHz, DMSO-D$_6$) δ 12.15 (s, 1H), 8.16 (d, 1H), 7.74 (d, 1H), 7.72-7.67 (m, 1H), 7.44-7.39 (m, 1H), 7.38-7.30 (m, 4H), 7.27-7.19 (m, 1H), 5.18-5.11 (m, 1H), 4.63-4.46 (m, 2H), 4.17 (ddd, 1H), 3.76-3.61 (m, 4H), 3.49 (dd, 1H), 2.43-2.29 (m, 2H), 2.24-2.12 (m, 2H), 2.03-1.89 (m, 3H), 1.86-1.74 (m, 1H), 1.70-1.44 (m, 9H).

EXAMPLE 5

(R)-1-(Pyridazin-3-ylcarbamoylmethyl)-3-(1-thiophen-2-yl-cycloheptanecarbonyloxy)-1-azonia-bicyclo[2.2.2]octane bromide a) 2-But-3-enyl-2-thiophen-2-yl-hex-5-enoic acid ethyl ester

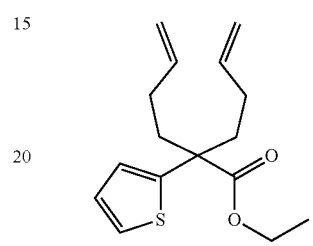

Ethyl 2-(thiophen-2-yl)acetate (2.35 g) was dissolved in tetrahydrofuran (30 mL) and cooled to −78° C. Lithium bis(trimethylsilyl)amide (2.31 g) in THF (1M solution, 13.8 mL) was added and the solution was stirred for 30 minutes. 4-Bromo-but-1-ene (1.4 mL) was added and the reaction mixture was allowed to warm to room temperature and stirred for 1 hour. The reaction mixture was re-cooled to −78° C. and lithium bis(trimethylsilyl)amide (2.31 g) in THF (1M solution, 13.8 mL) was added and the solution was stirred for 30 minutes. 4-Bromo-but-1-ene (1.4 mL) was added and the reaction mixture was allowed to warm to room temperature and stand overnight. HPLC-MS analysis indicated that the reaction was incomplete so the reaction was again cooled to −78° C. and further aliquots of lithium bis(trimethylsilyl) amide (1M solution, 10 mL) and 4-bromo-but-1-ene (1.0 mL) were added following the procedure outlined above. After stirring for a further 2 hours, water (30 mL) was added and the reaction was extracted with diethyl ether (2×60 mL). The combined organic extracts were dried (MgSO$_4$) and evaporated. The resulting oil was purified by column chromatography on silica eluting with ethyl acetate/isohexane (1/99) afford the sub-titled compound (3.18 g).

$^1$H NMR (400 MHz, DMSO-D$_6$) δ 7.21 (dd, 1H), 6.97-6.94 (m, 2H), 5.79 (ddt, 2H), 5.01 (dq, 2H), 4.95 (dq, 2H), 4.17 (q, 2H), 2.22-2.08 (m, 4H), 2.00-1.85 (m, 4H), 1.24 (t, 3H b) 1-Thiophen-2-yl-cyclohept-4-enecarboxylic acid ethyl ester

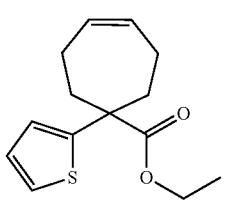

To 2-but-3-enyl-2-thiophen-2-yl-hex-5-enoic acid ethyl ester (Example 5a) (3.18 g) in dichloromethane (100 mL) was added Grubbs Catalyst (2nd Generation, Sigma-Aldrich Company Ltd) (0.100 g). The mixture was warmed to reflux under nitrogen. After 20 hours the mixture was allowed to cool to room temperature and evaporated to an oil. Purification by column chromatography on silica eluting with ethyl acetate/isohexane (10:90) to yield the sub-titled compound (2.60 g) as a coloured oil.

$^1$H NMR (400 MHz, DMSO-D$_6$) δ 7.19 (dd, 1H), 6.98-6.92 (m, 2H), 5.72 (t, 2H), 4.15 (q, 2H), 2.66-2.59 (m, 2H), 2.25-2.14 (m, 6H), 1.21 (t, 3H).

c) 1-Thiophen-2-yl-cycloheptanecarboxylic acid ethyl ester

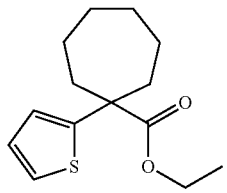

1-Thiophen-2-yl-cyclohept-4-enecarboxylic acid ethyl ester (Example 5b) (2.86 g) was dissolved in ethanol (30 mL) and tris(triphenylphosphine)rhodium(I) chloride (0.100 g) was added. The reaction mixture was stirred rapidly under 5 atmospheres of hydrogen overnight. Further tris(triphenylphosphine)rhodium(I) chloride (0.050 g) was added and the reaction mixture was stirred under 5 atmospheres of hydrogen for 3 days. A third addition of tris(triphenylphosphine)rhodium(I) chloride (0.050 g) was made and the reaction mixture was stirred under 3 atmospheres of hydrogen overnight. The contents were evaporated to dryness and purified on silica eluting with ethyl acetate/isohexane (5/95) to afford the sub-titled compound (2.500 g) as a clear almost colourless oil m/e 253 [M+H$^+$]

$^1$H-NMR (400 MHz, DMSO-D$_6$) δ 7.17 (dd, 1H), 6.95-6.91 (m, 2H), 4.13 (q, 2H), 2.53 (dd, 2H), 2.14-2.03 (m, 2H), 1.70-1.50 (m, 8H), 1.20 (t, 3H).

d) 1-Thiophen-2-yl-cycloheptanecarboxylic acid (R)-(1-aza-bicyclo[2.2.2]oct-3-yl)ester

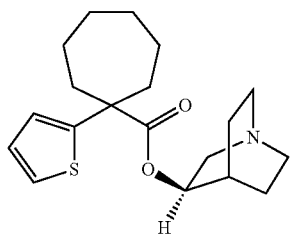

1-Thiophen-2-yl-cycloheptanecarboxylic acid ethyl ester (Example 5c) (2.5 g) and (R)-quinuclidin-3-ol (2.08 g) were dissolved in toluene (350 mL) and sodium hydride (0.1 g) added under nitrogen. The mixture was heated to reflux for 20 hours after which the toluene was carefully distilled off to leave ~100 mL which was cooled and washed with water (100 mL), dried (MgSO$_4$) and evaporated. The crude product was purified by column chromatography on silica eluting with ethyl acetate/triethylamine (99/1) to afford the sub-titled compound (2.84 g).

m/e 334 [M+H$^+$]

$^1$H NMR (400 MHz, CDCl$_3$) δ 7.18 (t, 1H), 6.95-6.92 (m, 2H), 4.77-4.72 (m, 1H), 3.14 (ddd, 1H), 2.83-2.64 (m, 4H), 2.59-2.50 (m, 3H), 2.18-2.08 (m, 2H), 1.95-1.90 (m, 1H), 1.71-1.44 (m, 11H), 1.34-1.23 (m, 1H).

e) 2-Bromo-N-pyridazin-3-yl-acetamide

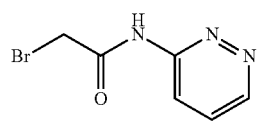

To a suspension of pyridazin-3-ylamine (2.7 g) and diisopropylethylamine (6.3 mL) in dichloromethane (100 mL) at 0° C. was added bromoacetic anhydride (9.0 g) in dichloromethane (10 mL) by dropwise addition. The mixture was stirred at 0° C. for 0.5 hours and then allowed to warm to rt. The resulting suspension was filtered, washed with dichloromethane and dried to afford the sub-titled compound as a solid (2.0 g).

$^1$H NMR (400 MHz, DMSO-D$_6$) δ 11.51 (s, 1H), 9.00 (dd, 1H), 8.28 (dd, 1H), 7.74-7.68 (m, 1H), 4.15 (s, 2H).

EXAMPLE 5

(R)-1-(Pyridazin-3-ylcarbamoylmethyl)-3-(1-thiophen-2-yl-cycloheptanecarbonyloxy)-1-azoniabicyclo[2.2.2]octane bromide

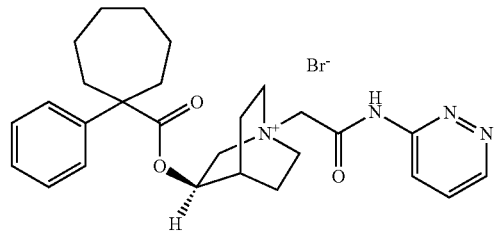

1-Thiophen-2-yl-cycloheptanecarboxylic acid (R)-(1-aza-bicyclo[2.2.2]oct-3-yl)ester (Example 5d) (80 mg) and 2-bromo-N-pyridazin-3-yl-acetamide (Example 5e) (52 mg) were dissolved in acetonitrile (3 mL) and stirred overnight. Ethyl acetate (9 mL) and isohexane (4 mL) were added and stirred overnight. The resulting crystals were filtered off and then triturated with ethyl acetate to afford the titled compound (14 mg).

m/e 469 [M$^+$]

$^1$H NMR (400 MHz, DMSO-D$_6$) δ 11.68 (s, 1H), 9.05 (dd, 1H), 8.25 (d, 1H), 7.79 (dd 1H), 7.44 (dd, 1H), 7.03 (dd, 1H), 6.99 (dd, 1H), 5.14-5.09 (m, 1H), 4.37 (s, 2H), 4.17-4.08 (m, 1H), 3.76-3.57 (m, 4H), 3.57-3.46 (m, 1H), 2.48-2.42 (m,

1H), 2.29-2.22 (m, 1H), 2.21-2.11 (m, 1H), 2.07-1.90 (m, 4H), 1.90-1.80 (m, 1H), 1.78-1.68 (m, 1H) 1.66-1.46 (m, 8H).

EXAMPLE 6

(R)-1-[(5-Methyl-isoxazol-3-ylcarbamoyl)-methyl]-3-(1-thiophen-2-yl-cycloheptanecarbonyloxy)-1-azonia-bicyclo[2.2.2]octane bromide a) 2-Bromo-N-(5-methyl-isoxazol-3-yl)-acetamide

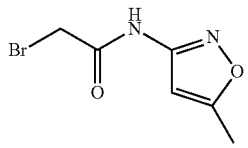

To a stirred suspension of sodium bicarbonate (1.242 g) and 5-methyl-isoxazol-3-ylanamine (1.45 g) in dichloromethane (50 mL) was added 2-bromoacetyl bromide (1.28 mL) by dropwise addition. The reaction mixture was stirred overnight and then washed with water (2×50 mL). The organic fraction was separated, dried with magnesium sulfate and evaporated to yield the sub-titled compound (279 mg).

¹H NMR (400 MHz, DMSO-D$_6$) δ 11.32 (s, 1H), 6.62 (s, 1H), 4.06 (s, 2H), 2.38 (s, 3H).

EXAMPLE 6

(R)-1-[(5-Methyl-isoxazol-3-ylcarbamoyl)-methyl]-3-(1-thiophen-2-yl cycloheptanecarbonyloxy)-1-azonia-bicyclo[2.2.2]octane bromide

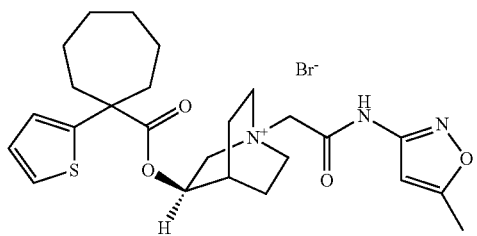

1-Thiophen-2-yl-cycloheptanecarboxylic acid (R)-(1-azabicyclo[2.2.2]oct-3-yl)ester (Example 5d) (68 mg) and 2-bromo-N-(5-methyl-isoxazol-3-yl)-acetamide (Example 6a) (45 mg) were dissolved in acetonitrile (2 mL) and stirred overnight. Ethyl acetate (10 mL) and isohexane (9 mL) were added and stirred overnight. The resulting crystals were filtered off and washed with ethyl acetate to afford the titled compound (82 mg).

m/e 472 [M⁺]

¹H NMR (400 MHz, DMSO-D6) δ 11.55 (s, 1H), 7.44 (dd, 1H), 7.03 (dd, IH), 6.99 (dd, 1H), 6.61 (s, 1H), 5.13-5.08 (m, 1H), 4.31 (d, 1H), 4.26 (d, 1H), 4.14-4.05 (m, 1H), 3.72-3.55 (m, 4H), 3.53-3.43 (m, 1H), 2.54-2.42 (m, 1H), 2.41 (d, 3H), 2.27-2.22 (m, 1H) 2.19-2.13 (m, 1H), 2.07-1.90 (m, 4H), 1.89-1.77 (m, 1H), 1.77-1.65 (m, 1H), 1.63-1.48 (m, 8H).

EXAMPLE 7

(R)-1-[(3-Methyl-isoxazol-5-ylcarbamoyl)-methyl]-3-(1-thiophen-2-yl-cycloheptanecarbonyloxy)-1-azonia-bicyclo[2.2.2]octane bromide a) 2-Bromo-N-(3-methyl-isoxazol-5-yl)-acetamide

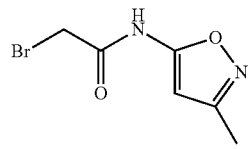

3-Methyl-isoxazol-5-ylamine (2.9 g) and potassium carbonate (9.8 g) were suspended in dichloromethane (100 mL) at room temperature and 2-bromoacetyl bromide (6 g) was added dropwise. The mixture was allowed to stir overnight. Water (0.3 mL) was added together with a further quantity of potassium carbonate (3 g) and the reaction mixture stirred for a further 30 minutes. The reaction mixture was poured into water (100 mL) and extracted with dichloromethane (2×50 mL). The combined organic extracts were dried over magnesium sulfate and then evaporated in vacuo. The crude product was purifed by column chromatography on silica eluting with ethyl acetate/isohexane (50:50) to give sub-titled compound (4.8 g).

¹H NMR (300 MHz, CDCl$_3$) δ 11.97 (s, 1H), 6.16 (s, 1H), 4.09 (s, 2H), 2.19 (s, 3H).

EXAMPLE 7

(R)-1-[(3-Methyl-isoxazol-5-ylcarbamoyl)-methyl]-3-(1-thiophen-2-yl cycloheptanecarbonyloxy)-1-azonia-bicyclo[2.2.2]octane bromide

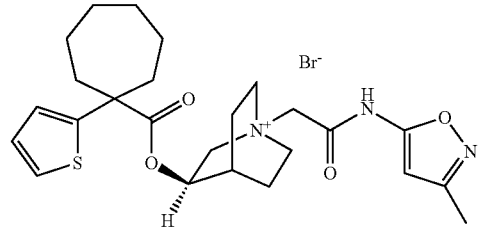

1-Thiophen-2-yl-cycloheptanecarboxylic acid (R)-(1-azabicyclo[2.2.2]oct-3-yl)ester (Example 5d) (50 mg) and 2-bromo-N-(3-methylisoxazol-5-yl)acetamide (Example 7a) (32 mg) were dissolved in acetonitrile (2 mL) and left overnight. Ethyl acetate (10 mL) and isohexane (10 mL) were added and the crystals filtered off, washed with ethyl acetate and dried to afford the titled compound (37 mg).

m/e 472 [M⁺]

¹H NMR (400 MHz, DMSO-D$_6$) δ 12.21 (s, 1H), 7.44 (dd, 1H), 7.03 (dd, 1H), 6.99 (dd, 1H), 6.18 (s, 1H), 5.15-5.07 (m, 1H), 4.35 (d, 1H), 4.30 (d, 1H), 4.14-4.05 (m, 1H), 3.73-3.54 (m, 4H), 3.54-3.43 (m, 1H), 3.17 (d, 1H), 2.47-2.42 (m, 1H), 2.27-2.20 (m, 1H), 2.21 (s, 3H), 2.19-2.12 (m, 1H), 2.08-1.77 (m, 4H), 1.77-1.65 (m, 1H), 1.65-1.46 (m,8H).

EXAMPLE 8

(R)-1-[(3-Fluoro-phenylcarbamoyl)-methyl]-3-(1-thiophen-2-yl-cycloheptanecarbonyloxy)-1-azonia-bicyclo[2.2.2]octane bromide a) 2-Bromo-N-(3-fluoro-phenyl)-acetamide

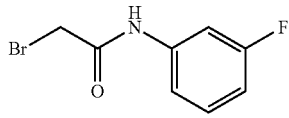

To a suspension of sodium bicarbonate (1 g) and 3-fluoroaniline (0.46 g) in dichloromethane (100 mL) was added 2-bromoacetyl bromide (0.36 mL) by dropwise addition. After stirring overnight the reaction mixture was washed with water, dried with magnesium sulfate and evaporated to yield the sub-titled compound (1.07 g).

m/e 232 [M+H$^+$]

$^1$H NMR (300 MHz, CDCl$_3$) δ 8.14 (s, 1H), 7.50 (dt, 1H), 7.31 (td, 1H), 7.18 (ddd, 1H), 6.87 (tdd, 1H), 4.03 (s, 2H).

EXAMPLE 8

(R)-1-[(3-Fluoro-phenylcarbamoyl)-methyl]-3-(1-thiophen-2-yl-cycloheptanecarbonyloxy)-1-azonia-bicyclo[2.2.2]octane bromide

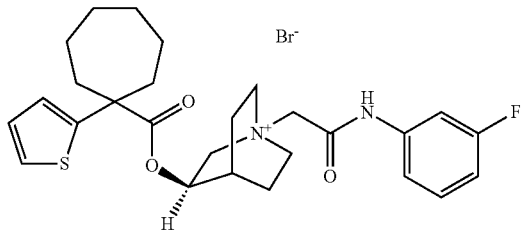

1-Thiophen-2-yl-cycloheptanecarboxylic acid (R)-(1-azabicyclo[2.2.2]oct-3-yl)ester (Example 5d) (96 mg) and 2-bromo-N-(3-fluoro-phenyl)-acetamide (Example 8a) (67 mg) were dissolved in acetonitrile (2 mL) and left overnight. Diethyl ether (10 mL) and isohexane (8 mL) were added and the mixture was left overnight. The resulting crystals were filtered off and washed with diethyl ether to afford the titled compound (90 mg).

m/e 485 [M$^+$]

$^1$H NMR (400 MHz, DMSO-D$_6$) δ 10.84 (s, 1H), 7.58 (dt, 1H), 7.46-7.39 (m, 2H), 7.33-7.29 (m, 1H), 7.04 (dd, 1H), 7.02-6.96 (m, 2H), 5.15-5.10 (m, 1H), 4.33-4.24 (m, 2H), 4.17-4.07 (m, 1H), 3.77-3.58 (m, 4H), 3.51 (dd, 1H), 2.56-2.44 (m, 1H), 2.28-2.22 (m,1H), 2.21-2.12 (m, 1H), 2.08-1.70 (m, 6H), 1.66-1.47 (m, 8H).

EXAMPLE 9

(R)-1-[(5-Methyl-pyrazin-2-ylcarbamoyl)-methyl]-3-(1-thiophen-2-yl cycloheptanecarbonyloxy)-1-azonia-bicyclo[2.2.2]octane bromide a) 2-Bromo-N-(5-methyl-pyrazin-2-yl)-acetamide

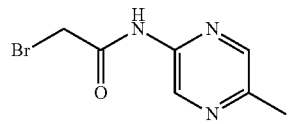

To a mixture of 5-methyl-pyrazin-2-ylamine and cesium carbonate (11.2 g) dissolved in dry DMF (30 mL) was added by dropwise addition bromoacetylbromide (2.89 g) and the mixture stirred at rt for 2 hours. Water (200 mL) was added and the mixture extracted with ethyl acetate (2×100 mL) and dried over magnesium sulfate. Concentration of the extract to ~50 mL and addition of isohexane (100 mL) gave the sub-titled compound as a solid (1.64 g).

$^1$H NMR (400 MHz, DMSO-D$_6$) δ 11.06 (1H, s), 9.17 (1H, s), 8.31 (1H, d), 4.16 (2H, s), 2.46 (3H, s).

EXAMPLE 9

(R)-1-[(5-Methyl-pyrazin-2-ylcarbamoyl)-methyl]-3-(1-thiophen-2-yl-cycloheptanecarbonyloxy)-1-azonia-bicyclo[2.2.2]octane bromide

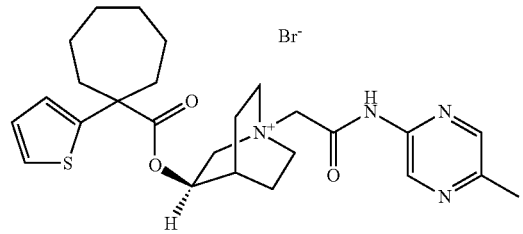

1-Thiophen-2-yl-cycloheptanecarboxylic acid (R)-(1-azabicyclo[2.2.2]oct-3-yl)ester (Example 5d) (48 mg) was dissolved in acetonitrile (2 mL) and 2-bromo-N-(5-methyl-pyrazin-2-yl)-acetamide (Example 9a) (33 mg) was added. After stirring for 1 week diethyl ether (8 mL) and isohexane (5 mL) were added. The crystals were collected by filtration, washed with ethyl acetate (2×4 mL) and dried to afford the titled compound (26 mg).

m/e 483 [M$^+$]

$^1$H NMR (400 MHz, DMSO-D$_6$) δ 11.26 (s, 1H), 9.15 (s, 1H), 8.36 (s, 1H), 7.44 (dd, 1H), 7.04 (dd, 1H), 6.99 (dd, 1H), 5.15-5.08 (m, 1H), 4.33 (s, 2H), 4.13 (ddd, 1H), 3.75-3.57 (m, 4H), 3.56-3.46 (m, 1H), 2.48 (s, 3H), 2.50-2.44 (m, 1H), 2.28-2.22 (m, 1H), 2.20-2.11 (m, 1H), 2.08-1.90 (m, 4H), 1.90-1.80 (m, 1H), 1.79-1.69 (m, 1H), 1.64-1.48 (m, 8H).

EXAMPLE 10

(R)-1-(Benzo[d]isoxazol-3-ylcarbamoylmethyl)-3-(1-thiophen-2-yl-cycloheptanecarbonyloxy)-1-azonia-bicyclo[2.2.2]octane chloride

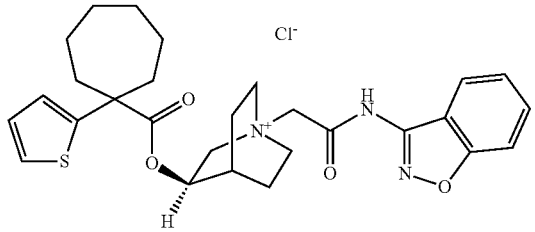

1-Thiophen-2-yl-cycloheptanecarboxylic acid (R)-(1-azabicyclo[2.2.2]oct-3-yl)ester (Example 5d) (71 mg) and N-benzo[d]isoxazol-3-yl-2-chloro-acetamide (Example 4a) (54 mg) were dissolved in acetonitrile (10 mL) and left to stand for 6 days. The resulting crystals were filtered off and washed with diethyl ether (3×10 mL) to afford the titled compound (82 mg).

m/e 509 [M+]

$^1$H NMR (400 MHz, DMSO-D$_6$) δ 12.16 (s, 1H), 8.17 (d, 1H), 7.74 (d, 1H), 7.72-7.67 (m, 1H), 7.44-7.39 (m, 2H), 7.04 (dd, 1H), 6.98 (dd, 1H), 5.16-5.11 (m, 1H), 4.64-4.50 (m, 2H), 4.21-4.13 (m, 1H), 3.82-3.64 (m, 4H), 3.59 (dd, 1H), 2.56-2.44 (m, 2H), 2.29-2.22 (m, 1H), 2.22-2.13 (m, 1H), 2.08-1.89 (m, 3H), 1.89-1.81 (m, 1H), 1.80-1.69 (m, 1H), 1.64-1.47 (m, 8H).

EXAMPLE 11

(R)-1-(Pyrazin-2-ylcarbamoylmethyl)-3-(1-thiophen-2-yl-cycloheptanecarbonyloxy)-1-azonia-bicyclo[2.2.2]octane bromide a) 2-Bromo-N-pyrazin-2-yl-acetamide

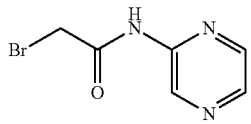

To a stirred suspension of pyrazin-2-ylamine (1.87 g) and potassium carbonate (8.19 g) in dichloromethane (25 mL) was added by dropwise addition 2-bromoacetyl bromide (1.72 mL). The reaction mixture was stirred overnight and then washed with water (2×50 mL). The organic phase was separated, dried with magnesium sulfate and evaporated to yield the sub-titled compound (0.70 g).

$^1$H NMR (400 MHz, CDCl$_3$) δ 9.51 (d, 1H), 8.63 (s, 1H), 8.42 (d, 1H), 8.30 (dd, 1H), 4.06 (s, 2H).

EXAMPLE 11

(R)-1-(Pyrazin-2-ylcarbamoylmethyl)-3-(1-thiophen-2-yl-cycloheptanecarbonyloxy)-1-azonia-bicyclo[2.2.2]octane bromide

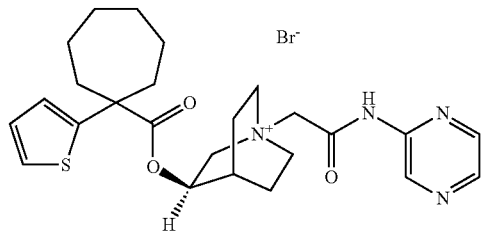

1-Thiophen-2-yl-cycloheptanecarboxylic acid (R)-(1-azabicyclo[2.2.2]oct-3-yl)ester (Example 5d) (116 mg) and 2-bromo-N-pyrazin-2-yl-acetamide (Example 11a) (75 mg) were dissolved in acetonitrile (2 mL) and left overnight. Diethyl ether (10 mL) and isohexane (8 mL) were added and the mixture was left to stand overnight. The resulting crystals were filtered off and washed with diethyl ether to afford the titled compound (117 mg).

m/e 469 [M+]

$^1$H NMR (400 MHz, DMSO-D$_6$) δ 11.38 (s, 1H), 9.28 (s, 1H), 8.50-8.45 (m, 2H), 7.44 (dd, 1H), 7.04 (dd, 1H), 6.99 (dd, 1H), 5.15-5.09 (m, 1H), 4.36 (s, 2H), 4.18-4.08 (m, 1H), 3.76-3.58 (m, 4H), 3.58-3.46 (m, 1H), 3.33-3.29 (m, 1H), 2.55-2.43 (m, 1H), 2.29-2.22 (m, 1H), 2.21-2.12 (m, 1H), 2.08-1.88 (m, 3H), 1.88-1.79 (m, 1H), 1.79-1.72 (m, 1H), 1.64-1.48 (m, 8H).

EXAMPLE 12

(R)-3-[1-(3-Fluoro-phenyl)-cycloheptanecarbonyloxy]-1-(pyrazin-2-ylcarbamoylmethyl)-1-azoniabicyclo[2.2.2]octane bromide a) 2-But-3-enyl-2-(3-fluoro-phenyl)-hex-5-enoic acid methyl ester

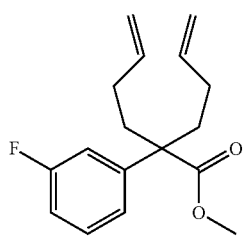

(3-Fluoro-phenyl)-acetic acid methyl ester (4.30 g) was dissolved in tetrahydrofuran (20 mL) and cooled to −78° C. Lithium bis(trimethylsilyl)amide (25.6 mL, 1M THF solution) was added and the solution was stirred for 30 minutes. 4-Bromo-but-1-ene (2.60 mL) was added and the reaction contents were allowed to warm to room temperature and stir for an hour. The reaction mixture was again cooled to −78° C.

Lithium bis(trimethylsilyl)amide (25.6 mL, 1M THF solution) was added and the solution was stirred for 30 minutes. 4-Bromo-1-butene (2.60 mL) was added and the reaction mixture was allowed to warm to room temperature and stir for an hour. The contents were again cooled to −78° C. and further aliquots of Lithium bis(trimethylsilyl)amide (25.6 mL, 1M THF solution) and 4-bromo-1-butene (2.60 mL) were added following the procedure outlined above. After stirring overnight, water (20 mL) was added and the reaction mixture extracted with diethyl ether (2×60 mL). The combined organic extracts were dried with magnesium sulfate and evaporated. The resulting liquid was purified by column chromatography on silica eluting with ethyl acetate/isohexane (1/99) to afford the sub-titled compound (5.0 g).

m/e 277 [M+H]⁺ b) 1-(3-Fluoro-phenyl)-cyclohept-4-enecarboxylic acid methyl ester

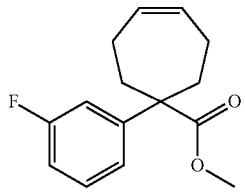

To 2-but-3-enyl-2-(3-fluoro-phenyl)-hex-5-enoic acid methyl ester (Example 12a) (5.0 g) in dichloromethane (100 mL) was added Grubbs Catalyst (2nd Generation, Sigma-Aldrich Company Ltd) (0.05 g). The mixture was warmed to reflux under nitrogen. After 20 hours the reaction was cooled to room temperature, evaporated to an oil and purified by column chromatography on silica eluting with ethyl acetate/isohexane (5/95) to yield an oil. Analysis of the product showed that significant amounts of starting material was present in the mixture so the mixture was subjected to a repetition of the reaction conditions and purification as above to afford the subtitled compound as a coloured oil (3.60 g).

m/e 249 [M+H]⁺ c) 1-(3-Fluoro-phenyl)-cycloheptanecarboxylic acid methyl ester

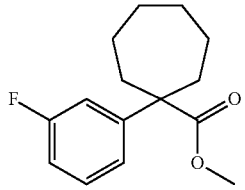

1-(3-Fluoro-phenyl)-cyclohept-4-enecarboxylic acid methyl ester (Example 12b) (1.09 g) was dissolved in methanol (20 mL), palladium on carbon (50 mg) added and mixture stirred under 4 atm of hydrogen overnight. The solution was filtered and evaporated to afford the sub-titled compound (1.09 g).

m/e 251 [M+H]⁺ d) 1-(3-Fluoro-phenyl)-cycloheptanecarboxylic acid (R)-(1-aza-bicyclo[2.2.2]oct-3-yl) ester

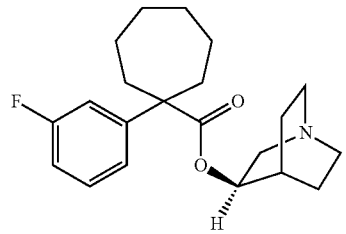

1-(3-Fluoro-phenyl)-cycloheptanecarboxylic acid methyl ester (Example 12c) (0.280 g) was dissolved in toluene (100 mL) and (R)-quinuclidin-3-ol (0.320 g) was added. Toluene (10 mL) was distilled off in a Dean and Stark apparatus and after cooling sodium hydride (10 mg) was added. The reaction was refluxed in a Dean and Stark apparatus for 4 hours after which time an extra amount of sodium hydride (10 mg) was added and the reaction was heated to reflux for a further 4 hours. After allowing to cool to room temperature, the toluene was washed with water, dried (MgSO₄) and evaporated. The residue was purified by column chromatography eluting with ethyl acetate/isohexane/triethylamine (50/50/ 1) then ethyl acetate/triethylamine (99/1) to afford the sub-titled compound (0.200 g m/e 346 [M+H]⁺

¹H NMR (399.824 MHz, CDCl₃) δ 7.26 (td, 1H), 7.10-7.07 (m, 1H), 7.04 (dd, 1H), 6.90 (ddd, 1H), 4.78-4.73 (m, 1H), 3.14 (ddd, 1H), 2.79-2.66 (m, 3H), 2.66-2.56 (m, 1H), 2.53-2.46 (m, 1H), 2.46-2.36 (m, 2H), 2.13-1.99 (m, 2H), 1.90-1.85 (m, 1H), 1.73-1.40 (m, 11H), 1.29-1.18 (m, 1H).

EXAMPLE 12

(R)-3-[1-(3-Fluoro-phenyl)-cycloheptanecarbonyloxy]-1-(pyrazin-2-ylcarbamoylmethyl)-1-azoniabicyclo[2.2.2]octane bromide

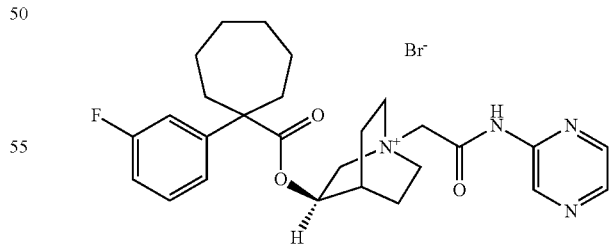

1-(3-Fluoro-phenyl)-cycloheptanecarboxylic acid (R)-(1-aza-bicyclo[2.2.2]oct-3-yl)ester (Example 12d) (0.100 g) was dissolved in acetonitrile (8 mL) and 2-bromo-N-pyrazin-2-yl-acetamide (Example 11a) (0.05 g) was added. The reaction mixture was stirred for 3 days diluted with diethyl ether (8 mL), stirred for a further 10 minutes, the resulting solid was filtered and washed with diethyl ether (3×8 mL) to afford a solid which was recrystallised from hot butanone (8 mL) to afford the titled compound as a solid (0.081 g).

m/e 481 [M+]

$^1$NMR (399.826 MHz, DMSO-D$_6$) δ 11.42 (s, 1H), 9.28 (s, 1H), 8.49-8.45 (m, 2H), 7.40 (td, 1H), 7.19-7.12 (m, 2H), 7.09 (td, 1H), 5.17-5.10 (m, 1H), 4.40-4.30 (m, 2H), 4.16-4.07 (m, 1H), 3.71-3.57 (m, 4H), 3.52-3.41 (m, 1H), 2.43-2.27 (m, 2H), 2.26-2.19 (m, 1H), 2.19-2.09 (m, 1H), 2.05-1.87 (m, 3H), 1.86-1.76 (m, 1H), 1.71-1.46(m, 9H).

EXAMPLE 13

(R)-3-[1-(3-Fluoro-phenyl)-cycloheptanecarbonyloxy]-1-(isoxazol-3-ylcarbamoylmethyl)-1-azonia-bicyclo[2.2.2]octane bromide a) 2-Bromo-N-isoxazol-3-yl-acetamide

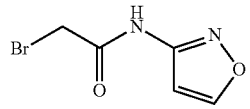

Isoxazol-3-ylamine (1.14 g) was dissolved in dichloromethane (50 mL) and potassium carbonate (3.74 g) was added. Bromoacetyl chloride (1.12 mL) was added slowly with stirring and the suspension was stirred overnight. The reaction mixture was washed with water (2×50 mL), dried and evaporated. The product was recrystallised from dichloromethane/isohexane to afford the sub-titled compound (2.3 g).

$^1$H NMR (299.946 MHz, CDCl$_3$) δ 8.94 (s, 1H), 8.34 (s, 1H), 7.06 (s, 1H), 4.03 (s, 2H).

EXAMPLE 13

(R)-3-[1-(3-Fluoro-phenyl)-cycloheptanecarbonyloxy]-1-(isoxazol-3-ylcarbamoylmethyl)-1-azonia-bicyclo[2.2.2]octane bromide

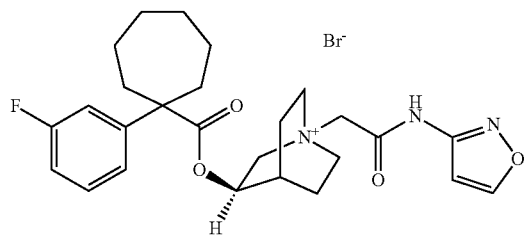

1-(3-Fluoro-phenyl)-cycloheptanecarboxylic acid (R)-(1-aza-bicyclo[2.2.2]oct-3-yl)ester (Example 12d) (50 mg) and 2-bromo-N-isoxazol-3-yl-acetamide (Example 13a) (30 mg) were dissolved in acetonitrile (4 mL) and stirred overnight. The solution was diluted with diethyl ether (12 mL) and stirred overnight. The resulting crystals were filtered off, washed with ether (3×10 mL) and dried to afford the titled compound as a solid (48 mg).

m/e 470 [M+]

$^1$H NMR (399.826 MHz, DMSO-D$_6$) δ 11.69 (s, 1H), 8.90 (d, 1H), 7.40 (td, 1H), 7.18-7.07 (m, 3H), 6.91 (d, 1H), 5.16-5.10 (m, 1H), 4.31 (d, 1H), 4.25 (d, 1H), 4.09 (ddd, 1H), 3.68-3.53 (m, 4H), 3.43 (dd, 1H), 2.42-2.27 (m, 2H), 2.25-2.19 (m, 1H), 2.18-2.09 (m, 1H), 2.04-1.88 (m, 3H), 1.85-1.75 (m, 1H), 1.69-1.51 (m, 9H).

EXAMPLE 14

(R)-3-(1-Phenyl-cycloheptanecarbonyloxy)-1-(pyridin-2-ylcarbamoylmethyl)-1-azonia-bicyclo[2.2.2] octane chloride a) Cycloheptyl-phenyl-methanone

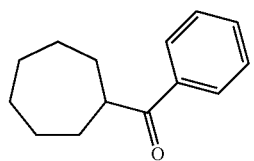

Phenylmagnesium bromide (3.0M solution in diethyl ether) (271 mL), was added dropwise to a stirred (overhead stirrer) solution of cycloheptanecarbonitrile (50 g) in 229 mL diethyl ether under nitrogen at such a rate as to maintain gentle reflux. The reaction mixture was then heated at reflux for 3 hours. TLC indicated no starting material present in the reaction mixture. The reaction mixture was allowed to cool to room temperature and stood under nitrogen overnight. The reaction mixture was cooled to 0° C. and treated dropwise with 102 mL 4N HCl(aq) keeping the temperature below 20° C. 4N sulfuric acid (203 mL) was added dropwise rapidly to start with and then more slowly towards the end. The ice bath was removed and the diethyl ether was distilled off. The reaction mixture was heated at 80-90° C. for 3.5 hours then allowed to cool to room temperature and stood overnight. The mixture was diluted with ether (approx 450 mL) and water (100 mL). The layers were separated and the aqueous layer was extracted with ether (2×400 mL). The organic layers were combined and washed with saturated aqueous sodium hydrogen carbonate (600 mL) and brine (600 mL), dried over magnesium sulphate, filtered and evaporated to give the sub-titled compound as an orange liquid (86.5 g).

$^1$H NMR (300 MHz, CDCl$_3$) δ 7.96-7.91 (d, 2H), 7.54-7.49 (m, 1H), 7.48-7.40 (t, 2H), 3.48-3.37 (m, 1H), 1.98-1.88 (m, 2H), 1.85-1.44 (m, 10H).

b) (1-Chloro-cycloheptyl)-phenyl-methanone

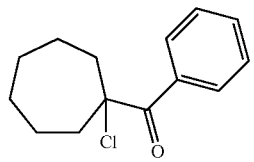

Sulfuryl chloride (210 mL) was added dropwise to neat cycloheptyl-phenyl-methanone (Example 14a) (86.5 g) at 0° C. over approximately 1 hour. Gas evolution and an exotherm were observed. The internal temperature was kept below 15° C. during the addition and the evolved gas was scrubbed by passing through a 10.2M aqueous solution of NaOH. The reaction mixture was heated to reflux overnight. The reaction mixture was cooled to 0° C and poured slowly onto ice (1 L)

with stirring. The layers were separated and the aqueous layer was extracted with ether (2×400 mL). The combined organic layers were washed with water (600 mL), saturated aqueous sodium hydrogen carbonate (600 mL), and brine (600 mL), dried over magnesium sulphate, filtered and evaporate to give the sub-titled compound as a brown oil (100 g).

$^1$H NMR (400 MHz, CDCl$_3$) δ 8.10-8.06 (d, 2H), 7.52-7.46 (t, 1H), 7.44-7.36 (t, 2H), 2.50 (ddd, 2H), 2.29 (ddd, 2H), 1.84-1.73 (m, 2H), 1.68-1.58 (m, 2H), 1.58-1.43 (m, 4H).

c) 1-Phenyl-cycloheptanecarboxylic acid

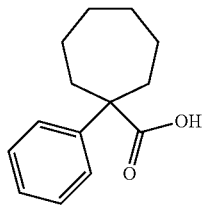

A solution of (1-chloro-cycloheptyl)-phenyl-methanone (Example 14b) (100 g) in 750 mL dioxane was treated dropwise rapidly with a cloudy solution of silver nitrate (137 g) in water (85 mL) causing a precipitate to form. The reaction mixture was heated to 75° C. for 4.5 hours. The reaction mixture was cooled to room temperature then filtered and concentrated to approximately 200 mL. Water (200 mL) and ether (300 mL) were added and the layers separated. The aqueous layer was extracted with ether (2×250 mL). The combined organic layers were extracted with 10% aqueous sodium carbonate (3×250 mL). The mL). The combined basic extracts were heated to 90° C. over 40 minutes and then cooled to room temperature and acidified with concentrated HCl (aq). The resulting brown solid was filtered off, washed with water (×2) and dried under vacuum at 50° C. Crystallisation from hot ethanol (40 mL) gave the sub-titled compound as pale brown crystals (9.83 g).

$^1$H NMR (400 MHz, CD$_3$OD) δ 7.36-7.26 (m, 4H), 7.21-7.15 (m, 1H), 2.43-2.35 (m, 2H), 2.07-1.98 (m, 2H), 1.70-1.53 (m, 8H).

d) 1-Phenyl-cycloheptanecarboxylic acid methyl ester

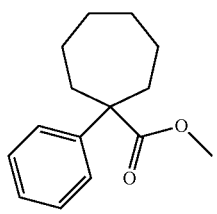

A 2.0 M solution of trimethylsilyl diazomethane (29.2 mL) was added dropwise to a solution of 1-phenyl-cycloheptanecarboxylic acid (Example 14c) (9.8 g) in methanol (85 mL) and toluene (300 mL) under an atmosphere of nitrogen. After 45 minutes the reaction mixture was concentrated under vacuum and the crude product was purified by column chromotography eluting with 0-10% ethyl acetate/cyclohexane to give the product as a pale yellow oil (9.25 g).

$^1$H NMR (300 MHz, CD$_3$OD) δ 7.32-7.24 (m, 4H), 7.21-7.12 (m, 1H), 3.60 (s, 3H), 2.43-2.32 (m, 2H), 2.07-1.96 (m, 2H), 1.65-1.58 (m, 8H).

e) 1-Phenyl-cycloheptanecarboxylic acid (R)-(1-azabicyclo[2.2.2]oct-3-yl)ester

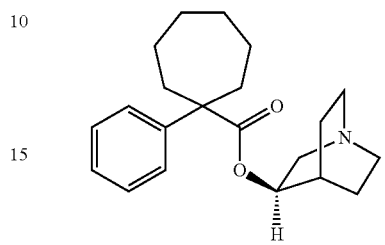

A solution of (R)-(3)-quinuclidinol (10.13 g) and 1-phenyl-cycloheptanecarboxylic acid methyl ester (Example 14d) (9.25 g) in toluene (90 mL) was heated to reflux with a Dean-Stark trap for 30 min. The reaction mixture was allowed to cool to room temperature and the trap was removed. Sodium hydride (60% dispersion in mineral oil) (3.19 g) was added portionwise under nitrogen and the reaction mixture was heated to reflux overnight under nitrogen. The reaction mixture was cooled in an ice bath and diluted with ethyl acetate (200 mL) and water (200 mL). The mixture was filtered and the layers separated. The aqueous layer was extracted with ethyl acetate (2×250 mL) and the combined organic layers were washed with brine, dried over magnesium sulfate and evaporated to give the crude product which was purified by silica gel chromatography eluting with EtOAc containing 1% triethylamine to give the sub-titled compound as a colourless oil (7.63 g)

$^1$H NMR (400 MHz, CD$_3$OD) δ 7.34-7.28 (m, 4H), 7.23-7.17 (m, 1H), 4.80-4.75 (m, 1H), 3.12 (ddd, 1H), 2.75-2.65 (m, 3H), 2.53-2.37 (m, 4H), 2.14-2.06 (m, 2H), 1.88-1.85 (m, 1H), 1.69-1.54 (m, 10H), 1.54-1.42 (m, 1H), 1.35-1.24 (m, 1H).

f) 2-Chloro-N-pyridin-2-yl-acetamide

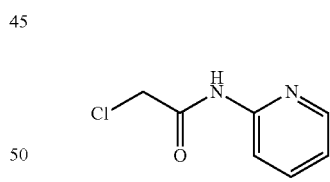

A solution of 2-amino-pyridine (1.0 g) in dry dichloromethane (10.6 mL) under nitrogen at 0° C. was treated with triethylamine (1.63 mL) followed by slow addition of chloroacetyl chloride (0.93 mL). The reaction mixture was allowed to warm up to room temperature. After 2 hours, the mixture was partitioned between dichloromethane and water. The phases were separated and the aqueous layer was extracted with dichloromethane (×2). The combined organic layers were washed with brine, dried over magnesium sulphate, filtered and concentrated to give the crude product which was purified by silica gel chromatography eluting with 0-30% ethyl acetate/cyclohexane to give the title compound (1.43 g) as a pink solid. Further purification was achieved by trituration with 40-60 petroleum ether to give 1.15 g of the desired product. Crystallisation of a 0.94 g portion of the material from refluxing acetonitrile (2.4 mL) gave the subtitled compound as a pink solid (0.73 g).

$^1$H NMR (400 MHz, CDCl$_3$): δ 8.96 (s, 1H), 8.32 (ddd, 1H), 8.21 (d, 1H), 7.76 (ddd, 1H), 7.12 (ddd, 1H), 4.20 (s, 2H).

EXAMPLE 14

(R)-3-(1-Phenyl-cycloheptanecarbonyloxy)-1-(pyridin-2-ylcarbamoylmethyl)-1-azonia-bicyclo[2.2.2]octane chloride

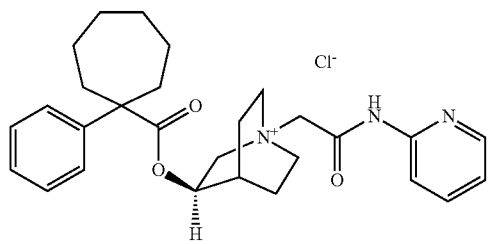

A solution of 1-phenyl-cycloheptanecarboxylic acid (R)-(1-aza-bicyclo[2.2.2]oct-3-yl) ester (Example 14e) (254 mg) in acetonitrile (5 mL) was treated with 2-chloro-N-pyridin-2-yl-acetamide (Example 14f) (146 mg) and the resulting yellow solution was stirred at room temperature overnight during which time a solid precipitated. The reaction mixture was treated with ~2 mL of ether and the solid was filtered off, washed with ether and dried under vacuum to give the title compound as an off-white solid (217 mg). Crystallisation from refluxing acetonitrile (20 mL) gave 98 mg of the titled compound as a white crystalline solid.

m/e 462 [M]$^+$ $^1$H NMR (400 MHz, DMSO-D$_6$): δ 11.09 (s, 1H), 8.34-8.32 (d, 1H), 7.97 (d, 1H), 7.85-7.79 (t, 1H), 7.33-7.25 (m, 4H), 7.21-7.13 (m, 2H), 5.07 (m, 1H), 4.29 (s, 2H), 4.07 (ddd, 1H), 3.65-3.51 (m, 4H), 3.41-3.29 (m, 1H), 2.36-2.23 (m, 2H), 2.17-2.04 (m, 2H), 1.99-1.81 (m, 3H), 1.78-1.66 (m, 1H), 1.77-1.19 (m, 9H).

Preparation of Example 14

(R)-3-(1-Phenyl-cycloheptanecarbonyloxy)-1-(pyridin-2-ylcarbamoylmethyl)-1-azonia-bicyclo[2.2.2]octane chloride Crystalline Form A A solution of 1-phenyl-cycloheptanecarboxylic acid (R)-(1-aza-bicyclo[2.2.2]oct-3-yl) ester (Example 14e) (254 mg, 0.78 mmol) in acetonitrile (5 mL) was treated with 2-chloro-N-pyridin-2-yl-acetamide (Example 14f) (146 mg) and the resulting yellow solution was stirred at room temperature overnight during which a solid precipitated. The reaction mixture was treated with a couple of mLs of ether and the solid was filtered off, washed with ether and dried under vacuum to give the title compound (217 mg) as an off-white solid. Crystallisation from refluxing acetonitrile (20 mL) gave 98 mg of the title compound as a white crystalline solid.

m/e 462 [M]$^+$ $^1$H NMR (400 MHz, DMSO-D$_6$): δ 11.09 (s, 1H), 8.34-8.32 (d, 1H), 7.97 (d, 1H), 7.85-7.79 (t, 1H), 7.33-7.25 (m, 4H), 7.21-7.13 (m, 2H), 5.07 (m, 1H), 4.29 (s, 2H), 4.07 (ddd, 1H), 3.65-3.51 (m, 4H), 3.41-3.29 (m, 1H), 2.36-2.23 (m, 2H), 2.17-2.04 (m, 2H), 1.99-1.81 (m, 3H), 1.78-1.66 (m, 1H), 1.77-1.19 (m, 9H).

Analysis of Example 14

(R)-3-(1-Phenyl-cycloheptanecarbonyloxy)-1-(pyridin-2-ylcarbamoylmethyl)-1-azonia-bicyclo[2.2.2]octane chloride Crystalline Form A A sample of crystalline Example 14 Crystalline Form A obtained by the procedure described above was analysed by XRPD (PANalytical X'Pert system), DSC and TGA.

The melting temperature of Example 14 chloride Form A as determined by DSC was found to be 239° C. (onset) (±2° C.). Weight loss observed prior to melting by TGA was negligible GVS determination gave a negligible weight increase (% w/w) at 80% RH (±0.2%).

An XRPD spectrum of Example 14 chloride Form A is presented in FIG. 1.

EXAMPLE 15

(R)-3-(1-Phenyl-cycloheptanecarbonyloxy)-1-(pyridin-2-ylcarbamoylmethyl)-1-azonia-bicyclo[2.2.2]octane bromide a) 2-Bromo-N-pyridin-2-yl-acetamide

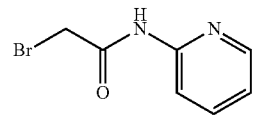

To a solution of 2-aminopyridine (48.8 mmol) in anhydrous THF (98 mL) at room temperature was added Et$_3$N (58.6 mmol) and bromoacetyl bromide (58.6 mmol) dropwise The mixture was stirred overnight and quenched with sat. NaHCO$_{3\ (aq)}$. EtOAc was added to the mixture and the layers separated. The aqueous phase was extracted with EtOAc and the combined organics dried (MgSO$_4$) and concentrated in vacuo to a brown solid.

Purification by flash silica gel chromatography eluting with 1-2% MeOH/dichloromethane gave the sub-titled compound as a yellow solid (1.14 g).

$^1$H NMR (400 MHz, CDCl$_3$): δ 8.75 (s, 1H), 8.26 (ddd, 1H), 8.10 (d, 1H), 7.67 (ddd, 1H), 7.03 (ddd, 1H), 3.94 (s, 2H).

EXAMPLE 15

(R)-3-(1-Phenyl-cycloheptanecarbonyloxy)-1-(pyridin-2-ylcarbamoylmethyl)-1-azonia-bicyclo[2.2.2]octane bromide

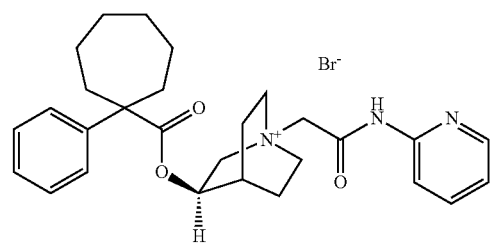

1-Phenyl-cycloheptanecarboxylic acid (R)-(1-aza-bicyclo[2.2.2]oct-3-yl)ester (Example 14e) (0.79 mmol) and 2-bromo-N-pyridin-2-yl-acetamide (Example 15a) (0.87 mmol) were stirred together in anhydrous MeCN at room temperature for 2.5 days. The reaction mixture was concentrated in vacuo and the yellow solid purified by flash silica gel column chromatography eluting with 2-8% MeOH/dichloromethane to give a tan solid which crystallised from boiling MeCN to give the titled compound as a white solid (211 mg).

m/e 462 [M]$^+$ $^1$H NMR (400 MHz, DMSO-D$_6$) δ 11.02 (s, 1H), 8.33 (ddd, 1H), 7.97 (d, 1H), 7.86-7.80 (m, 1H), 7.32-7.25 (m, 4H), 7.23-7.12 (m, 2H), 5.09-5.04 (m, 1H), 4.23 (s, 2H), 4.06 (ddd, 1H), 3.63-3.49 (m, 4H), 3.41-3.29 (m, 1H), 2.37-2.22 (m, 2H), 2.17-2.04 (m, 2H), 1.98-1.83 (m, 3H), 1.78-1.66 (m, 1H), 1.65-1.39 (m, 9H).

Preparation of Example 15

(R)-3-(1-Phenyl-cycloheptanecarbonyloxy)-1-(pyridin-2-ylcarbamoylmethyl)-1-azonia-bicyclo[2.2.2]octane bromide Crystalline Form A 1-Phenyl-cycloheptanecarboxylic acid (R)-(1-aza-bicyclo[2.2.2]oct-3-yl)ester (Example 14e) (0.79 mmol) and 2-bromo-N-pyridin-2-yl-acetamide (Example 15a) (0.87 mmol) were stirred together in anhydrous MeCN at room temperature for 2.5 days. The reaction mixture was concentrated in vacuo and the yellow solid purified by flash silica gel column chromatography eluting with 2-8% MeOH/dichloromethane to give a tan solid. The solid was dissolved up in refluxing MeCN and the solution was allowed to cool down to room temperature. The resulting crystals were filtered off and washed with a small quantity of cold MeCN to give the title compound (211 mg) as a white crystalline solid.

m/e 462 [M]$^+$ $^1$H NMR (400 MHz, DMSO-D$_6$): δ 11.02 (s, 1H), 8.33 (ddd, 1H), 7.97 (d, 1H), 7.86-7.80 (m, 1H), 7.32-7.25 (m, 4H), 7.23-7.12 (m, 2H), 5.09-5.04 (m, 1H), 4.23 (s, 2H), 4.06 (ddd, 1H), 3.63-3.49 (m, 4H), 3.41-3.29 (m, 1H), 2.37-2.22 (m, 2H), 2.17-2.04 (m, 2H), 1.98-1.83 (m, 3H), 1.78-1.66 (m, 1H), 1.65-1.39 (m, 9H).

Analysis of Example 15

(R)-3-(1-Phenyl-cycloheptanecarbonyloxy)-1-(pyridin-2-ylcarbamoylmethyl)-1-azonia-bicyclo[2.2.2]octane bromide Crystalline Form A A sample of crystalline Example 15 Crystalline Form A obtained by the procedure described above was analysed by XRPD (PANalytical X'Pert system), DSC and TGA.

The melting temperature of Example 15 bromide Form A as determined by DSC was found to be 230° C. (onset) (±2° C.). Weight loss observed prior to melting by TGA was negligible. GVS determination gave a negligible weight increase (% w/w) at 80% RH (±0.2%).

An XRPD spectrum of Example 15 bromide Form A is presented in FIG. 2.

EXAMPLE 16

(R)-3-(1-Phenyl-cycloheptanecarbonyloxy)-1-(pyridin-4 ylcarbamoylmethyl)-1-azonia-bicyclo[2.2.2]octane chloride a) 2-Chloro-N-pyridin-4-yl-acetamide

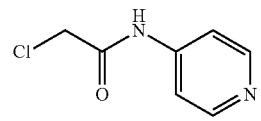

A suspension of 4-aminopyridine (0.96 g) in dry dichloromethane (10 mL) under nitrogen was cooled to 0° C. in an ice bath. Triethylamine (1.56 mL) was added, followed by the slow addition of chloroacetyl chloride (0.89 mL). The ice bath was removed and the reaction mixture allowed to reach room temperature. The reaction mixture was diluted with water (20 mL) and dichloromethane (25 mL). The solid was filtered off, washed with pentane and dried to give the title compound as a brown solid (0.87 g). The layers of the filtrate were separated and the organic layer was washed with water, dried and the solvent was evaporated to give a dark brown glass. Trituration with pentane gave another batch of the title compound (0.91 g).

$^1$H NMR (400 MHz, DMSO-D$_6$) δ 10.79 (s, 1H), 8.47 (d, 2H), 7.59 (d, 2H), 4.33 (s, 2H)

EXAMPLE 16

(R)-3-(1-Phenyl-cycloheptanecarbonyloxy)-1-(pyridin-4-ylcarbamoylmethyl)-1-azonia-bicyclo[2.2.2]octane chloride

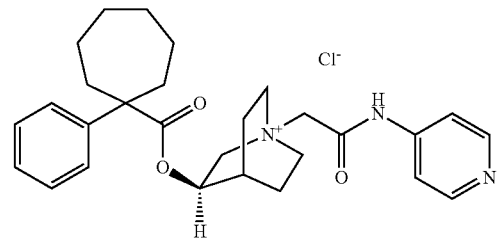

2-Chloro-N-pyridin-4-yl-acetamide (Example 16a) (30 mg) was added to a solution of 1-phenyl-cycloheptanecarboxylic acid (R)-(1-aza-bicyclo[2.2.2]oct-3-yl)ester (Example 14e) (53 mg) in acetonitrile (1 mL). The reaction mixture was stirred at room temperature for 24 h. Diethyl ether (2 mL) was added and the reaction mixture was filtered to give a light brown solid. The solid was washed several times with diethyl ether and dried under vacuum at 40° C. Purification by column chromatography eluting with 0-10% MeOH/ dichloromethane gave the title compound as a white solid (20 mg).

m/e 462 [M]$^+$ $^1$H NMR (400 MHz, DMSO-D$_6$) δ 11.34 (s, 1H), 8.46 (d, 2H), 7.55 (d, 2H), 7.34-7.26 (m, 4H), 7.22-7.17 (m, 1H), 5.08

(m, 1H), 4.30 (s, 2H), 4.11-4.02 (m, 1H), 3.65-3.51 (m, 4H), 3.42-3.30 (m, 1H), 2.38-2.24 (m, 2H), 2.17-2.06 (m, 2H), 1.99-1.84 (m, 3H), 1.79-1.67 (m, 1H), 1.69-1.26 (m, 9H).

EXAMPLE 17

(R)-1-[(5-Fluoro-pyridin-2-ylcarbamoyl)-methyl]-3-(1-phenyl-cycloheptanecarbonyloxy)-1-azonia-bicyclo[2.2.2]octane chloride a) 2-Chloro-N-(5-fluoro-pyridin-2-yl)-acetamide

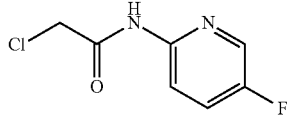

The title compound (0.99 g, 73%, white solid) was prepared according to the method used is in Example 14f but using 2-amino-5-fluoro-pyridine.
$^1$H NMR (400 MHz, DMSO-D$_6$) δ 10.91 (s, 1H), 8.35 (d, 1H), 8.10 (dd, 1H), 7.80-7.74 (m, 1H), 4.34 (s, 2H).

EXAMPLE 17

(R)-1-[(5-Fluoro-pyridin-2-ylcarbamoyl)-methyl]-3-(1-phenyl-cycloheptanecarbonyloxy)-1-azonia-bicyclo[2.2.2]octane chloride

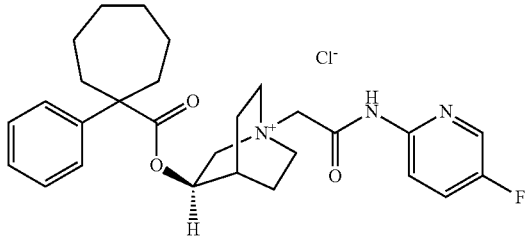

2-Chloro-N-(5-fluoro-pyridin-2-yl)-acetamide (Example 17a) (31 mg) was added to a solution of 1-phenyl-cycloheptanecarboxylic acid (R)-(1-aza-bicyclo[2.2.2]oct-3-yl)ester (Example 14e) (49 mg) in acetonitrile (1 mL). The reaction mixture was stirred at room temperature overnight. Diethyl ether (2 mL) was added to the reaction mixture and the white solid was filtered off, washed several times with diethyl ether and dried under vacuum at 40° C. to give the title compound (49 mg).
m/e 480 [M]$^+$
$^1$H NMR (400 MHz, DMSO-D$_6$) δ 11.19 (s, 1H), 8.36 (d, 1H), 8.02 (m, 1H), 7.81 (ddd, 1H), 7.33-7.26 (m, 4H), 7.22-7.17 (m, 1H), 5.07 (m, 1H), 4.26 (s, 2H), 4.11-4.03 (m, 1H), 3.64-3.50 (m, 4H), 3.41-3.29 (m, 1H), 2.36-2.23 (m, 2H), 2.17-2.05 (m, 2H), 1.99-1.82 (m, 3H), 1.78-1.65 (m, 1H), 1.70-1.41 (m, 9H).

EXAMPLE 18

(R)-1-[(5-Methyl-pyridin-2-ylcarbamoyl)-methyl]-3-(1-phenyl-cycloheptanecarbonyloxy)-1-azonia-bicyclo[2.2.2]octane chloride a) 2-Chloro-N-(5-methyl-pyridin-2-yl)-acetamide

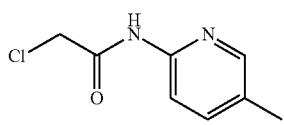

The title compound (0.50 g) was prepared according to the method used in Example 14f but using 2-amino-5-picoline.
$^1$H NMR (400 MHz, DMSO-D$_6$) δ 10.69 (s, 1H), 8.17 (dt, 1H), 7.95 (d, 1H), 7.63 (dd, 1H), 4.32 (s, 2H), 2.25 (s, 3H).

EXAMPLE 18

(R)-1-[(5-Methyl-pyridin-2-ylcarbamoyl)-methyl]-3-(1-phenyl-cycloheptanecarbonyloxy)-1-azonia-bicyclo[2.2.2]octane chloride

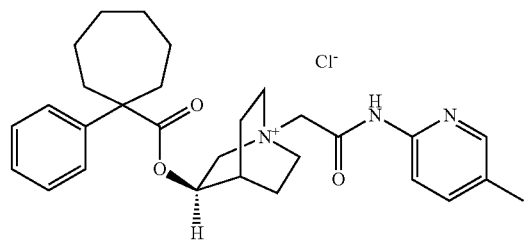

The title compound (36 mg) was prepared according to the method used to prepare Example 17 using 2-chloro-N-(5-methyl-pyridin-2-yl)-acetamide (Example 18a) in place of 2-chloro-N-(5-fluoro-pyridin-2-yl)-acetamide.
m/e 476 [M]$^+$
$^1$H NMR (400 MHz, DMSO-D$_6$) δ 10.98 (s, 1H), 8.17 (d, 1H), 7.88 (d, 1H), 7.65 (dd, 1H), 7.33-7.25 (m, 4H), 7.23-7.17 (m, 1H), 5.07 (m, 1H), 4.24 (s, 2H), 4.10-4.02 (m, 1H), 3.64-3.50 (m, 4H), 3.40-3.27 (m, 1H), 2.37-2.22 (m, 2H), 2.23 (s, 3H), 2.17-2.04 (m, 2H), 1.97-1.84 (m, 3H), 1.78-1.66 (m, 1H), 1.66-1.35 (m, 9H).

EXAMPLE 19

(R)-3-(1-Phenyl-cycloheptanecarbonyloxy)-1-(pyridin-3-ylcarbamoylmethyl)-1-azonia-bicyclo[2.2.2]octane chloride a) 2-Chloro-N-pyridin-3-yl-acetamide

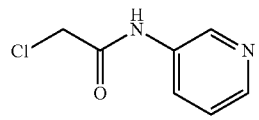

A mixture of 3-aminopyridine (350 mg) and sodium hydroxide (0.6 g) were dissolved in water (8 mL) and the reaction mixture was cooled in an ice bath. Chloroacetyl chloride (1.19 mL) was added dropwise and the reaction mixture was allowed to stir at room temperature overnight. The reaction mixture was extracted with dichloromethane and organic layer was concentrated and purified by column chromatography, eluting with 0-60% ethyl acetate/cyclohexane to give the title compound (0.10 g) as a white solid.

¹H NMR (400 MHz, DMSO-D₆) δ 10.51 (s, 1H), 8.73 (d, 1H), 8.30 (dd, 1H), 8.03 (ddd, 1H), 7.40-7.35 (m, 1H), 4.30 (s, 2H).

EXAMPLE 19

(R)-3-(1-Phenyl-cycloheptanecarbonyloxy)-1-(pyridin-3-ylcarbamoylmethyl)-1-azonia-bicyclo[2.2.2]octane chloride

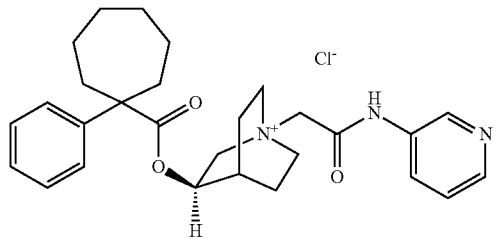

The title compound (78 mg) was prepared by an analogous method to that used in Example 15 using 2-chloro-N-pyridin-3-yl-acetamide in place of 2-bromo-N-pyridin-2-yl-acetamide.

m/e 462 [M]⁺

¹H NMR (400 MHz, DMSO-D₆) δ 11.27 (s, 1H), 8.76 (d, 1H), 8.30 (dd, 1H), 7.98 (ddd, 1H), 7.37 (ddd, 1H), 7.33-7.25 (m, 4H), 7.22-7.15 (m, 1H), 5.07 (d, 1H), 4.28 (dd, 2H), 4.11-4.03 (m, 1H), 3.65-3.50 (m, 4H), 3.41-3.29 (m, 1H), 2.37-2.21 (m, 2H), 2.19-2.05 (m, 2H), 1.97-1.83 (m, 3H), 1.78-1.66 (m, 1H), 1.71-1.27 (m, 9H).

EXAMPLE 20

(R)-1-[(2-Methyl-pyridin-4-ylcarbamoyl)-methyl]-3-(1-phenyl-cycloheptanecarbonyloxy)-1-azonia-bicyclo[2.2.2]octane chloride a) 2-Chloro-N-(2-methyl-pyridin-4-yl)-acetamide

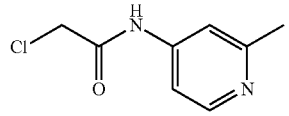

The title compound (1.0 g) was prepared according to the method used in Example 14f but using 4-amino-2-methylpyridine.

¹H NMR (400 MHz, DMSO-D₆) δ 10.64 (s, 1H), 8.32 (d, 1H), 7.44 (d, 1H), 7.38-7.35 (m, 1H), 4.30 (s, 2H), 2.42 (s, 3H).

EXAMPLE 20

(R)-1-[(2-Methyl-pyridin-4-ylcarbamoyl)-methyl]-3-(1-phenyl-cycloheptanecarbonyloxy)-1-azonia-bicyclo[2.2.2]octane chloride

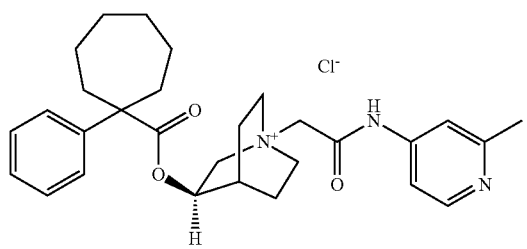

The title compound was prepared using an analogous procedure to that used to prepare Example 17. Further purification was achieved by silica gel chromatography eluting with 0-20% MeOH/dichloromethane to give the title compound as a white solid (57 mg).

m/e 476 [M]⁺

¹H NMR (400 MHz, DMSO-D₆) δ 11.32 (s, 1H), 8.31 (d, 1H), 7.43 (d, 1H), 7.35-7.26 (m, 5H), 7.22-7.16 (m, 1H), 5.09-5.04 (m, 1H), 4.30 (dd, 2H), 4.09-4.01 (m, 1H), 3.64-3.49 (m, 4H), 3.41-3.29 (m, 1H), 2.38 (s, 3H), 2.39-2.23 (m, 2H), 2.17-2.05 (m, 2H), 1.97-1.82 (m, 3H), 1.78-1.65 (m, 1H), 1.65-1.41 (m, 9H).

EXAMPLE 21

(R)-1-Phenylcarbamoylmethyl-3-(1-phenyl-cycloheptanecarbonyloxy)-1-azonia-bicyclo[2.2.2]octane bromide a) 2-Bromo-N-phenyl-acetamide

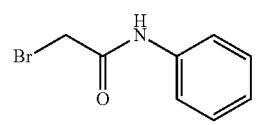

To a solution of bromoacetyl bromide (9.6 mL) and potassium carbonate (11.4 g) in dichloromethane (100 mL) was added aniline (5 mL) dropwise over 15-20 mins causing the reaction mixture to get warm and a white precipitate to form. After 4.5 h the reaction mixture was poured into water, shaken for several minutes and then the phases were separated. The organic layer was washed with water and concentrated to a smaller volume resulting in precipitation of a solid that was filtered off to give the sub-titled compound (970 mg) as a white solid.

¹H NMR (400 MHz, CDCl₃): δ 8.10 (s, 1H), 7.53 (d, 2H), 7.40-7.33 (m, 2H), 7.17 (t, 1H), 4.03 (s, 2H).

EXAMPLE 21

(R)-1-Phenylcarbamoylmethyl-3-(1-phenyl-cycloheptanecarbonyloxy)-1-azonia-bicyclo[2.2.2]octane bromide

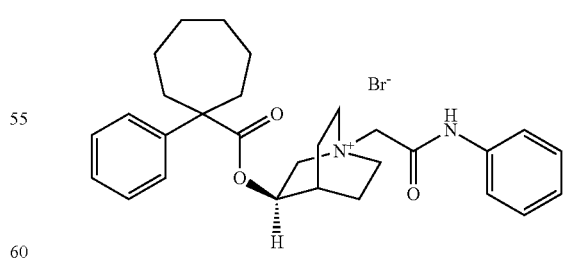

To 1-phenyl-cycloheptanecarboxylic acid (R)-(1-aza-bicyclo[2.2.2]oct-3-yl)ester (Example 14e) (50 mg) in acetonitrile (1 mL) was added 2-bromo-N-phenylacetamide (Example 21a) (36 mg). The reaction mixture was stirred at room temperature for 3 days. Ether was added to the reaction mixture and the resultant solid was collected by filtration and dried to afford the title compound as a colourless solid (39 mg).

m/e 461 [M]+

$^1$H NMR (DMSO-D$_6$): δ 10.49 (s, 1H), 7.53-7.50 (m, 2H), 7.35-7.24 (m, 6H), 7.21-7.16 (m, 1H), 7.12-7.07 (m, 1H), 5.08 (m, 1H), 4.21-4.11 (m, 2H), 4.06 (dd, 1H), 3.64-3.49 (m, 4H), 3.27 (s, 1H), 2.37-2.21 (m, 2H), 2.18-2.04 (m, 2H), 1.98-1.88 (m, 3H), 1.77-1.66 (m, 1H), 1.70-1.30 (m, 9H).

EXAMPLE 22

(R)-3-(1-Phenyl-cycloheptanecarbonyloxy)-1-(pyrimidin-4-ylcarbamoylmethyl)-1-azonia-bicyclo[2.2.2]octane chloride a) 2-Chloro-N-pyrimidin-4-yl-acetamide

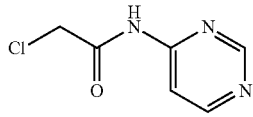

A solution of chloroacetyl chloride (1.22 mmol) in anhydrous CHCl$_3$ (2.4 mL) was added slowly to a mixture of 4-aminopyrimidine (1.11 mmol) and Et$_3$N (1.66 mmol) in anhydrous CHCl$_3$ (22 mL) at room temperature. The bright yellow mixture gradually turned orange and after 4 hr the reaction was quenched with H$_2$O (1 mL). After stirring for 15 min the mixture was concentrated to dryness under reduced pressure and the residue purified by flash silica gel chromatography (1-2% MeOH/dichloromethane) to give a yellow solid (122 mg).

$^1$H NMR (400 MHz, DMSO-D$_6$): δ 11.21 (s, 1H), 8.93-8.90 (m, 1H), 8.70 (d, 1H), 8.03 (dd, 1H), 4.40 (s, 2H).

EXAMPLE 22

(R)-3-(1-Phenyl-cycloheptanecarbonyloxy)-1-(pyrimidin-4-ylcarbamoylmethyl)-1-azonia-bicyclo[2.2.2]octane chloride

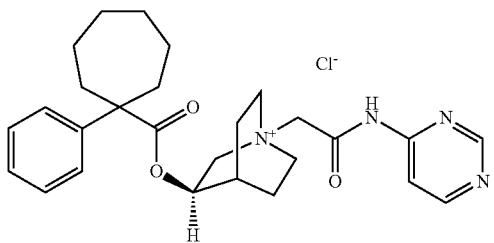

1-Phenyl-cycloheptanecarboxylic acid (R)-(1-aza-bicyclo[2.2.2]oct-3-yl)ester (Example 14e) (0.44 mmol) and 2-chloro-N-pyrimidin-4-yl-acetamide (Example 22a) (0.48 mmol) in anhydrous MeCN (2 mL) were stirred together at room temperature for 2.5 days. The reaction mixture was concentrated in vacuo and the residue purified by flash silica gel chromatography (2-10% MeOH/dichloromethane) to give the title compound as a light yellow solid (134 mg).

m/e 463 [M]+

$^1$H NMR (400 MHz, DMSO-D$_6$): δ 11.44 (s, 1H), 8.91 (s, 1H), 8.72 (d, 1H), 7.94 (d, 1H), 7.32-7.25 (m, 4H), 7.22-7.17 (m, 1H), 5.10-5.04 (m, 1H), 4.30 (s, 2H), 4.10-4.02 (m, 1H), 3.61-3.49 (m, 4H), 3.40-3.28 (m, 1H), 2.36-2.21 (m, 2H), 2.18-2.04 (m, 2H), 2.00-1.84 (m, 3H), 1.75-1.66 (m, 1H), 1.66-1.39 (m, 9H).

EXAMPLE 23

(R)-1-[(2-Fluoro-phenylcarbamoyl)-methyl]-3-(1-phenyl-cycloheptanecarbonyloxy)-1-azonia-bicyclo[2.2.2]octane bromide a) 2-Bromo-N-(2-fluoro-phenyl)-acetamide

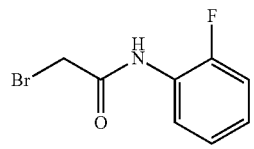

To a mixture of 2-fluoroaniline (2 mL) and potassium carbonate (4.3 g) in dichloromethane to (50 mL) was added bromoacetyl bromide (3.6 mL). The reaction mixture was stirred for 4h then water was added and the phases separated. The organic layer was concentrated, the residue treated with ether and evaporated again to give the sub-titled compound (4.98 g) as a cream solid that was used without further purification.

$^1$H NMR (400 MHz, CDCl$_3$): δ 8.38 (s, 1H), 8.26 (t, 1H), 7.18-7.09 (m, 3H), 4.05 (s, 2H).

EXAMPLE 23

(R)-1-[(2-Fluoro-phenylcarbamoyl)-methyl]-3-(1-phenyl-cycloheptanecarbonyloxy)-1-azonia-bicyclo[2.2.2]octane bromide

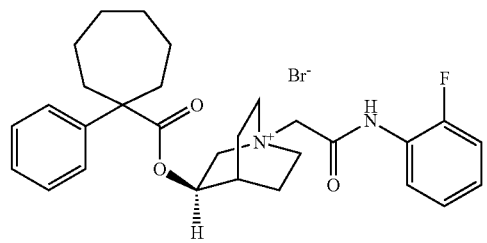

A mixture of 1-phenyl-cycloheptanecarboxylic acid (R)-(1-aza-bicyclo[2.2.2]oct-3-yl) ester (Example 14e) (56 mg) and 2-bromo-N-(2-fluoro-phenyl)-acetamide (Example 23a (44 mg) in acetonitrile (1 mL) was stirred at room temperature for 30 h. The resulting precipitate was collected by filtration, washed with ether and dried under vacuum at 50° C. to give the title compound (52 mg) as a colourless solid.

m/e 479 [M]

$^1$H NMR (400 MHz, DMSO-D$_6$): δ 10.34 (s, 1H), 7.83-7.77 (m, 1H), 7.32-7.16 (m, 8H), 5.12-5.03 (m, 1H), 4.25 (s, 2H), 4.10-4.02 (m, 1H), 3.63-3.51 (m, 4H), 3.41-3.29 (m,

1H), 2.37-2.23 (m, 2H), 2.17-2.06 (m, 2H), 1.98-1.88 (m, 3H), 1.79-1.67 (m, 1H), 1.66-1.39 (s, 9H).

EXAMPLE 24

(R)-1-[(2,3-Difluoro-phenylcarbamoyl)-methyl]-3-(1-phenyl-cycloheptanecarbonyloxy)-1-azonia-bicyclo[2.2.2]octane bromide a) 2-Bromo-N-(2,3-difluoro-phenyl)-acetamide

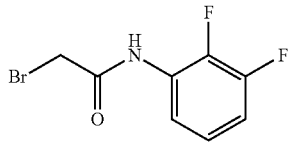

To a mixture of 2,3-difluoroaniline (630 mg) and potassium carbonate (1.01 g) in dichloromethane (30 mL) was added bromoacetyl bromide (0.86 mL). The reaction mixture was stirred for 5 h then water was added and the phases separated. The organic layer was concentrated to give a 2:1 mixture of the sub-titled compound and bromoacetyl bromide. The residue was dissolved up in dichloromethane and washed with water. The volatiles were evaporated to give the sub-titled compound (1.15 g) as an off-white solid that was used without further purification.

$^1$H NMR (400 MHz, CDCl$_3$): δ 8.38 (s, 1H), 8.03 (t, 1H), 7.12-7.05 (m, 1H), 7.00-6.92 (m, 1H), 4.05 (d, 2H).

EXAMPLE 24

(R)-1-[(2,3-Difluoro-phenylcarbamoyl)-methyl]-3-(1-phenyl-cycloheptanecarbonyloxy)-1-azonia-bicyclo[2.2.2]octane bromide

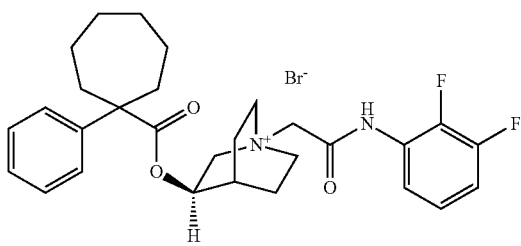

The title compound (colourless solid, 28 mg, 31%) was prepared by a similar procedure to that used for Example 23 using 2-bromo-N-(2,3-difluoro-phenyl)-acetamide (Example 24a) in place of 2-bromo-N-(2-fluoro-phenyl)-acetamide.

m/e 497 [M]$^+$ $^1$H NMR (400 MHz, DMSO-D$_6$): δ 10.54 (s, 1H), 7.58 (t, 1H), 7.32-7.16 (m, 7H), 5.13-5.04 (m, 1H), 4.26 (s, 2H), 4.10-4.02 (m, 1H), 3.62-3.49 (m, 4H), 3.42-3.29 (m, 1H), 2.37-2.23 (m, 2H), 2.17-2.06 (m, 2H), 1.98-1.85 (m, 3H), 1.79-1.67 (m, 1H), 1.66-1.40 (m, 9H).

EXAMPLE 25

(R)-1-[2-(2,3-Dihydro-benzofuran-5-yl)-ethyl]-3-(1-phenyl-cycloheptanecarbonyloxy)-1-azonia-bicyclo[2.2.2]octane formate

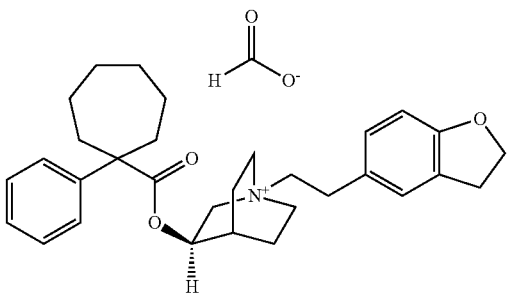

A mixture of 1-phenyl-cycloheptanecarboxylic acid (R)-(1-aza-bicyclo[2.2.2]oct-3-yl) ester (Example 14e) (126 mg) and 5-(2-bromo-ethyl)-2,3-dihydro-benzofuran (105 mg, 0.46 mmol) in acetonitrile (1.5 mL) was stirred at room temperature for 22 h. The volatiles were evaporated and the residue purified by silica gel chromatography eluting with dichloromethane then 5% then 10% MeOH/dichloromethane. The relevant fractions were combined and evaporated and the residue triturated with dichloromethane to give an off-white foam. Further purification was achieved by reverse-phase HPLC (5-98% MeCN containing 0.1% formic acid) to give the title compound (70 mg) as a white gummy solid.

m/e 474 [M]$^+$ $^1$H NMR (400 MHz, DMSO-D$_6$): δ 8.35 (s, 1H), 7.35-7.26 (m, 4H), 7.24-7.18 (m, 1H), 7.12 (s, 1H), 6.95 (d, 1H), 6.68 (d, 1H), 5.08-5.01 (m, 1H), 4.46 (t, 2H), 3.87-3.78 (m, 1H), 3.47-3.25 (m, 5H), 3.20-3.06 (m, 3H), 3.04-2.97 (m, 1H), 2.86-2.75 (m, 2H), 2.39-2.23 (m, 2H), 2.18-2.10 (m, 2H), 2.01-1.78 (m, 3H), 1.69-1.44 (m, 10H).

EXAMPLE 26

(R)-1-[2-(4-Fluoro-phenoxy)-ethyl]-3-(1-phenyl-cycloheptanecarbonyloxy)-1-azonia-bicyclo[2.2.2]octane formate

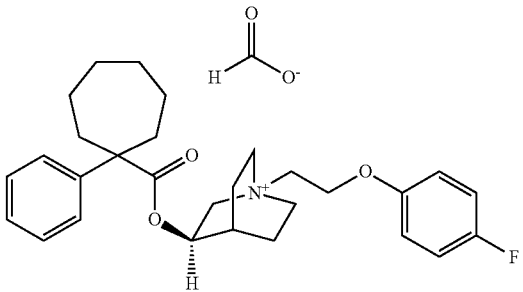

A mixture of 1-phenyl-cycloheptanecarboxylic acid (R)-(1-aza-bicyclo[2.2.2]oct-3-yl) ester (Example 14e) (50 mg)

and 1-(2-bromoethoxy)-4-fluorobenzene (50 mg) in acetonitrile (1 mL) was stirred at room temperature for 22 h. Purification by prep. HPLC using 5-98% MeCN/H$_2$O containing 0.1% formic acid gave the title compound (19 mg) as a colourless oil.

m/e 466 [M]$^+$ $^1$H NMR (400 MHz, DMSO-D$_6$): δ 8.39 (s, 1H), 7.28-7.23 (m, 4H), 7.20-7.11 (m, 3H), 6.97-6.92 (m, 2H), 5.06-4.99 (m, 1H), 4.39-4.28 (m, 2H), 3.93 (ddd, 1H), 3.70-3.56 (m,2H), 3.56-3.46 (m, 4H), 3.15-3.03 (m, 1H), 2.35-2.20 (m, 2H), 2.15-2.03 (m, 2H), 1.97 -1.78 (m, 3H), 1.73-1.61 (m, 1H), 1.61-1.39 (m, 9H).

EXAMPLE 27

(R)-3-(1-phenyl-cycloheptanecarbonyloxy)-1-(pyridazin-4-ylcarbamoylmethyl)-1-azonia-bicyclo[2.2.2]octane formate a) 2-Chloro-N-pyridazin-4-yl-acetamide

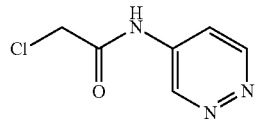

A solution of pyridazin-4-ylamine (1.0 g) in dry dichloromethane (10 mL) under nitrogen was cooled to 0° C. in an ice bath. Triethylamine (1.6 mL) was added, followed by slow addition of chloroacetyl chloride (0.92 mL). On completion of the addition the ice bath was removed and the reaction mixture was allowed to reach room temperature and stirred for 2 hours. The reaction mixture was diluted with water (25 mL) and dichloromethane (30 mL) A solid was filtered off and washed with pentane, water and more pentane to give the sub-titled compound (0.87 g, 48%) as a brown solid.

$^1$H NMR (400 MHz, DMSO-D$_6$): δ 11.17 (s, 1H), 9.33 (dd, 1H), 9.07 (dd, 1H), 7.94 (dd, 1H), 4.39 (s, 2H).

EXAMPLE 27

(R)-3-(1-phenyl-cycloheptanecarbonyloxy)-1-(pyridazin-4-ylcarbamoylmethyl)-1-azonia-bicyclo[2.2.2]octane formate

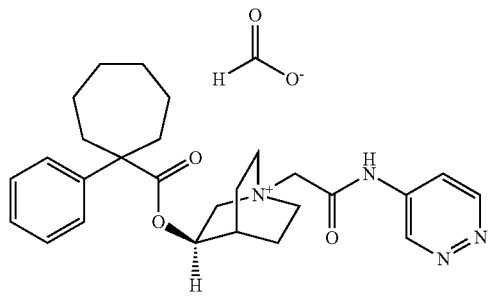

2-Chloro-N-pyridazin-4-yl-acetamide (Example 27a) (58 mg) was added to a solution of 1-phenyl-cycloheptanecarboxylic acid (R)-(1-aza-bicyclo[2.2.2]oct-3-yl)ester (Example 14e) (100 mg) in acetonitrile (2 mL). The reaction mixture was allowed to stir at room temperature for 24 h. Diethyl ether (2 mL) was added to the reaction mixture and stirred for 15 minutes. The solid was filtered off, washed with diethyl ether, and dried under vacuum at 40° C. overnight. The filtrate was evaporated, combined with the solid and purified by column chromatography, eluting with 0-15% MeOH/dichloromethane. Further purification by reverse-phase prep HPLC with gradient elution from 15% MeCN/H$_2$O containing 0.1% formic acid increasing by 1% per minute gave the title compound (19 mg) as a colourless gum.

m/e 463 [M]

$^1$H NMR (400 MHz, DMSO-D$_6$): δ 9.17 (s, 1H), 8.89 (d, 1H), 8.41 (s, 1H), 7.80 (dd, 1H), 7.32-7.25 (m, 4H), 7.21-7.15 (m, 1H), 5.08-5.02 (m, 1H), 4.28-4.14 (m, 2H), 4.04(dd, 1H), 3.66 (d, 2H), 3.62-3.48 (m, 2H), 3.45-3.33 (m, 1H), 2.37-2.23 (m, 2H), 2.14-2.05 (m, 2H), 1.96-1.83 (m, 3H), 1.75-1.62 (m, 1H), 1.56-1.42 (m, 9H).

EXAMPLE 28

(R)-1-[(5-Fluoro-pyridin-3-ylcarbamoyl)-methyl]-3-(1-phenyl-cycloheptanecarbonyloxy)-1-azonia-bicyclo[2.2.2]octane chloride a) 2-Chloro-N-(5-fluoro-pyridin-3-yl)-acetamide

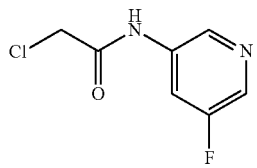

A solution of 3-amino-fluoropyridine (1 g) in dry dichloromethane (10 mL) under nitrogen was cooled to 0° C. in an ice bath. Triethylamine (1.36 mL) was added followed by slow addition of chloroacetyl chloride (0.78 mL). On completion of the addition, the ice bath was removed and the reaction mixture was allowed to reach room temperature and was stirred for 2 hours. The reaction mixture was diluted with water (25 mL) and dichloromethane (30 mL). The organic layer was washed with water (2×20 mL), dried (MgSO$_4$) and evaporated to give the crude product. Purification was achieved by silica gel chromatography eluting with 0-30% ethyl acetate/cyclohexane to give the sub-titled compound (1.0 g) as a tan coloured solid.

$^1$H NMR (400 MHz, DMSO-D$_6$): δ 10.77 (s, 1H), 8.56 (t, 1H), 8.33 (d, 1H), 8.04 (dt, 1H), 4.33 (s, 2H).

EXAMPLE 28

(R)-1-[(5-Fluoro-pyridin-3-ylcarbamoyl)-methyl]-3-(1-phenyl-cycloheptanecarbonyloxy)-1-azonia-bicyclo[2.2.2]octane chloride

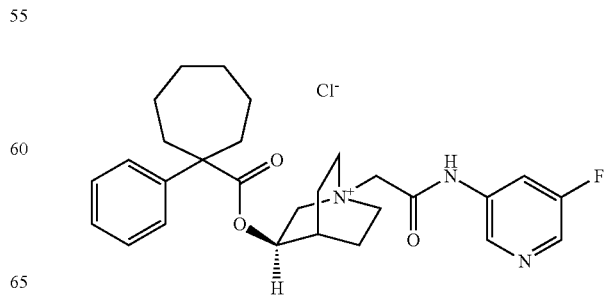

2-Chloro-N-(5-fluoro-pyridin-3-yl)-acetamide (Example 28a) (53 mg) was added to a solution of 1-phenyl-cycloheptanecarboxylic acid (R)-(1-aza-bicyclo[2.2.2]oct-3-yl) ester (Example 14e) (84 mg) in acetonitrile (2 mL). The reaction mixture was allowed to stir at room temperature for 24 h. The solid was filtered off and dried under vacuum at 40° C. to give the title compound (47 mg, 35%) as a white solid.

m/e 480 [M]$^+$ $^1$H NMR (400 MHz, DMSO-D$_6$): δ 11.53 (s, 1H), 8.58 (s, 1H), 8.34 (d, 1H), 7.99 (dt, 1H), 7.32-7.25 (m, 4H), 7.21-7.15 (m, 1H), 5.09-5.04 (m, 1H), 4.29 (s, 2H), 4.10-4.02 (m, 1H), 3.63-3.51 (m, 4H), 3.41-3.29 (m, 1H), 2.37-2.23 (m, 2H), 2.16-2.05 (m, 2H), 1.96-1.83 (m, 3H), 1.78-1.65 (m, 1H), 1.65-1.39 (m, 9H).

EXAMPLE 29

(R)-3-(1-phenyl-cycloheptanecarbonyloxy)-1-[2-(pyridin-3-yloxy)-ethyl]-1-azonia-bicyclo[2.2.2]octane formate a) 2-(Pyridin-3-yloxy)-ethanol

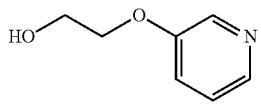

The sub-titled compound (0.99 g, 63%) was prepared according to the procedure described in WO2004/000829.

b) 3-(2-Bromo-ethoxy)-pyridine

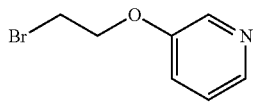

A solution of 2-(pyridin-3-yloxy)-ethanol (200 mg) in 5 mL dichloromethane was cooled to 0° C. and treated with carbon tetrabromide (524 mg) followed by triphenylphosphine (415 mg) portionwise. The reaction mixture was stirred at 0° C. for 30 mins then at room temperature for 45 mins. The volatiles were evaporated and the residue purified by silica gel chromatography eluting with 0-100% EtOAc/pentane to give the title compound (204 mg) as a colourless liquid which was used without further purification.

$^1$H NMR (400 MHz, CDCl$_3$): δ 8.34 (dd, 1H), 8.28-8.22 (m, 1H), 7.25-7.20 (m, 2H), 4.35 (t, 2H), 3.66 (t, 2H).

EXAMPLE 29

(R)-3-(1-Phenyl-cycloheptanecarbonyloxy)-1-[2-(pyridin-3-yloxy)-ethyl]-1-azonia-bicyclo[2.2.2]octane formate

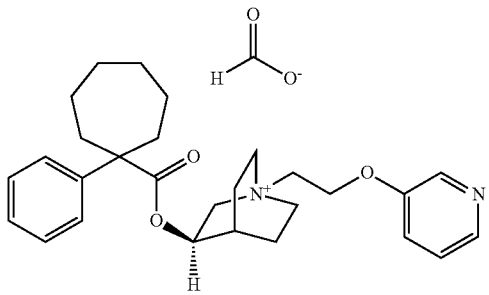

The title compound (10 mg, 13%, colourless gum) was prepared using a procedure analogous to that used for the preparation of Example 25 using 3-(2-Bromo-ethoxy)-pyridine (Example 29b) in place of 5-(2-bromo-ethyl)-2,3-dihydro-benzofuran.

m/e 449 [M]$^+$ $^1$H NMR (400 MHz, DMSO-D6): δ 8.51 (s, 1H), 8.29 (d, 1H), 8.21 (dd, 1H), 7.38-7.33 (m, 2H), 7.28-7.24 (m, 4H), 7.19-7.14 (m, 1H), 5.06-4.99 (m, 1H), 4.51-4.39 (m, 2H), 3.99-3.90 (m, 1H), 3.74-3.59 (m, 2H), 3.57-3.37 (m, 3H), 3.14-3.05 (m, 1H), 2.36-2.22 (m, 2H), 2.14-2.05 (m, 2H), 1.98-1.82 (m, 3H), 1.74-1.62 (m, 1H), 1.62-1.38 (m, 9H).

EXAMPLE 30

(R)-1-[(6-Methyl-pyridin-2-ylcarbamoyl)-methyl]-3-(1-phenyl-cycloheptanecarbonyloxy)-1-azonia-bicyclo[2.2.2]octane chloride a) 2-Chloro-N-(6-methyl-pyridin-2-yl)-acetamide

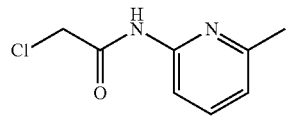

The sub-titled compound (0.95 g, 58%, white solid) was prepared by a similar procedure to that used for the preparation of Example 28a using 2-amino-6-picoline in place of 3-amino-5-fluoropyridine.

$^1$H NMR (400 MHz, DMSO-D$_6$): δ 10.73 (s, 1H), 7.86 (d, 1H), 7.69 (t, 1H), 7.03-6.96 (m,1H), 4.32 (s, 2H), 2.41 (s, 3H).

EXAMPLE 30

(R)-1-[(6-Methyl-pyridin-2-ylcarbamoyl)-methyl]-3-(1-phenyl-cycloheptanecarbonyloxy)-1-azonia-bicyclo[2.2.2]octane chloride

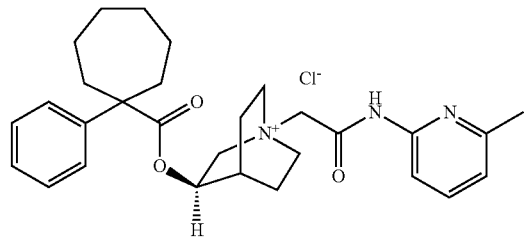

The title compound (34 mg, 43%, white solid) was prepared using a similar method to that used to prepare Example 17 using 2-chloro-N-(6-methyl-pyridin-2-yl)-acetamide (Example 30a) in place of 2-chloro-N-(5-fluoro-pyridin-2-yl)-acetamide.

m/e 476 [M]$^+$ $^1$H NMR (400 MHz, DMSO-D$_6$): δ 11.01 (s, 1H), 7.79 (d, 1H), 7.71 (t, 1H), 7.32-7.25 (m, 4H), 7.23-7.16 (m, 1H), 7.02 (d, 1H), 5.09-5.04 (m, 1H), 4.24 (s, 2H), 4.06 (ddd, 1H), 3.63-3.50 (m, 4H), 3.38-3.29 (m, 1H), 2.38 (s, 3H), 2.38-2.23 (m, 2H), 2.17-2.04 (m, 2H), 2.00-1.82 (m, 3H), 1.78-1.66 (m, 1H), 1.65-1.40 (m, 9H).

EXAMPLE 31

(R)-3-(1-Phenyl-cycloheptanecarbonyloxy)-1-(o-tolylcarbamoyl-met 1-azonia-bicyclo[2.2.2]octane bromide a) 2-Chloro-N-o-tolyl-acetamide

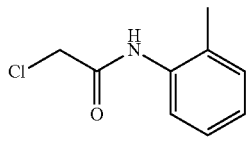

The sub-titled compound (0.83 g, 49%, off-white solid) was prepared using a procedure similar to that used to prepare Example 28a using o-toluidine in place of 3-amino-5-fluoro-pyridine.

$^1$H NMR (400 MHz, DMSO-D$_6$): δ 9.62 (s, 1H), 7.39 (d, 1H), 7.23-7.08 (m, 3H), 4.29 (s, 2H), 2.23 (s, 3H).

EXAMPLE 31

(R)-3-(1-Phenyl-cycloheptanecarbonyloxy)-1-(o-tolylcarbamoyl-methyl) -1-azonia-bicyclo[2.2.2]octane bromide

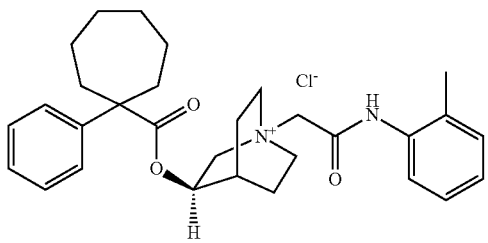

The title compound (25 mg, 35%, white solid) was prepared using a similar method to that used to prepare Example 17 using 2-chloro-N-o-tolyl-acetamide (Example 31a) in place of 2-chloro-N-(5-fluoro-pyridin-2-yl)-acetamide.

m/e 475 [M]$^+$ $^1$H NMR (400 MHz, DMSO-D$_6$): δ 10.26 (s, 1H), 7.34 (dd, 1H), 7.31-7.25 (m, 4H), 7.23-7.09 (m, 4H), 5.11-5.05 (m, 1H), 4.31 (dd, 2H), 4.07 (ddd, 1H), 3.68-3.52 (m, 4H), 3.40-3.31 (m, 1H), 2.38-2.22 (m, 2H), 2.19 (s, 3H), 2.17-2.06 (m, 2H), 1.97-1.84 (m 3H), 1.79-1.67 (m, 1H) 1.65-1.39 (m, 9H).

EXAMPLE 32

(R)-3-(1-Phenyl-cycloheptanecarbonyloxy)-1-(2-pyrazin-2-yl-ethyl)-azonia-bicyclo[2.2.2]octane bromide a) 2-(2-Bromo-ethyl)-pyrazine

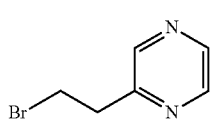

To a solution of 2-(2'-hydroxyethyl)pyrazine (0.91 g) in 30 mL dichloromethane at 0° C. was added carbon tetrabromide (2.65 g) followed by triphenylphosphine (2.1 g) portionwise. The solution became very dark. After stirring for 1 h the reaction mixture was adsorbed onto HMN diatomaceous earth and purified by silica gel chromatography eluting with 0-5% MeOH/dichloromethane to give a cream solid (3.07 g) that was purified further by silica gel chromatography eluting with 0-50% EtOAc/pentane to give the sub-titled compound (0.47 g, 34%) as a yellow oil.

$^1$H NMR (400 MHz, CDCl$_3$): δ 8.56-8.48 (m, 3H), 3.78 (t, 2H), 3.37 (t, 2H).

EXAMPLE 32

(R)-3-(1-Phenyl-cycloheptanecarbonyloxy)-1-(2-pyrazin-2-yl-ethyl)-azonia-bicyclo[2.2.2]octane bromide

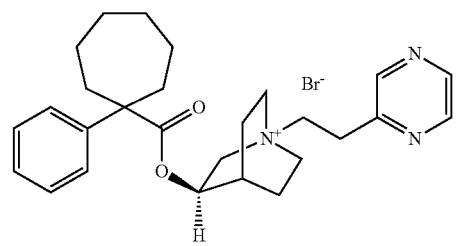

2-(2-Bromo-ethyl)-pyrazine (Example 32a) (43 mg) was added to a solution of 1-phenyl -cycloheptanecarboxylic acid (R)-(1-aza-bicyclo[2.2.2]oct-3-yl)ester (Example 14e) (50 mg) in acetonitrile (1 mL). The reaction mixture was allowed to stir at room temperature for 68 h. The volatiles were evaporated and the product was purified by silica gel chromatography eluting with 0-20% MeOH/dichloromethane. The relevant fractions were combined and concentrated, dissolved up in dichloromethane, filtered and evaporated to give the title compound (30 mg) as a yellow gummy glass.

m/e 434 [M]$^+$ $^1$H NMR (400 MHz, CD$_3$OD): δ 8.60 (d, 1H), 8.54 (dd, 1H), 8.51 (d, 1H), 7.31-7.24 (m, 4H), 7.21-7.15 (m, 1H), 5.05-4.98 (m, 1H), 3.86 (ddd, 1H), 3.57 (t, 2H), 3.49-3.30 (m, 3H), 3.24-3.12 (m, 3H), 3.08-2.97 (m, 1H), 2.36-2.19 (m, 2H), 2.15-2.06 (m, 2H), 1.97-1.78 (m, 3H), 1.71-1.59 (m, 1H), 1.57-1.37 (m, 9H).

EXAMPLE 33

(S)-1-(3-Phenoxy-propyl)-3-(1-phenyl-cycloheptanecarbonyloxy)-1-azonia-bicyclo[2.2.2]octane formate a) 1-Phenyl-cycloheptanecarboxylic acid (S)-(1-aza-bicyclo[2.2.2]oct-3-yl)ester

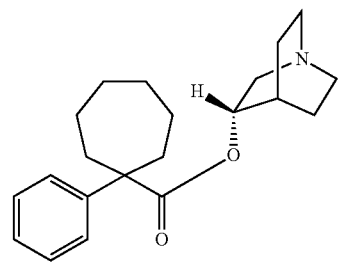

A solution of (S)-(+)-3-quinuclidinol (299 mg) and 1-phenyl-cycloheptanecarboxylic acid methyl ester (Example 14d) (455 mg) in 6.5 mL dry toluene under nitrogen was treated with a 60% dispersion of sodium hydride (94 mg) and the mixture was heated to reflux for 24 h then cooled to room temperature and allowed to stand over the weekend. EtOAc and sat. NaHCO$_3$ $_{(aq)}$ were added and the phases separated. The aqueous phase was extracted with EtOAc (×3) and the combined organic layer was washed with brine, dried (MgSO$_4$) and evaporated to afford the crude product. Purification was achieved by silica gel chromatography eluting with 0-10% MeOH/dichloromethane to give the sub-titled compound (384 mg) as a yellow oil.

$^1$H NMR (300 MHz, CD$_3$OD): δ 7.39-7.27 (m, 4H), 7.25-7.14 (m, 1H), 4.80 (dt, 1H), 3.16 (ddd, 1H), 2.83-2.64 (m, 3H), 2.56-2.34 (m, 4H), 2.15-2.04 (m, 2H), 1.91-1.86 (m, 1H), 1.72-1.44 (m, 11H), 1.38-1.25 (m, 1H).

EXAMPLE 33

(S)-1-(3-Phenoxy-propyl)-3-(1-phenyl-cycloheptanecarbonyloxy)-1-azonia-bicyclo[2.2.2]octane formate

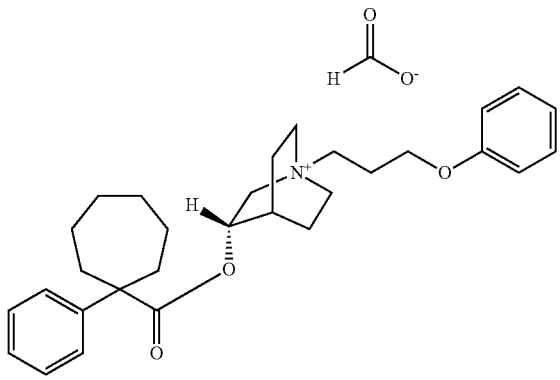

A mixture of 3-phenoxypropyl bromide (0.026 mL) was added to a solution of 1-phenyl-cycloheptanecarboxylic acid (S)-(1-aza-bicyclo[2.2.2]oct-3-yl)ester (Example 33a) (50 mg) in acetonitrile (1 mL). The reaction mixture was allowed to stir at room temperature for 72 hrs then heated to 50° C. for 3 days. The volatiles were evaporated and the residue purified by silica gel chromatography eluting with 0-10% MeOH/dichloromethane to give 57 mg of a hygroscopic foam. Further purification was achieved by reverse phase HPLC using a C18 column eluting with 5-95% MeCN/H$_2$O containing 0.1% formic acid ° over 30 mins gave the title compound (43 mg) as an oil.

m/e 462 [M]$^+$ $^1$H NMR (400 MHz, DMSO-D$_6$): δ 8.38 (s, 1H), 7.34-7.24 (m, 6H), 7.23-7.17 (m, 1H), 6.94-6.87 (m, 3H), 5.07-4.97 (m, 1H), 3.98 (t, 2H), 3.87-3.77 (m, 1H), 3.44-3.26 (m, 5H), 3.16-3.09 (m, 1H), 3.01-2.90 (m, 1H), 2.38-2.23 (m, 2H), 2.16-1.77 (m, 7H), 1.69-1.43 (m, 10H).

EXAMPLE 34

(R)-1-{[2-(3-Fluoro-phenoxy)-ethylcarbamoyl]-methyl}-3-(1-phenyl-cycloheptanecarbonyloxy)-1-azonia-bicyclo[2.2.2]octane bromide a) 2-Bromo-N-[2-(3-fluoro-phenoxy)-ethyl]acetamide

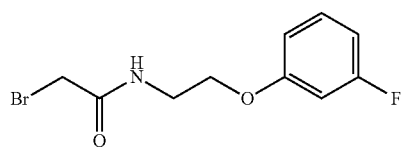

A mixture of 2-(3-fluorophenoxy)ethylamine (0.93 g) and potassium carbonate (1.24 g in dichloromethane (20 mL) at 0° C. was treated with bromoacetyl bromide (1.04 mL). The reaction mixture was stirred at 0° C. for 30 mins then at room temperature for 6 h. Water was added and the mixture was stirred until effervescence ceased. The organic layer was separated and the organic layer was evaporated to afford the crude product which was purified by silica gel chromatography eluting with 0-50% EtOAc/pentane to give the sub-titled compound (1.17 g) as a brown oil.

$^1$H NMR (400 MHz, CDCl$_3$): δ 7.24 (dt, 1H), 6.90 (s, 1H), 6.71-6.66 (m, 2H), 6.63 (dt, 1H), 4.06 (t, 2H), 3.90 (s, 2H), 3.71 (q, 2H).

EXAMPLE 34

(R)-1-{[2-(3-Fluoro-phenoxy)-ethylcarbamoyl]-methyl}-3-(1-phenyl cycloheptanecarbonyloxy)-1-azonia-bicyclo[2.2.2]octane bromide

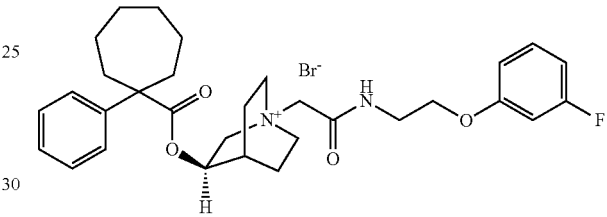

The title compound (70 mg, 76%, yellow foam) was prepared by a similar procedure to that used to prepare Example 32 using 2-bromo-N-[2-(3-fluoro-phenoxy)-ethyl]-acetamide (Example 34a) in place of 2-(2-bromo-ethyl)-pyrazine.

m/e 523 [M]$^+$ $^1$H NMR (400 MHz, DMSO-D$_6$): δ 8.74 (t, 1H), 7.33-7.23 (m, 5H), 7.23-7.16 (m, 1H), 6.79-6.71 (m, 3H), 5.09-5.02 (m, 1H), 4.03-3.94 (m, 5H), 3.57-3.40 (m, 6H), 3.33-3.22 (m, 1H), 2.35-2.20 (m, 2H), 2.10 (d, 2H), 1.96-1.82 (m, 3H), 1.74-1.62 (m, 1H), 1.62-1.40 (m, 9H).

EXAMPLE 35

(R)-1-[(3,5-Difluoro-phenylcarbamoyl)-methyl]-3-(1-phenyl-cycloheptanecarbonyloxy)-1-azonia-bicyclo[2.2.2]octane bromide a) 2-Bromo-N-(3,5-difluoro-phenyl)-acetamide

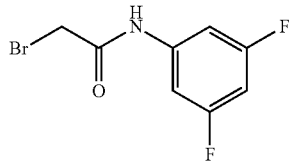

The sub-titled compound (2.02 g, colourless waxy solid) was prepared using a similar procedure to that used for the preparation of Example 38a but using 3,5-difluoroaniline in place of 2,6-difluoroaniline.

$^1$H NMR (400 MHz, CDCl$_3$): δ 8.17 (s, 1H), 7.16 (d, 2H), 6.63 (td, 1H), 4.02 (s, 2H).

EXAMPLE 35

(R)-1-[(3,5-Difluoro-phenylcarbamoyl)-methyl]-3-(1-phenyl-cycloheptanecarbonyloxy)-1-azonia-bicyclo[2.2.2]octane bromide

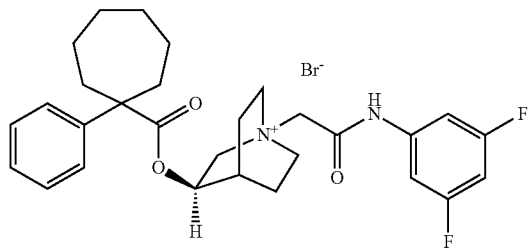

A mixture of 2-bromo-N-(3,5-difluoro-phenyl)-acetamide (42 mg) (Example 35a) and 1-phenyl-cycloheptanecarboxylic acid (R)-(1-aza-bicyclo[2.2.2]oct-3-yl)ester (Example 14e) (50 mg) in MeCN (1 mL) was stirred at room temperature for 72 h. The solid precipitate was filtered off, washed with ether and dried at 50° C. under vacuum overnight. The mother liquors were evaporated, treated with ether and the resulting solid was filtered off. The solids were combined and crystallised from hot isopropyl alcohol to give the title compound (15 mg) as a colourless solid.

m/e 497 [M]$^+$ $^1$H NMR (400 MHz, DMSO-D$_6$): δ 10.89 (s, 1H), 7.33-7.17 (m, 7H), 7.01 (tt, 1H), 5.13-5.06 (m, 1H), 4.26-4.14 (m, 2H), 4.10-4.01 (m, 1H), 3.63-3.49 (m, 4H), 3.43-3.32 (m, 1H), 2.38-2.23 (m, 2H), 2.18-2.06 (m, 2H), 1.98-1.86 (m, 3H), 1.79-1.67 (m, 1H), 1.65-1.41 (m, 9H).

EXAMPLE 36

(R)-1-[2-(4-methoxy-benzyloxy)-ethyl]-3-(1-phenyl-cycloheptanecarbonyloxy)-1-azonia-bicyclo[2.2.2]octane formate

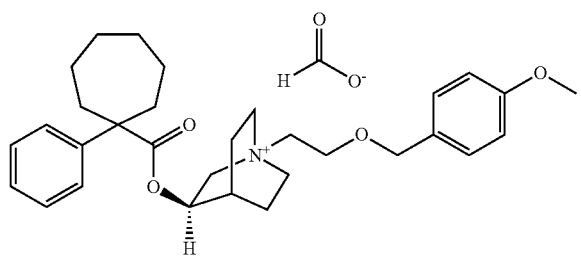

A mixture of 1-(2-bromo-ethoxymethyl)-4-methoxy-benzene (42 mg) and 1-phenyl-cycloheptanecarboxylic acid (R)-(1-aza-bicyclo[2.2.2]oct-3-yl)ester (Example 14e) (50 mg) in MeCN (1 mL) was stirred at room temperature for 16 h then heated to 80° C. under nitrogen overnight. A further 1.1 equivalents of 1-(2-bromo-ethoxymethyl)-4-methoxy -benzene were added and the mixture was heated at 80° C. for a further 48 h. The volatiles were evaporated and the crude product was purified by silica gel chromatography eluting with 0-10% of a 10% conc. NH$_3$/MeOH solution in dichloromethane give 61 mg of an oil that was purified further by reverse phase HPLC (Gemini 5 μM C6 phenyl column) eluting with 5-95% MeOH/H$_2$O containing 0.1% formic acid over 30 min with UV detection at 220 nm. The relevant fractions were combined and evaporated to afford the title compound (34 mg) as an oil.

m/e 492 [M]$^+$ $^1$H NMR (400 MHz, CD$_3$OD): δ 8.48 (s, 1H), 7.31-7.16 (m, 7H), 6.91-6.86 (m, 2H), 5.09-5.03 (m, 1H), 4.44-4.39 (m, 2H), 3.92-3.63 (m, 6H), 3.46-3.29 (m, 5H), 2.99-2.88 (m, 1H), 2.43-2.28 (m, 2H), 2.24-2.20 (m, 1H), 2.15-1.86 (m, 4H), 1.75-1.51 (m, 10H).

EXAMPLE 37

(R)-1-(2-Phenethyloxy-ethyl)-3-(1-phenyl-cycloheptanecarbonyloxy) azonia-bicyclo[2.2.2]octane bromide

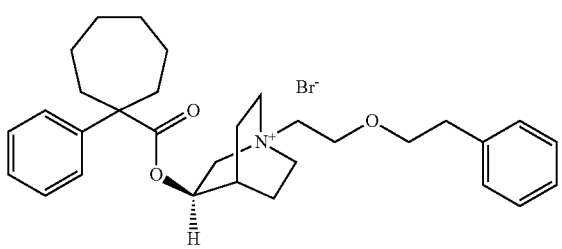

The title compound (68 mg, 77%, gummy solid) was prepared according to a similar procedure to that used for Example 36 using [2-(2-bromo-ethoxy)-ethyl]-benzene in place of 1-(2-bromo-ethoxymethyl)-4-methoxy-benzene.

m/e 476 [M]$^+$ $^1$H NMR (400 MHz, DMSO-D$_6$): δ 7.32-7.11 (m, 10H), 5.00-4.92 (m, 1H), 3.80-3.65 (m, 3H), 3.60 (t, 2H), 3.41-3.11 (m, 6H), 2.99-2.88 (m, 1H), 2.77 (t, 2H), 2.38-2.21 (m, 2H), 2.17-2.04 (m, 2H), 1.99-1.89 (m, 1H), 1.84-1.67 (m, 2H), 1.67-1.32 (m, 10H).

EXAMPLE 38

(R)-1-[(2,6-Difluoro-phenylcarbamoyl)-methyl]-3-(1-phenyl-cycloheptanecarbonyloxy)-1-azonia-bicyclo[2.2.2]octane bromide a) 2-Bromo-N-(2,6-difluoro-phenyl)-acetamide

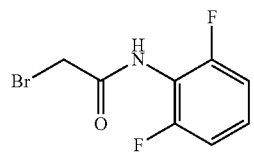

To a mixture of 2,6-difluoroaniline (1.12 g) and potassium carbonate (1.8 g) in 50 mL dichloromethane was added bromoacetyl bromide (1.5 mL) and the mixture was stirred at room temperature for 17 h. Water was added and the mixture stirred for several hours then the phases were separated on a hydrophobic frit and the organic layer was evaporated. The crude product was purified by silica gel chromatography eluting with 0-100% EtOAc/cyclohexane to give the sub-titled compound (0.92 g) as a white solid.

$^1$H NMR (400 MHz, CDCl$_3$): δ 7.74 (s, 1H), 7.31-7.21 (m, 1H), 6.98 (t, 2H), 4.08 (s, 2H).

EXAMPLE 38

(R)-1-[(2,6-Difluoro-phenylcarbamoyl)-methyl]-3-(1-phenyl-cycloheptanecarbonyloxy)-1-azonia-bicyclo[2.2.2]octane bromide

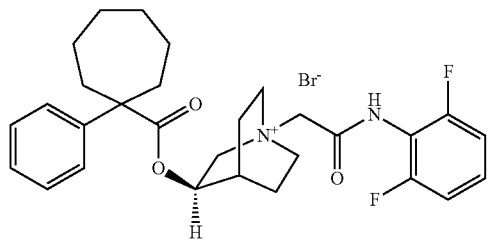

A mixture of 2-bromo-N-(2,6-difluoro-phenyl)-acetamide (Example 38a) (42 mg) and 1-phenyl-cycloheptanecarboxylic acid (R)-(1-aza-bicyclo[2.2.2]oct-3-yl)ester (Example 14e) (50 mg) in MeCN (1 mL) was stirred at room temperature for 19 h. A further 20 mg 2-bromo-N-(2,6-difluorophenyl)-acetamide was added and stirring continued for another 22 h. The volatiles were evaporated and the residue was purified by silica gel chromatography eluting with 0-10% MeOH/dichloromethane to give the title compound (41 mg) as a colourless foam.

m/e 497 [M]$^+$ $^1$H NMR (400 MHz, DMSO-D$_6$): δ 10.40 (s, 1H), 7.42-7.35 (m, 1H), 7.31-7.25 (m, 4H), 7.22-7.16 (m, 3H), 5.12-5.05 (m, 1H), 4.32-4.27 (m, 2H), 4.10-4.02 (m, 1H), 3.66-3.49 (m, 4H), 3.43-3.31 (m, 1H), 2.36-2.21 (m, 2H), 2.17-2.06 (m, 2H), 1.99-1.85 (m, 3H), 1.77-1.66 (m, 1H), 1.68-1.25 (m, 9H).

EXAMPLE 39

(R)-1-[(Methyl-phenyl-carbamoyl)-methyl]-3-(1-phenyl-cycloheptanecarbonyloxy)-1-azonia-bicyclo[2.2.2]octane formate a) 2-Bromo-N-methyl-N-phenyl-acetamide

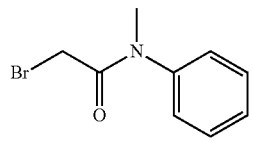

To a mixture of N-methyl aniline (5 mL) and potassium carbonate (9.6 g) in 100 mL dichloromethane was added bromoacetyl bromide (8.1 mL) (exotherm). The mixture was stirred for 4.5h then water was added. The phases were separated and the organic layer was concentrated. The crude product was purified by silica gel chromatography eluting with 0-100% EtOAc/cyclohexane. The relevant fractions were combined and evaporated and the residue was taken up in dichloromethane and washed with water. The organic layer was stirred with another portion of water for a few minutes and then the layers were separated. Evaporation of the organic layer gave the sub-titled compound (10.2 g) as a straw coloured solid.

$^1$H NMR (400 MHz, CDCl$_3$): δ 7.50-7.36 (m, 3H), 7.31-7.26 (m, 2H), 3.67 (s, 2H), 3.31 (s, 3H).

EXAMPLE 39

(R)-1-[(Methyl-phenyl-carbamoyl)-methyl]-3-(1-phenyl-cycloheptanecarbonyloxy)-1-azonia-bicyclo[2.2.2]octane formate

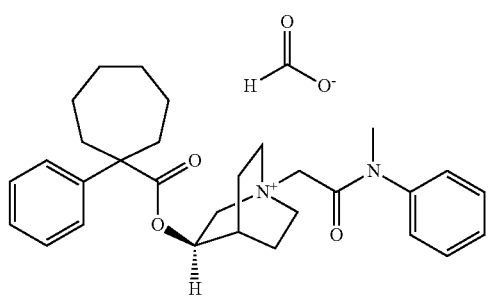

A mixture of 2-bromo-N-methyl-N-phenyl-acetamide ((Example 39a) (38 mg) and 1-phenyl-cycloheptanecarboxylic acid (R)-(1-aza-bicyclo[2.2.2]oct-3-yl)ester (Example 14e) (50 mg) in 1 mL MeCN was stirred at room temperature for 48 h. The volatiles were evaporated and the residue purified by silica gel chromatography eluting with 0-10% MeOH/dichloromethane. Further purification by reverse phase HPLC eluting with 20-90% MeCN/H$_2$O containing 0.1% formic acid gave the title compound (17 mg) as a colourless gum.

m/e 475 [M]$^+$ $^1$H NMR (400 MHz, DMSO-D$_6$ with a drop of TFA-D): δ 8.08 (s, 1H), 7.47 (t, 2H), 7.39 (dd, 3H), 7.32-7.23 (m, 4H), 7.20-7.15 (m, 1H), 5.09-4.98 (m, 1H), 4.01-3.83 (m, 3H) 3.61-3.34 (m, 5H), 3.16-3.09 (s, 3H) 2.37-2.21 (m, 2H), 2.16-2.05 (m, 2H), 1.96-1.75 (m, 3H), 1.7 1-1.36 (m, 10H).

EXAMPLE 40

(R)-1-[3-(4-Cyano-phenoxy)-propyl]-3-(1-phenyl-cycloheptanecarbonyloxy)-1-azonia-bicyclo[2.2.2]octane bromide

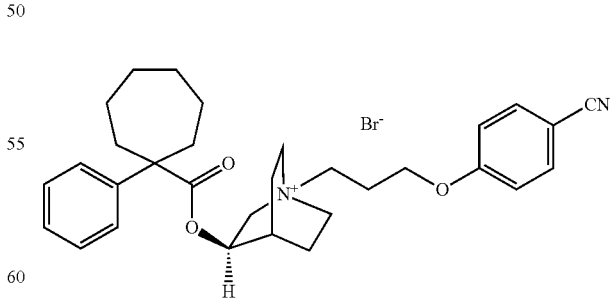

A mixture of 4-(3-bromo-propoxy)-benzonitrile (41 mg) and 1-phenyl-cycloheptanecarboxylic acid (R)-(1-aza-bicyclo[2.2.2]oct-3-yl)ester (Example 14e) (52 mg) in MeCN (1 mL) was stirred at room temperature for 16 h then heated to 80° C. under nitrogen for a further 16 h. The volatiles were evaporated and the residue was triturated with ether to give an off-white solid that was triturated with EtOAc and dried under vacuum to give the title compound (61 mg) as a white solid.
m/e 487 [M]⁺

¹H NMR (400 MHz, DMSO-D₆): δ 7.78-7.73 (m, 2H), 7.33-7.26 (m, 4H), 7.22-7.17 (m, 1H), 7.09-7.04 (m, 2H), 5.05-4.99 (m, 1H), 4.08 (t, 2H), 3.82 (ddd, 1H), 3.43-3.26 (m, 5H), 3.21-3.08 (m, 1H), 3.02-2.90 (m, 1H), 2.39-2.22 (m, 2H), 2.17-2.00 (m, 4H), 1.99-1.78 (m, 3H), 1.68-1.43 (m, 10H).

EXAMPLE 41

(R)-1-[(2,5-Difluoro-phenylcarbamoyl)-methyl]-3-(1-phenyl-cycloheptanecarbonyloxy)-1-azonia-bicyclo[2.2.2]octane bromide a) 2-Bromo-N-(2,5-difluoro-phenyl)-acetamide

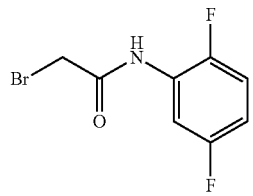

The sub-titled compound (3.6 g, 90%, orange solid) was prepared by a similar procedure to that used to prepare Example 38a using 2,5-difluoroaniline in place of 2,6-difluoroaniline.

¹H NMR (400 MHz, CDCl₃): δ 8.42 (s, 1H), 8.13 (ddd, 1H), 7.08 (ddd, 1H), 6.82-6.75 (m, 1H), 4.04 (s, 2H).

EXAMPLE 41

(R)-1-[(2,5-Difluoro-phenylcarbamoyl)-methyl]-3-(1-phenyl-cycloheptanecarbonyloxy)-1-azonia-bicyclo[2.2.2]octane bromide

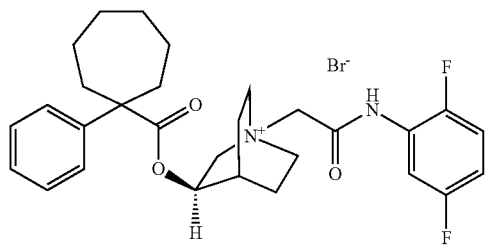

A mixture of 2-bromo-N-(2,5-difluoro-phenyl)-acetamide (Example 41a) (47 mg) and 1-phenyl-cycloheptanecarboxylic acid (R)-(1-aza-bicyclo[2.2.2]oct-3-yl)ester (Example 14e) (56 mg) in MeCN (1 mL) was stirred at room temperature for 30 h. The resulting precipitate was filtered off, washed with ether and dried at 50° C. under vacuum overnight to afford the title compound (65 mg) as a colourless solid.
m/e 497 [M]⁺

¹H NMR (400 MHz, DMSO-d☐): δ 10.51 (s, 1H), 7.82-7.75 (m, 1H), 7.38-7.26 (m, 5H), 7.21-7.16 (m, 1H), 7.09-7.01 (m, 1H), 5.12-5.06 (m, 1H), 4.25 (s, 2H), 4.05 (ddd, 1H), 3.61-3.48 (m, 4H), 3.42-3.29 (m, 1H), 2.36-2.23 (m, 2H), 2.17-2.06 (m, 2H), 1.98-1.85 (m, 3H), 1.76-1.67 (m, 1H), 1.66-1.41 (m, 9H).

EXAMPLE 42

(R)-1-[2-(4-Cyano-benzyloxy)-ethyl]-3-(1-phenyl-cycloheptanecarbonyloxy)-1-azonia-bicyclo[2.2.2]octane bromide

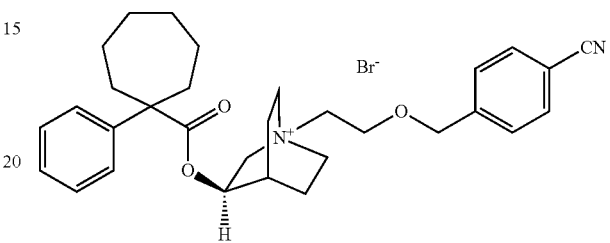

A mixture of 4-(2-bromo-ethoxymethyl)-benzonitrile (41 mg, 0.17 mmol) and 1-phenyl-cycloheptanecarboxylic acid (R)-(1-aza-bicyclo[2.2.2]oct-3-yl)ester (Example 14e) (51 mg) in MeCN (1 mL) was stirred at room temperature for 16 h then heated to 80° C. under nitrogen overnight. The resulting solid was filtered off, washed with ether and dried under vacuum to give the title compound (70 mg) as a white solid.
m/e 487 [M]⁺

¹H NMR (400 MHz, DMSO-D₆): δ 7.80 (dd, 2H), 7.48 (d, 2H), 7.31-7.22 (m, 4H), 7.22-7.16 (m, 1H), 5.06-4.96 (m, 1H), 4.57 (s, 2H), 3.94-3.78 (m, 3H), 3.56-3.35 (m, 5H), 3.27-3.18 (m, 1H), 3.11-3.00 (m, 1H), 2.36-2.18 (m, 2H), 2.08 (d, 2H), 1.98-1.77 (m, 3H), 1.72-1.60 (m, 1H), 1.60-1.38 (m, 9H).

EXAMPLE 43

(R)-3-(1-Phenyl-cycloheptanecarbonyloxy)-1-[(6-trifluoromethyl-pyridin-2-ylcarbamoyl)-methyl]-1-azonia-bicyclo[2.2.2]octane chloride a) 2-Chloro-N-(3-trifluoromethyl-phenyl)-acetamide

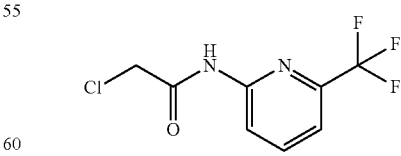

The sub-titled compound (1.1 g, quant., white solid) was prepared by a similar procedure to that used to prepare Example 14f using 2-amino-6-(trifluoromethyl)pyridine in place of 2-amino-pyridine and adding the chloroacetyl chloride at room temperature rather than at 0° C.

$^1$H NMR (300 MHz, CDCl$_3$): δ 8.90 (s, 1H), 8.42 (d, 1H), 4.22 (s, 2H).

EXAMPLE 43

(R)-3-(1-Phenyl-cycloheptanecarbonyloxy)-1-[(6-trifluoromethyl-pyridin-2-ylcarbamoyl)-methyl]-1-azonia-bicyclo[2.2.2]octane chloride

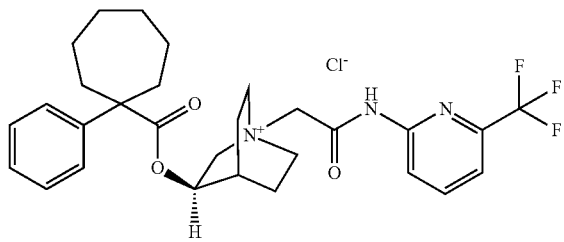

The title compound (66 mg, 76%, white solid) was prepared by a similar procedure to used to prepare Example 14 using 2-chloro-N-(3-trifluoromethyl-phenyl)-acetamide (Example 43a) in place of 2-chloro-N-pyridin-2-yl-acetamide.

m/e 530 [M]$^+$ $^1$H NMR (400 MHz, DMSO-D$_6$): δ 11.48 (s, 1H), 8.25 (d, 1H), 8.14 (t, 1H), 7.67 (d, 1H), 7.33-7.26 (m, 4H), 7.22-7.17 (m, 1H), 5.12-5.05 (m, 1H), 4.28 (s, 2H), 4.11-4.03 (m, 1H), 3.66-3.49 (m, 4H), 3.41-3.29 (m, 1H), 2.36-2.23 (m, 2H), 2.18-2.06 (m, 2H), 2.00-1.82 (m, 3H), 1.79-1.66 (m, 1H), 1.66-1.40 (m, 9H).

EXAMPLE 44

(R)-1-[(4-Methyl-pyridin-2-ylcarbamoyl)-methyl]-3-(1-phenyl-cycloheptanecarbonyloxy)-1-azonia-bicyclo[2.2.2]octane chloride a) 2-Chloro-N-(4-methyl-pyridin-2-yl)-acetamide

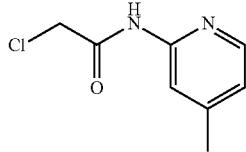

The sub-titled compound (1.3 g, 74%, solid) was prepared by a similar procedure to that used to prepare Example 14f using 2-amino-4-methylpyridine in place of 2-amino-pyridine and adding the chloroacetyl chloride at room temperature rather than at 0° C.

$^1$H NMR (400 MHz, CDCl$_3$): δ 8.77 (s, 1H), 8.17 (d, 1H), 8.03 (s, 1H), 6.93 (d, 1H), 4.19 (s, 2H), 2.39 (s, 3H).

EXAMPLE 44

(R)-1-[(4-Methyl-pyridin-2-ylcarbamoyl)-methyl]-3-(1-phenyl-cycloheptanecarbonyloxy)-1-azonia-bicyclo[2.2.2]octane chloride

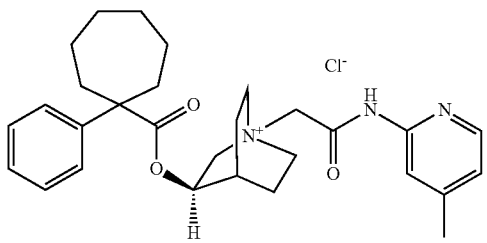

To a solution of 1-phenyl-cycloheptanecarboxylic acid (R)-(1-aza-bicyclo[2.2.2]oct-3yl) ester (Example 14e) (100 mg) in 1 mL MeCN was added 2-chloro-N-(4-methyl-pyridin-2-yl)-acetamide (Example 44a) (62 mg) and the mixture was stirred at room temperature for 21 h. The precipitate was filtered off and dried under vacuum at 50° C. to give the title compound (80 mg) as a white solid.

m/e 476 [M]$^+$ $^1$H NMR (400 MHz, DMSO-D$_6$): δ 10.98 (s, 1H), 8.18 (d, 1H), 7.85 (s, 1H), 7.33-7.26 (m, 4H), 7.22-7.17 (m, 1H), 7.02-7.00 (m, 1H), 5.11-5.04 (m, 1H), 4.24 (s, 2H), 4.10-4.02 (m, 1H), 3.64-3.50 (m, 4H), 3.40-3.29 (m, 1H), 2.42-2.20 (m, 5H), 2.17-2.06 (m, 2H), 1.98-1.84 (m, 3H), 1.79-1.67 (m, 1H), 1.73-1.31 (m, 9H).

EXAMPLE 45

(R)-1-[(5-Chloro-pyridin-2-ylcarbamoyl)-methyl]-3-(1-phenyl-cycloheptanecarbonyloxy)-1-azonia-bicyclo[2.2.2]octane chloride a) 2-Chloro-N-(5-chloro-pyridin-2-yl)-acetamide

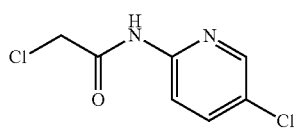

The sub-titled compound (0.33 g, 20%) was prepared by a similar procedure to that used to prepare Example 14f using 2-amino-5-chloropyridine in place of 2-amino-pyridine and adding the chloroacetyl chloride at room temperature rather than at 0° C.

$^1$H NMR (400 MHz, CDCl$_3$): δ 8.80 (s, 1H), 8.28 (d, 1H), 8.19 (d, 1H), 7.70 (dd, 1H), 4.20 (d, 2H).

EXAMPLE 45

(R)-1-[(5-Chloro-pyridin-2-ylcarbamoyl)-methyl]-3-(1-phenyl-cycloheptanecarbonyloxy)-1-azonia-bicyclo[2.2.2]octane chloride

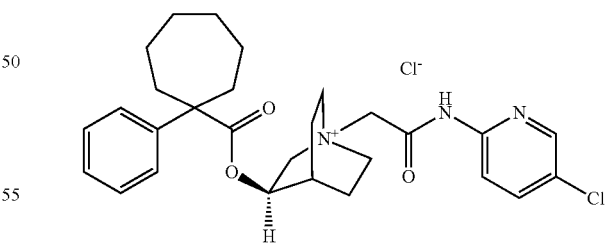

The title compound (103 mg, 63%, white solid) was prepared by a similar procedure to that used to prepare Example 44 using 2-chloro-N-(5-chloro-pyridin-2-yl)-acetamide (Example 45a) in place of 2-chloro-N-(4-methyl-pyridin-2-yl)-acetamide.

m/e 496 [M]$^+$ $^1$H NMR (400 MHz, DMSO-D$_6$): δ 11.26 (s, 1H), 8.41-8.39 (m, 1H), 8.02-7.94 (m, 2H), 7.32-7.25 (m, 4H), 7.22-7.17 (m, 1H), 5.12-5.03 (m, 1H), 4.27 (s, 2H), 4.09-4.02 (m,

1H), 3.63-3.50 (m, 4H), 3.42-3.32 (m, 1H), 2.37-2.23 (m, 2H), 2.17-2.05 (m, 2H), 1.99-1.84 (m, 3H), 1.78-1.65 (m, 1H), 1.65-1.39 (m, 9H).

EXAMPLE 46

(R)-3-(1-Phenyl-cycloheptanecarbonyloxy)-1-(p-tolylcarbamoyl-methyl)-1-azonia-bicyclo[2.2.2] octane bromide a) 2-Bromo-N-p-tolyl-acetamide

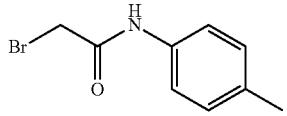

To a solution of p-toluidine (2.35 g) in 100 mL dichloromethane was added potassium carbonate (6.21 g). The reaction mixture was flushed with argon then bromoacetyl bromide (1.6 mL) was added dropwise and then the reaction mixture was stirred for 17 h. Water was added and the layers were separated. The organic layer was treated with cyclohexane and the volume was reduced in vacuo causing a solid to precipitate which was filtered off to afford the sub-titled compound (2.67 g) as an off-white solid.

$^1$H NMR (400 MHz, CDCl$_3$): δ 8.06 (s, 1H), 7.40 (d, 2H), 7.16 (d, 2H), 4.01 (s, 2H), 2.33 (s, 3H).

EXAMPLE 46

(R)-3-(1-Phenyl-cycloheptanecarbonyloxy)-1-(p-tolylcarbamoyl-methyl)-1-azonia-bicyclo[2.2.2] octane bromide

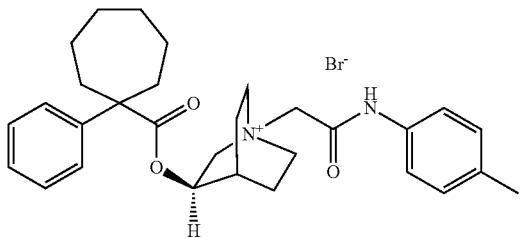

To 1-phenyl-cycloheptanecarboxylic acid (R)-(1-aza-bicyclo[2.2.2]oct-3-yl)ester (Example 14e) (51 mg) in acetonitrile (1 mL) was added 2-bromo-N-p-tolyl-acetamide (Example 46a) (39 mg). The reaction was stirred at room temperature overnight and the acetonitrile was removed under reduced pressure. The material was recrystallised from acetonitrile/ethyl acetate to afford the title compound as a colourless solid (16 mg).

m/e 475 [M]$^+$ $^1$H NMR (400 MHz, DMSO-D$_6$): δ 10.40 (s, 1H), 7.40 (d, 2H), 7.33-7.25 (m, 4H), 7.21-7.16 (m, 1H), 7.13 (d, 2H), 5.11-5.04 (m, 1H), 4.13 (q, 2H), 4.09-4.00 (m, 1H), 3.64-3.48 (m, 4H), 3.42-3.36 (m, 1H), 2.37-2.23 (m, 2H), 2.23 (s, 3H), 2.17-2.04 (m, 2H), 1.95-1.86 (m, 3H), 1.78-1.66 (m, 1H), 1.65-1.40 (m, 9H).

EXAMPLE 47

(R)-3-(1-Phenyl-cycloheptanecarbonyloxy)-1-(m-tolylcarbamoyl-methyl)-1-azonia-bicyclo[2.2.2] octane bromide a) 2-Bromo-N-m-tolyl-acetamide

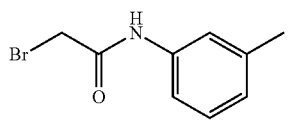

To a solution of m-toluidine (5.35 g) in 150 mL dichloromethane was added potassium carbonate (17.3 g). The reaction mixture was flushed with argon then bromoacetyl bromide (3.6 mL) was added dropwise over ~15 mins and the reaction mixture was stirred for 2.5 h. Water was added and the layers were separated. The organic layer was evaporated and the residue was treated with EtOAc/cyclohexane. The precipitate was filtered off and discarded. The mother liquors were evaporated and purified by silica gel chromatography eluting with 0-100% EtOAc/cyclohexane to give the sub-titled compound (6.13 g) as an off-white solid.

$^1$H NMR (400 MHz, CDCl$_3$): δ 8.06 (s, 1H), 7.38-7.28 (m, 2H), 7.27-7.21 (t, 1H), 6.98 (d, 1H), 4.02 (s, 2H), 2.36 (s, 3H).

EXAMPLE 47

(R)-3-(1-Phenyl-cycloheptanecarbonyloxy)-1-(m-tolylcarbamoyl-methyl)-1-azonia-bicyclo[2.2.2]octane bromide

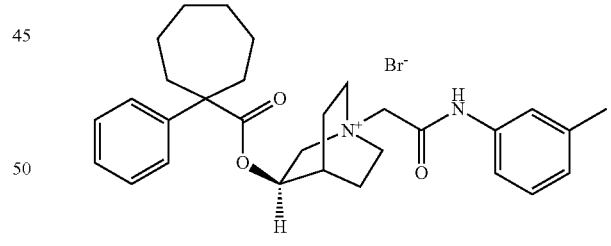

To 1-phenyl-cycloheptanecarboxylic acid (R)-(1-aza-bicyclo[2.2.2]oct-3-yl)ester (Example 14e) (50 mg) in acetonitrile (1 mL) was added 2-bromo-N-m-tolyl-acetamide (Example 47a) (38 mg). The reaction was stirred at room temperature for 26 hours and the acetonitrile was removed under reduced pressure. The material was purified by silica gel chromatography eluting with 0-10% MeOH/dichloromethane to afford the title compound (37 mg) as a colourless foam.

m/e 475 [M]$^+$ $^1$H NMR (400 MHz, DMSO-D$_6$): δ 10.40 (s, 1H), 7.39 (s, 1H), 7.32-7.25 (m, 5H), 7.22-7.15 (m, 2H), 6.92 (d, 1H), 5.11-5.05 (m, 1H), 4.14 (q, 2H), 4.11-4.01 (m, 1H), 3.64-3.48

(m, 4H), 3.42-3.30 (m, 1H), 2.39-2.21 (m, 5H), 2.18-2.05 (m, 2H), 1.97-1.84 (m, 3H), 1.77-1.66 (m, 1H), 1.65-1.39 (m, 9H).

EXAMPLE 48

(R)-1-(Oxazol-2-ylcarbamoylmethyl)-3-(1-phenyl-cycloheptanecarbonyloxy)-1-azonia-bicyclo[2.2.2]octane bromide a) 2-Bromo-N-oxazol-2-yl-acetamide

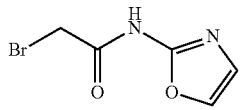

A solution of bromoacetyl bromide (0.44 mL) in dry CHCl$_3$ (5 mL) was added dropwise to a suspension of 2-amino-1,3-oxazole (0.39 g) and triethylamine (0.96 mL) in dry CHCl$_3$ (92 mL) at room temperature. The brown mixture was allowed to stir for 16 h, then quenched with H$_2$O (2 mL) and stirred for 20 mins before concentrating under reduced pressure to a light brown solid. The crude product was purified by silica gel chromatography eluting with 1-3% MeOH/dichloromethane to give the title compound (0.56 g) as an off-white solid.

$^1$H NMR (400 MHz, DMSO-D$_6$): δ 11.61 (s, 1H), 7.89 (s, 1H), 7.12 (s, 1H), 4.11 (s,2H).

EXAMPLE 48

(R)-1-(Oxazol-2-ylcarbamoylmethyl)-3-(1-phenyl-cycloheptanecarbonyloxy)-1-azonia-bicyclo[2.2.2]octane bromide

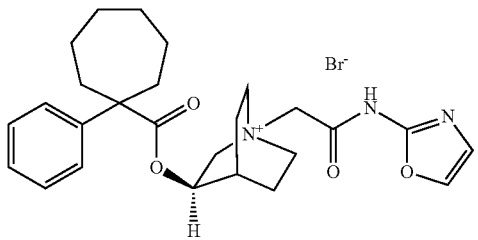

1-Phenyl-cycloheptanecarboxylic acid (R)-(1-aza-bicyclo[2.2.2]oct-3-yl)ester (Example 14e) (0.31 mmol) and 2-bromo-N-oxazol-2-yl-acetamide (Example 48a) (0.31 mmol) were stirred in anhydrous MeCN at room temperature for 18 hours. The reaction mixture was concentrated in vacuo and the yellow solid purified by flash silica gel column chromatography eluting with 0-15% MeOH/dichloromethane to give the title compound (100 mg) as a white solid.

m/e 452 [M]$^+$ $^1$H NMR (400 MHz, DMSO-D$_6$, 353K): δ 7.67 (s, 1H), 7.35-7.29 (m, 4H), 7.26-7.18 (m, 1H), 7.02 (s, 1H), 5.14-5.05 (m, 1H), 4.17-4.04 (m, 3H), 3.66-3.56 (m, 4H), 3.52-3.40 (m, 1H), 2.42-2.29 (m, 2H), 2.24-2.12 (m, 2H), 2.10-1.86 (m, 3H), 1.82-1.70 (m, 1H), 1.70-1.47 (m, 9H).

EXAMPLE 49

(R)-1-[(6-Methyl-pyridazin-3-ylcarbamoyl)-methyl]-3-(1-phenyl-cycloheptanecarbonyloxy)-1-azonia-bicyclo[2.2.2]octane bromide a) 2-Bromo-N-(6-methyl-pyridazin-3-yl)-acetamide

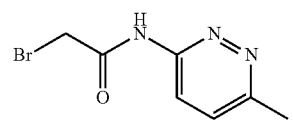

A solution of bromoacetyl bromide (0.22 mL) in dry CHCl$_3$ (4 mL) was added slowly to a suspension of 3-amino-6-methylpyridazine (0.24 g) and triethylamine (0.47 mL) in dry CHCl$_3$ (45 mL) at room temperature. The brown mixture was allowed to stir for 3.5 hr, then quenched with H$_2$O (1.5 mL) and stirred for 20 mins before concentrating under reduced pressure to a brown solid. The crude product was purified by silica gel chromatography eluting with 1-2% MeOH/dichloromethane. The relevant fractions were combined and evaporated to give the title compound (0.20 g) as a pinkish/beige solid.

$^1$H NMR (400 MHz, DMSO-D$_6$): δ 11.41 (s, 1H), 8.18 (d, 1H), 7.59 (d, 1H), 4.17 (s, 2H), 2.57 (s, 3H).

EXAMPLE 49

(R)-1-[(6-Methyl-pyridazin-3-ylcarbamoyl)-methyl]-3-(1-phenyl-cycloheptanecarbonyloxy)-1-azonia-bicyclo[2.2.2]octane bromide

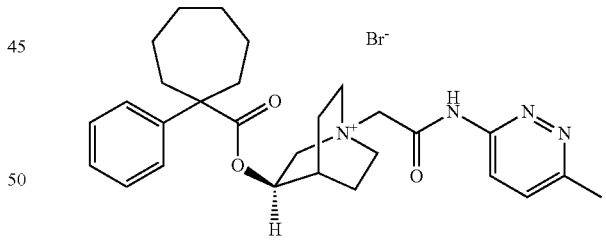

1-Phenyl-cycloheptanecarboxylic acid (R)-(1-aza-bicyclo[2.2.2]oct-3-yl)ester (Example 14e) (0.20 mmol) and 2-bromo-N-(6-methyl-pyridazin-3-yl)-acetamide (Example 49a (0.20 mmol) were stirred together in anhydrous MeCN at room temperature for 18 hours. The reaction mixture was concentrated in vacuo and the yellow solid purified by flash silica gel column chromatography eluting with 0-15% MeOH/dichloromethane to give the title compound (65 mg) as a tan solid.

m/e 477 [M]$^+$ $^1$H NMR (400 MHz, CDCl$_3$): δ 8.19 (d, 1H), 7.38 (d, 1H), 7.27 (d, 4H), 7.20-7.12 (m, 1H), 5.18-4.96 (m, 3H), 4.41 (dd, 1H), 4.11-3.95 (m, 3H), 3.81 (d, 1H), 3.47-3.37 (m, 1H), 2.66

(s, 3H), 2.45-2.27 (m, 2H), 2.26-2.13 (m, 2H), 2.08-1.96 (m, 3H), 1.81-1.68 (m, 1H), 1.69-1.30 (m, 9H).

EXAMPLE 50

(R)-3-(1-Phenyl-cycloheptanecarbonyloxy)-1-(pyrimidin-2-ylcarbamoylmethyl)-1-azonia-bicyclo[2.2.2]octane chloride a) 2-Chloro-N-pyrimidin-2-yl-acetamide

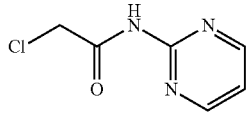

A solution of 2 amino-pyrimidine (2.0 g) in dry dichloromethane (17 mL) under nitrogen at 0° C. was treated with triethylamine (2.6 mL) followed by slow addition of chloroacetyl chloride (1.5 mL 18.4 mmol). The reaction mixture was allowed to warm up to room temperature. After 2h, the mixture was partitioned between dichioromethane and water. The phases were separated and the aqueous layer was extracted with dichloromethane (×2). The combined organic layers were washed with brine, dried over sodium sulphate, filtered and concentrated to give the crude product which was purified by silica gel chromatography eluting with 10% MeOH/dichloromethane. The relevant fractions were combined and evaporated to give the title compound (1.20 g) as a green solid.

$^1$H NMR (400 MHz, CDCl$_3$): δ 8.84 (s, 1H), 8.65 (d, 2H), 7.09 (t, 1H), 4.46 (s, 2H).

EXAMPLE 50

(R)-3-(1-Phenyl-cycloheptanecarbonyloxy)-1-(pyrimidin-2-ylcarbamoylmethyl)-1-azonia-bicyclo[2.2.2]octane chloride

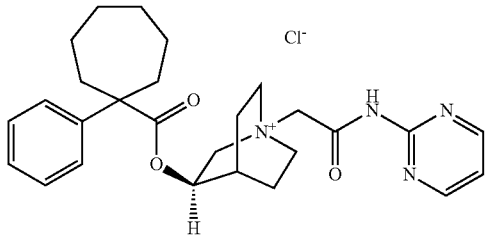

1-Phenyl-cycloheptanecarboxylic acid (R)-(1-aza-bicyclo[2.2.2]oct-3-yl) ester (Example 14e, 0.30 mmol) and 2-chloro-N-pyrimidin-2-yl-acetamide (Example 50a) (0.36 mmol) in MeCN (1.5 mL) were stirred together at room temperature overnight. The reaction mixture was concentrated in vacuo and the residue purified by silica gel chromatography eluting with 0-10% MeOH/dichloromethane to give the title compound as a white solid (90) mg).

m/e 463 [M]$^+$ $^1$H NMR (400 MHz, DMSO-D$_6$): δ 11.19 (s, 1H), 8.66 (d, 2H), 7.32-7.24 (m, 4H), 7.23-7.14 (m, 2H), 5.09-5.03 (m, 1H), 4.48 (s, 2H), 4.06 (ddd, 1H), 3.65-3.51 (m, 4H), 3.45-3.34 (m, 1H), 2.37-2.21 (m, 2H), 2.15-2.07 (m, 2H), 1.96-1.80 (m, 3H), 1.75-1.64 (m, 1H), 1.63-1.38 (m, 9H).

EXAMPLE 51

(R)-1-[(5-Cyano-pyridin-2-ylcarbamoyl)-methyl]-3-(1-phenyl-cycloheptanecarbonyloxy)-1-azonia-bicyclo[2.2.2]octane chloride a) 2-Chloro-N-(5-cyano-pyridin-2-yl)-acetamide

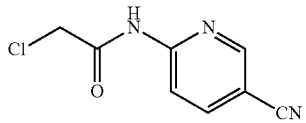

A solution of 2-amino-5-cyano pyridine (2.0 g) in dry dichloromethane (17 mL) under nitrogen at 0° C. was treated with triethylamine (2.6 mL) followed by slow addition of chloroacetyl chloride (1.5 mL). The reaction mixture was allowed to warm up to room temperature. After 2 h, the mixture was partitioned between dichloromethane and water. The phases were separated and the aqueous layer was extracted with dichloromethane (×2). The combined organic layer was washed with brine, dried over sodium sulphate, filtered and concentrated to give the crude product which was purified by silica gel chromatography eluting with 50% EtOAc/cyclohexane. The relevant fractions were combined and evaporated to give the title compound (2.17 g) as a light brown solid.

$^1$H NMR (400 MHz, CDCl$_3$): δ 8.99 (s, 1H), 8.61 (dd, 1H), 8.36 (dd, 1H), 8.00-7.97 (m, 1H), 4.23 (s, 2H).

EXAMPLE 51

(R)-1-[(5-Cyano-pyridin-2-ylcarbamoyl)-methyl]-3-(1-phenyl-cycloheptanecarbonyloxy)-1-azonia-bicyclo[2.2.2]octane chloride

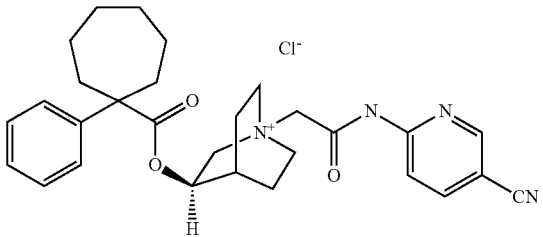

1-Phenyl-cycloheptanecarboxylic acid (R)-(1-aza-bicyclo[2.2.2]oct-3-yl) ester (Example 14e) (0.30 mmol) and 2-chloro-N-(5-cyano-pyridin-2-yl)-acetamide (Example 51a) (0.36 mmol) in MeCN (1.5 mL) were stirred together at room temperature overnight. The reaction mixture was concentrated in vacuo and the residue purified by silica gel chromatography eluting with 0-10% MeOH/dichloromethane to give the title compound as a white solid (60 mg).

m/e 487 [M]$^+$ $^1$H NMR (400 MHz, DMSO-D$_6$): δ 11.56 (s, 1H), 8.81 (dd, 1H), 8.31 (dd, 1H), 8.09 (d, 1H), 7.32-7.25 (m, 4H), 7.23-7.17 (m, 1H), 5.11-5.04 (m, 1H), 4.32 (s, 2H), 4.10-4.01 (m, 1H), 3.63-3.50 (m, 4H), 3.42-3.29 (m, 1H), 2.37-2.23 (m, 2H), 2.17-2.05 (m, 2H), 2.00-1.82 (m, 3H), 1.78-1.65 (m, 1H), 1.65-1.40 (m, 9H).

EXAMPLE 52

(R)-3-(1-Phenyl-cycloheptanecarbonyloxy)-1-(pyrimidin-5-ylcarbamoylmethyl)-1-azonia-bicyclo[2.2.2]octane chloride a) 2-Chloro-N-pyrimidin-5-yl-acetamide

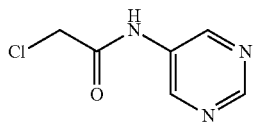

5-Aminopyrimidine (450 mg) was suspended in DCE (2 mL) and acetonitrile (2 mL) in a microwave vial. Chloroacetyl chloride (0.377 mL) was added with stirring. The vial was sealed and the reaction mixture was heated in the microwave at 80° C. for 5 minutes. The solid was filtered off, washed with acetonitrile (2×5 mL), DCE (2×5 mL) and pentane (2×30 mL) and then partioned between saturated sodium bicarbonate and DCE (50 mL/50 mL) ensuring the aqueous layer was still basic. The organic layer was separated and the aqueous layer was extracted with DCE (2×75 mL). The combined organic layer was dried over magnesium sulfate and evaporated to give the sub-titled compound (200 mg) as a yellow solid.

$^1$H NMR (400 MHz, DMSO-D$_6$): δ 10.71 (s, 1H), 9.00 (s, 2H), 8.93 (s, 1H), 4.35 (s, 2H).

EXAMPLE 52

(R)-3-(1-Phenyl-cycloheptanecarbonyloxy)-1-(pyrimidin-5-ylcarbamoylmethyl)-1-azonia-bicyclo[2.2.2]octane chloride

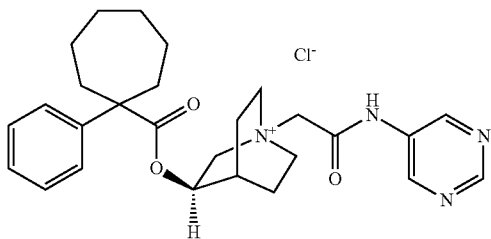

1-Phenyl-cycloheptanecarboxylic acid (R)-(1-aza-bicyclo[2.2.2]oct-3-yl)ester (Example 14e) (115 mg) in acetonitrile (2 mL) was treated with 2-chloro-N-pyrimidin-5-yl-acetamide (Example 52a) (66 mg) to give a dark brown solution that was stirred at room temperature overnight. The resulting solid was filtered off, washed with cold acetonitrile (2 mL) and pentane (3 mL) and dried under vacuum at 45° C. to give the title compound as a tan solid (151 mg).

m/e 463 [M]$^+$ $^1$H NMR (400 MHz, DMSO-D$_6$): δ 11.70 (s, 1H), 9.01 (s, 2H), 8.93 (s, 1H), 7.33-7.26 (m, 4H), 7.22-7.16 (m, 1H), 5.11-5.05 (m, 1H), 4.34 (s, 2H), 4.12-4.04 (m, 1H), 3.67-3.52 (m, 4H), 3.43-3.31 (m, 1H), 2.37-2.22 (m, 2H), 2.17-2.06 (m, 2H), 1.99-1.83 (m, 3H), 1.79-1.67 (m, 1H), 1.65-1.40 (m, 9H).

EXAMPLE 53

(R)-1-[(3-Fluoro-pyridin-2-ylcarbamoyl)-methyl]-3-(1-phenyl-cycloheptanecarbonyloxy)-1-azonia-bicyclo[2.2.2]octane chloride a) 2-Chloro-N-(3-fluoro-pyridin-2-yl)-acetamide

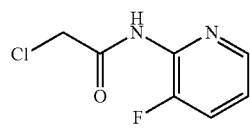

2-Amino-3-fluoropyridine (1.5 g) was dissolved in DCE (15 mL) and chloroacetylchloride (1.1 mL) was added dropwise. The reaction was heated in a microwave at 80° C. for 5 mins. The reaction mixture was cooled and the resulting solid was filtered off, washed with DCE, MeCN and pentane then suspended in dichloromethane and aqueous NaHCO$_3$ (sat) was added. The organic phase was separated and the aqueous layer was extracted with dichloromethane (×2). The combined organic layers were dried over sodium sulphate and concentrated. The crude product was purified by silica gel chromatography eluting with 0-100% EtOAc/cyclohexane to give the title compound as a white solid (800 mg).

$^1$H NMR (400 MHz, DMSO-D$_6$): δ 10.61 (s, 1H), 8.27 (dt, 1H), 7.83-7.77 (m, 1H), 7.41-7.35 (m, 1H), 4.37 (s, 2H).

EXAMPLE 53

(R)-1-[(3-Fluoro-pyridin-2-ylcarbamoyl)-methyl]-3-(1-phenyl-cycloheptanecarbonyloxy)-1-azonia-bicyclo[2.2.2]octane chloride

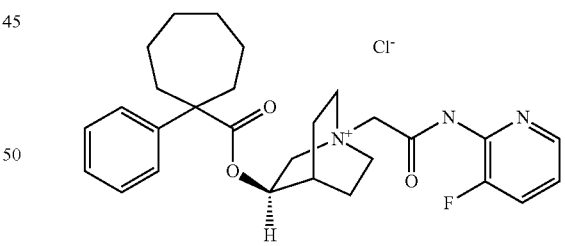

1-Phenyl-cycloheptanecarboxylic acid (R)-(1-aza-bicyclo[2.2.2]oct-3-yl) ester (Example 14e) (0.30 mmol) and 2-chloro-N-(3-fluoro-pyridin-2-yl)-acetamide (Example 53a) (0.36 mmol) in MeCN (1.5 mL) were stirred at room temperature overnight. The reaction mixture was concentrated in vacuo and the residue purified by silica gel chromatography eluting with 0-10% MeOH/dichloromethane to give the title compound as a white solid (86 mg).

m/e 480 [M]$^+$ $^1$H NMR (400 MHz, DMSO-D$_6$): δ 11.07 (s, 1H), 8.25 (dt, 1H), 7.81 (ddd, 1H), 7.39 (ddd, 1H), 7.31-7.24 (m, 4H), 7.22-7.15 (m, 1H), 5.11-5.04 (m, 1H), 4.36 (s, 2H), 4.11-4.04

(m, 1H), 3.66-3.52 (m, 4H), 3.44-3.32 (m, 1H), 2.37-2.21 (m, 2H), 2.19-2.06 (m, 2H), 1.99-1.82 (m, 3H), 1.77-1.65 (m, 1H), 1.65-1.38 (m, 9H).

EXAMPLE 54

(R)-1-[(3-Fluoro-pyridin-4-ylcarbamoyl)-methyl]-3-(1-phenyl-cycloheptanecarbonyloxy)-1-azonia-bicyclo[2.2.2]octane chloride a) 2-Chloro-N-(3-fluoro-pyridin-4-yl)-acetamide

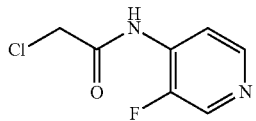

A solution of 3-fluoro-pyridin-4-ylamine (0.2 g) in dry dichloromethane (2 mL) under nitrogen at 0° C. was treated with triethylamine (0.28 mL) followed by slow addition of chloroacetyl chloride (0.16 mL). The reaction mixture was allowed to warm up to room temperature. After 2 h, the mixture was partitioned between dichloromethane and water The phases were separated and the aqueous layer was extracted with dichloromethane (×2). The combined organic layer was washed with brine, dried over sodium sulphate, filtered and concentrated to give the crude product which was purified by silica gel chromatography eluting with 0-100% EtOAc/cyclohexane. The relevant fractions were combined and evaporated to give the title compound (0.11 g) as a pink solid.

$^1$H NMR (400 MHz, DMSO-D$_6$): δ 10.55 (s, 1H), 8.56 (d, 1H), 8.35 (d, 1H), 8.16 (dd, 1H), 4.44 (s, 2H).

EXAMPLE 54

(R)-1-[(3-Fluoro-pyridin-4-ylcarbamoyl)-methyl]-3-(1-phenyl-cycloheptanecarbonyloxy)-1-azonia-bicyclo[2.2.2]octane chloride

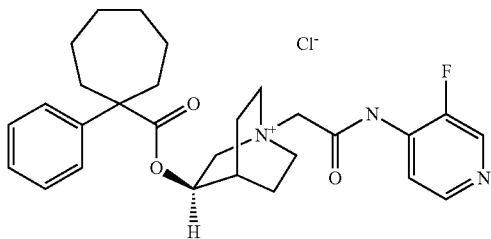

1-Phenyl-cycloheptanecarboxylic acid (R)-(1-aza-bicyclo[2.2.2]oct-3-yl) ester (Example 14e) (0.30 mmol) and 2-chloro-N-(3-fluoro-pyridin-4-yl)-acetamide (Example 54a) ( mmol) in MeCN (1.5 mL) were stirred together at room temperature overnight. The reaction mixture was concentrated in vacuo and the residue purified by silica gel chromatography eluting with 0-10% MeH/dichloromethane to give the title compound a white solid (110 mg).

$^1$H NMR (400 MHz, DMSO-D$_6$): δ 10.92 (s, 1H), 8.56 (d, 1H), 8.35 (d, 1H), 8.03 (dd, 1H), 7.32-7.26 (m, 4H), 7.21-7.16 (m, 1H), 5.11-5.05 (m, 1H), 4.41-4.29 (m, 2H), 4.10-4.02 (m, 1H), 3.63-3.50 (m, 4H), 3.42-3.30 (m, 1H), 2.36-2.23 (m, 2H), 2.17-2.06 (m, 2H), 1.98-1.82 (m, 3H), 1.78-1.65 (m, 1H), 1.66-1.40 (m, 9H).

EXAMPLE 55

(R)-3-(1-Phenyl-cycloheptanecarbonyloxy)-1-{2-[(pyrazine-2-carbonyl)-amino]-ethyl}-1-azonia-bicyclo[2.2.2]octane bromide a) Pyrazine-2-carboxylic acid (2-bromo-ethyl)-amide

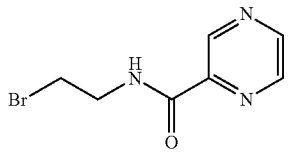

2-Pyrazine carboxylic acid (1 g) in dichloromethane (30 mL) was treated with triethylamine (1.27 mL) and HATU (3.6 g) and the mixture was stirred for 10 minutes. A solution of 2-bromoethylamine hydrobromide (1.5 g) and triethylamine (1.27 mL) in dichloromethane (20 mL) was added and the reaction mixture was stirred for 3 hours. Water (50 mL) was added and the organic layer was separated and washed with water (3×50 mL). The organic layer was dried over magnesium sulphate and evaporated to give the crude product which was purified by silica gel chromatography eluting with 0-100% EtOAc/dichloromethane. The relevant fractions were combined and evaporated to give a residue which was dissolved in EtOAc (40 mL) and washed with saturated sodium hydrogen carbonate ensuring the aqueous layer was basic. The organic layer was dried over magnesium sulfate and evaporated to give the sub-titled compound (1.0 g) as a white solid.

$^1$H NMR (400 MHz, DMSO-D$_6$): δ 9.21 (d, 1H), 9.14 (t, 1H), 8.90 (d, 1H), 8.75 (dd, 1H), 3.75-3.69 (m, 2H), 3.66-3.60 (m, 2H).

EXAMPLE 55

(R)-3-(1-Phenyl-cycloheptanecarbonyloxy)-1-{2-[(pyrazine-2-carbonyl)-amino]-ethyl}-1-azonia-bicyclo[2.2.2]octane bromide

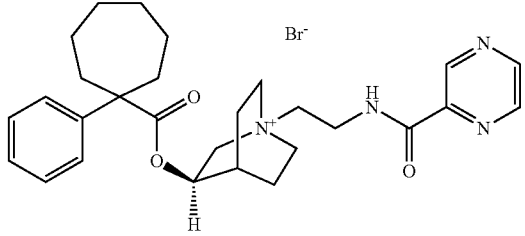

Pyrazine-2-carboxylic acid (2-bromo-ethyl)-amide (Example 55a) (87 mg) was added to a solution of 1-phenyl-cycloheptanecarboxylic acid (R)-(1-aza-bicyclo[2.2.2]oct-3-yl) ester (Example 14e) (113 mg) in acetonitrile (2 mL). The reaction mixture was allowed to stir at room temperature for 16 h. A solid precipitated out and was filtered off, washed with cold acetonitrile and dried under vacuum at 40° C. to give the title compound (96 mg) as a white solid.

m/e 477 [M]+

$^1$H NMR (400 MHz, DMSO-D$_6$): δ 9.22 (t, 1H), 9.17 (d, 1H), 8.88 (d, 1H), 8.72 (dd, 1H), 7.33-7.25 (m, 4H), 7.22-7.16 (m, 1H), 5.01-4.96 (m, 1H), 3.89 (ddd, 1H), 3.73-3.57 (m, 2H), 3.51-3.28 (m, 5H), 3.22 (dt, 1H), 3.13-3.02 (m, 1H), 2.38-2.30 (m, 1H), 2.30-2.20 (m, 1H), 2.17-2.06 (m, 2H), 1.97-1.76 (m, 3H), 1.69-1.37 (m, 10H).

EXAMPLE 56

(R)-3-(1-Phenyl-cycloheptanecarbonyloxy)-1-([1,2,4]thiadiazol-5-ylcarbamoylmethyl)-1-azonia-bicyclo[2.2.2]octane chloride a) 2-Chloro-N-[1,2,4]thiadiazol-5-yl-acetamide

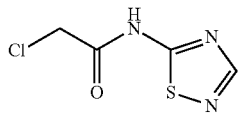

A solution of [1,2,4]-thiadiazol-5-ylamine (3.0 g) in dry dichloromethane (30 mL) under nitrogen at 0° C. was treated with triethylamine (4.6 mL) followed by slow addition of chloroacetyl chloride (2.6 mL). The reaction mixture was allowed to warm up to room temperature. After 2 h, the mixture was partitioned between dichloromethane and water. The phases were separated and the aqueous layer was extracted with dichloromethane (×2). The combined organic layer was washed with brine, dried over sodium sulphate, filtered and concentrated to give the crude product which was purified by silica gel chromatography eluting with 50-75% EtOAc/cyclohexane to give the title compound (1.00 g) as a yellow solid.

$^1$H NMR (400 MHz, DMSO-D$_6$): δ 13.32 (s, 1H), 8.51 (s, 1H), 4.52 (s, 2H).

EXAMPLE 56

(R)-3-(1-Phenyl-cycloheptanecarbonyloxy)-1-([1,2,4]thiadiazol-5-ylcarbamoylmethyl)-1-azonia-bicyclo[2.2.2]octane chloride

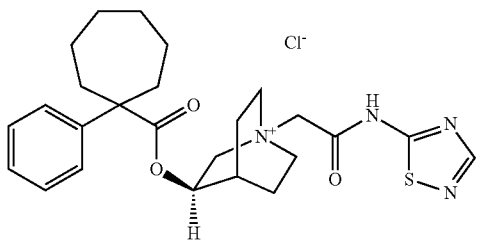

1-phenyl-cycloheptanecarboxylic acid (R)-(1-aza-bicyclo[2.2.2]oct-3-yl) ester (Example 14e) (0.30 mmol) and 2-chloro-N-[1,2,4]thiadiazol-5-yl-acetamide (0.36 mmol) (Example 56a) in MeCN (1.5 mL) were stirred at room temperature overnight. The reaction mixture was filtered and the solid obtained was washed with cold MeCN to give the title compound (30 mg) as a solid.

m/e 469 [M]+

$^1$H NMR (400 MHz, DMSO-D$_6$): δ 13.70 (s, 1H), 8.51 (s, 1H), 7.34-7.27 (m, 4H), 7.22-7.17 (m, 1H), 5.11-5.05 (m, 1H), 4.54-4.43 (m, 2H), 4.12-4.05 (m, 1H), 3.67-3.53 (m, 4H), 3.45-3.33 (m, 1H), 2.38-2.24 (m, 2H), 2.18-2.05 (m, 2H), 1.99-1.83 (m, 3H), 1.80-1.67 (m, 1H), 1.67-1.40 (m, 9H).

EXAMPLE 57

(R)-3-(1-Phenyl-cycloheptanecarbonyloxy)-1-{3-[(pyridine-2-carbonyl)-amino]-propyl}-1-azonia-bicyclo[2.2.2]octane bromide a) Methanesulfonic acid 3-[(pyridine-2-carbonyl)-amino]-propyl ester

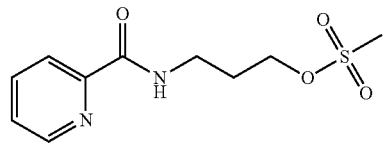

Isobutyl chloroformate (3.35 mL) was added to a solution of 2-pyridine carboxylic acid (2.10 g) and N-methyl morpholine (2.82 mL) in dry THF (85 mL) at 0° C. After 15 mins 3-amino-1-propanol (1.31 mL) was added and the mixture stirred overnight. The reaction mixture was concentrated to a pink solid in vacuo and was passed through a pad of silica (1-5% MeOH/dichloromethane). The resultant brown oil was taken up in dichloromethane (85 mL) and cooled to 0° C. To this solution was added Et$_3$N (4.75 mL) and methane sulfonylchloride (2.0 mL). After 30 mins the reaction was warmed to room temperature and stirred for 2.5 h before quenching with H$_2$O (50 mL). The layers were separated and the organic phase washed with sat. NaHCO$_3$ $_{(aq)}$ and dried (MgSO$_4$). Concentration under reduced pressure gave an orange oil which was purified by silica gel chromatography eluting with 90% EtOAc/cyclohexane to give the sub-titled compound (2.06 g) as an orange oil.

$^1$H NMR (400 MHz, CDCl$_3$): δ 8.55 (ddd, 1H), 8.29 (s, 1H), 8.17 (dt, 1H), 7.88-7.83 (m, 1H), 7.45 (ddd, 1H), 4.35 (t, 2H), 3.63 (q, 2H), 3.07 (s, 3H), 2.11 (p, 2H).

b) Pyridine-2-carboxylic acid (3-bromo-propyl)-amide

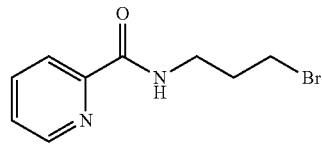

A mixture of methanesulfonic acid 3-[(pyridine-2-carbonyl)-amino]-propyl ester (Example 57a) (1.96 g) and lithium bromide (3.29 g) in acetone (19 mL) was heated to reflux for 2 h. The reaction mixture was cooled to room temperature, concentrated in vacuo and the residue partitioned between EtOAc/H$_2$O (60 mL, 1:1). The phases were separated and the aqueous phase further extracted with EtOAc (2×25 mL). The combined organics were dried (MgSO$_4$) and concentrated in vacuo to a brown oil which solidified on standing. Purification by silica gel chromatography eluting with 0-100% EtOAc/cyclohexane gives the sub-titled compound (1.5 g) as a white solid.

$^1$H NMR (400 MHz, CDCl$_3$): δ 8.55 (ddd, 1H), 8.25-8.12 (s, 1H), 8.19 (dt, 1H), 7.85 (td, 1H), 7.43 (ddd, 1H), 3.64 (q, 2H), 3.50 (t, 2H), 2.22 (p, 2H).

EXAMPLE 57

(R)-3-(1-Phenyl-cycloheptanecarbonyloxy)-1-{3-[(pyridine-2-carbonyl)-amino]-propyl}-1-azonia-bicyclo[2.2.2]octane bromide

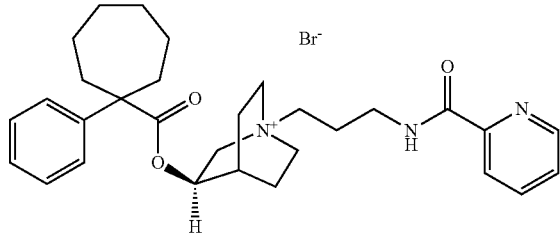

1-Phenyl-cycloheptanecarboxylic acid (R)-(1-aza-bicyclo[2.2.2]oct-3-yl)ester (Example 14e) (0.31 mmol) and pyridine-2-carbonyl acid (3-bromo-propyl)-amide (Example 57b) (0.31 mmol) were stirred together in anhydrous MeCN (3 mL) at room temperature for 16 days. The reaction mixture was concentrated in vacuo and the solid purified by silica gel chromatography eluting with 0-15% MeOH/dichloromethane to give the title compound (145 mg) as a white solid.

m/e 490 [M]$^+$ $^1$H NMR (400 MHz, DMSO-D$_6$): δ 8.94 (t, 1H), 8.62 (ddd, 1H), 8.03-7.95 (m, 2H), 7.58 (ddd, 1H), 7.31-7.24 (m, 4H), 7.19-7.13 (m, 1H), 5.01-4.95 (m, 1H), 3.76 (ddd, 1H), 3.51-3.09 (m, 7H), 3.09-3.01 (m, 1H), 2.93-2.82 (m, 1H), 2.36-2.22 (m, 2H), 2.14-2.06 (m, 2H), 1.99-1.90 (m, 1H), 1.92-1.71 (m, 4H), 1.68-1.39 (m, 10H).

EXAMPLE 58

(R)-1-[(2-Methyl-pyrimidin-4-ylcarbamoyl)-methyl]-3-(1-phenyl-cycloheptanecarbonyloxy)-1-azonia-bicyclo[2.2.2]octane chloride a) 2-Chloro-N-(2-methyl-pyrimidin-4-yl)-acetamide

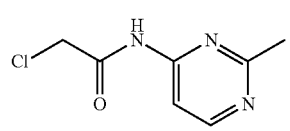

2-Methyl-pyrimidin-4-yl amine (545 mg) was suspended in DCE (5 mL) and chloroacetylchloride (0.4 mL) was added dropwise. The reaction was heated in a microwave at 80° C. for 5 mins. The reaction mixture was cooled to give a solid that was filtered, washed with dichloromethane then suspended in dichloromethane and sat. NaHCO$_3$ (aq) was added. The organic phase was collected and the aqueous layer extracted with dichloromethane (×2). The combined organic layer was dried over sodium sulphate and concentrated. The crude product was purified by silica gel chromatography eluting with 0-10% MeOH/dichloromethane to give the sub-titled compound as a yellow solid (70 mg, 7.5%).

$^1$H NMR (400 MHz, DMSO-D$_6$): δ 11.16 (s, 1H), 8.58 (d, 1H), 7.84 (d, 1H), 4.37 (s, 2H), 2.53 (s, 3H).

EXAMPLE 58

(R)-1-[(2-Methyl-pyrimidin-4-ylcarbamoyl)-methyl]-3-(1-phenyl-cycloheptanecarbonyloxy)-1-azonia-bicyclo[2.2.2]octane chloride

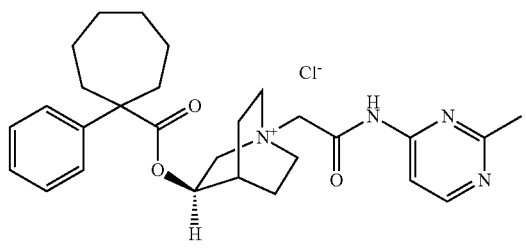

1-Phenyl-cycloheptanecarboxylic acid (R)-(1-aza-bicyclo[2.2.2]oct-3-yl)ester (Example 14e, 0.29 mmol) and 2-chloro-N-(2-methyl-pyrimidin-4-yl)-acetamide (Example 58a) (0.35 mmol) in MeCN (2.0 mL) were stirred together at room temperature for 16 h. The reaction mixture was concentrated in vacuo and the residue purified by silica gel chromatography eluting with 0-10% MeOH/dichloromethane to give the title compound as a white solid (55 mg).

m/e 477 [M]$^+$ $^1$H NMR (400 MHz, DMSO-D$_6$): δ 11.40 (s, 1H), 8.61 (d, 1H), 7.75 (d, 1H), 7.32-7.25 (m, 4H), 7.23-7.17 (m, 1H), 5.10-5.03 (m, 1H), 4.28 (s, 2H), 4.09-4.01 (m, 1H), 3.62-3.48 (m, 41-1), 3.40-3.30 (m, 1H), 2.50 (s, 3H), 2.36-2.24 (m, 2H), 2.17-2.05 (m, 2H), 1.98-1.84 (m, 3H), 1.78-1.65 (m, 1H), 1.64-1.41 (m, 9H).

EXAMPLE 59

(R)-1-[(6-Methyl-pyrimidin-4-ylcarbamoyl)-methyl]-3-(1-phenyl-cycloheptanecarbonyloxy)-1-azonia-bicyclo[2.2.2]octane chloride a) 2-Chloro-N-(6-methyl-pyrimidin-4-yl)-acetamide

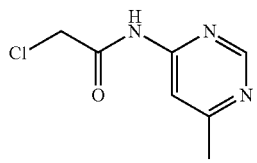

6-Methyl-pyrimidin-4-yl amine (545 mg) was suspended in DCE (5 mL) and chloroacetylchloride (0.4 mL) was added dropwise. The reaction was heated in a microwave at 80° C. for 5 mins. The reaction mixture was cooled, filtered and a solid obtained. The reaction was repeated a second time and both batches of solid were combined, washed with dichloromethane then suspended in dichloromethane and sat.

NaHCO$_3$ (aq.) was added. The organic phase was collected and the aqueous layer extracted with dichloromethane (×2). The combined organic layer was dried over sodium sulphate and concentrated. The crude product was purified by silica gel chromatography eluting with 0-10% MeOH/dichloromethane to give the sub-titled compound as a yellow solid (120 mg).

$^1$H NMR (400 MHz, DMSO-D$_6$): δ 11.11 (s, 1H), 8.76 (d, 1H), 7.91 (s, 1H), 4.38 (s, 2H), 2.44 (s, 3H).

EXAMPLE 59

(R)-1-[(6-Methyl-pyrimidin-4-ylcarbamoyl)-methyl]-3-(1-phenyl-cycloheptanecarbonyloxy)-1-azonia-bicyclo[2.2.2]octane chloride

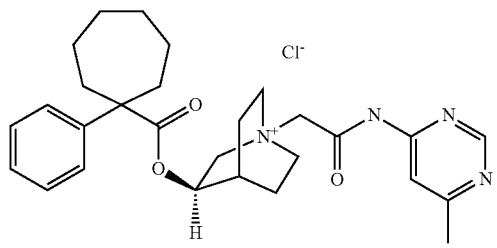

1-Phenyl-cycloheptanecarboxylic acid (R)-(1-aza-bicyclo[2.2.2]oct-3-yl)ester (Example 14e) (0.30 mmol) and 2-chloro-N-(6-methyl-pyrimidin-4-yl)-acetamide (Example 59a) (0.36 mmol) in MeCN (2. mL) were stirred together at room temperature for 16 h. The reaction mixture was concentrated in vacuo and the residue purified by silica gel chromatography eluting with 0-10% MeOH/dichloromethane to give the title compound as a white solid (125 mg).

m/e 477 [M]$^+$ $^1$H NMR (400 MHz, DMSO-D$_6$): δ 11.39 (s, 1H), 8.76 (d, 1H), 7.83 (s, 1H), 7.34-7.26 (m, 4H), 7.22-7.17 (m, 1H), 5.10-5.04 (m, 1H), 4.32 (s, 2H), 4.10-4.01 (m, 1H), 3.64-3.50 (m, 4H), 3.43-3.31 (m, 1H), 2.42 (s, 3H), 2.37-2.23 (m, 2H), 2.18-2.06 (m, 2H), 1.98-1.81 (m, 3H), 1.78-1.66 (m, 1H), 1.65-1.39 (m, 9H).

EXAMPLE 60

(R)-3-(1-Phenyl-cycloheptanecarbonyloxy)-1-{2-[(pyridine-2-carbonyl)-amino]-ethyl}-1-azonia-bicyclo[2.2.2]octane bromide a) Pyridine-2-carboxylic acid (2-bromo-ethyl)-amide

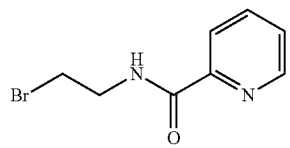

Picolinic acid (0.99 g) in dichloromethane (30 mL) was treated with triethylamine (1.27 mL) and HATU (3.6 g). The mixture was stirred for 10 minutes then a solution of 2-bromoethylamine hydrobromide (1.5 g) and triethylamine (1.27 mL) in dichloromethane (20 mL) was added. The reaction mixture was stirred for 3h. Water (50 mL) was added and the layers were separated. The organic layer was washed with water (3×50 mL), dried over magnesium sulphate and evaporated to afford the crude product which was purified by silica gel chromatography eluting with 0-100% EtOAc/dichloromethane. The relevant fractions were combined and evaporated, dissolved up in EtOAc (40 mL) and washed with saturated sodium hydrogen carbonate solution, ensuring the aqueous layer remained basic. The organic layer was dried over magnesium sulphate and evaporated to give the sub-titled compound (0.88 g) as a white solid.

$^1$H NMR (400 MHz, DMSO-D$_6$): δ 9.01 (t, 1H), 8.66 (ddd, 1H), 8.07-7.98 (m, 2H), 7.62 (ddd, 1H), 3.70 (q, 2H), 3.62 (t, 2H).

EXAMPLE 60

(R)-3-(1-Phenyl-cycloheptanecarbonyloxy)-1-{2-[(pyridine-2-carbonyl)-amino]-ethyl}-1-azonia-bicyclo[2.2.2]octane bromide

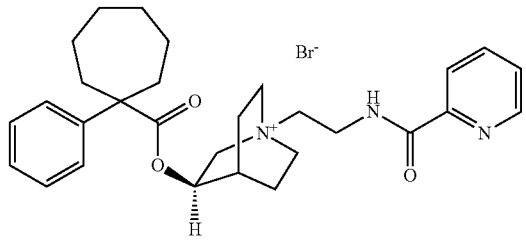

Pyridine-2-carboxylic acid (2-bromo-ethyl)-amide (Example 60a) (75 mg) was added to a solution of 1-phenyl-cycloheptanecarboxylic acid (R)-(1-aza-bicyclo[2.2.2]oct-3-yl)ester (Example 14e) (98 mg) in acetonitrile (2 mL). The reaction mixture was allowed to stir at room temperature for 16 h. A further 10 mg of pyridine-2-carboxylic acid (2-bromo-ethyl)-amide was added and the reaction mixture was stirred for 8 h. The volatiles were evaporated and the residue was purified by silica gel chromatography eluting with 0-10% MeOH/dichloromethane to give the title compound (55 mg) as a white solid.

m/e 476 [M]$^+$ $^1$H NMR (400 MHz, DMSO-D$_6$): δ 9.12 (t, 1H), 8.64-8.62 (m, 1H), 8.05-7.97 (m, 2H), 7.61 (ddd, 1H), 7.32-7.25 (m, 4H), 7.22-7.15 (m, 1H), 5.02-4.96 (m, 1H), 3.88 (ddd, 1H), 3.71-3.55 (m, 2H), 3.49-3.27 (m, 5H), 3.22 (dt, 1H), 3.12-3.02 (m, 1H), 2.38-2.20 (m, 2H), 2.17-2.07 (m, 2H), 1.96-1.75 (m, 3H), 1.69-1.38 (m, 10H).

EXAMPLE 61

(R)-3-(1-Phenyl-cycloheptanecarbonyloxy)-1-(3-pyridin-4-yl-propyl-1-azonia-bicyclo[2.2.2]octane bromide a) 4-(3-Bromo-propyl)-pyridine hydrobromide

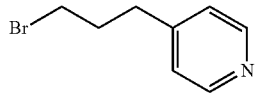

A solution of 3-pyridin-4-yl-propan-1-ol (2.88 mL) in hydrobromic acid (16 mL, 141.43 mmol) was heated at reflux at 135° C. for 18 h. The cooled solution was concentrated under vacuum and the residue was re-dissolved in isopropanol and re-concentrated (this process was repeated three more times). The residue was dissolved in isopropanol, decolouriseed by boiling with activated charcoal, filtered, and the clear solution left to crystallise in a freezer over 48 h. The resulting crystals were removed by filtration, washed with isopropanol/diethyl ether (1:1) followed by diethyl ether and then dried under vacuum at 40° C. and at room temperature to afford the sub-titled compound as a pale brown solid (3.55 g).

$^1$H NMR (400 MHz, D$_2$O): δ 8.64 (d, 2H), 7.96 (d, 2H), 3.52 (t, 2H), 3.12 (t, 2H), 2.30 (quint., 2H).

EXAMPLE 61

(R)-3-(1-Phenyl-cycloheptanecarbonyloxy)-1-(3-pyridin-4-yl-propyl)-1-azonia-bicyclo[2.2.2]octane bromide

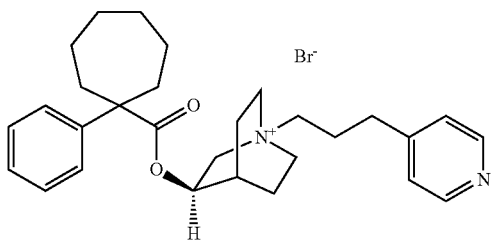

4-(3-Bromo-propyl)-pyridine hydrobromide (Example 61a) (0.210 g) was added to diethyl ether (10 mL) and sodium hydroxide solution (4 mL) (10%) in a separating funnel and the mixture shaken and separated. The ethereal layer was washed with water (2×10 mL), dried (MgSO$_4$) and evaporated to afford the free base as an oil. To the residue was added 1-phenyl-cycloheptanecarboxylic acid (R)-(1-aza-bicyclo [2.2.2]oct-3-yl) ester (Example 1e) (0.245 g) and acetonitrile (2 mL), and left to stand for 2 days. Addition of diethyl ether (20 mL) gave an oil, the supernatant was removed by decantation and the residue washed with ethyl acetate (2×20 mL). The oil was crystallised by stirring with diethyl ether (20 mL) and the solid washed twice with diethyl ether (2×20 mL) to afford the titled compound as a solid (0.094 g).

m/e 447 [M]$^+$ $^1$H NMR (400 MHz, DMSO-D$_6$): δ 8.51 (d, 2H), 7.35-7.30 (m, 4H), 7.30-7.27 (m, 2H), 7.24-7.18 (m, 1H), 5.07-5.01 (m, 1H), 3.81 (ddd, 1H), 3.43-3.27 (m, 2H), 3.21-3.14 (m, 1H), 3.10 (d, 1H), 2.97-2.88 (m, 2H), 2.59 (t, 2H), 2.40-2.27 (m, 3H), 2.18-2.10 (m, 2H), 2.04-1.76 (m, 5H), 1.72-1.43 (m, 10H).

Pharmacological Analysis

M3 Receptor Activity Assay

The affinity (pIC$_{50}$) of compounds to the M$_3$ receptor was determined by competition binding of [$^3$H]N-methyl scopolamine (NMS) to CHO-K1 (Chinese Hamster Ovary) cell membranes expressing the human muscarinic acetylcholine M$_3$ receptor (M$_3$-ACh) in a scintillation proximity assay (SPA) format.

SPA beads were precoated with membranes and then incubated at 2 mg of beads per well with serial dilutions of the compounds of the invention, [$^3$H]NMS at 0.2 nM, half Kd (experimentally determined dissociation constant) and assay buffer (20 mM HEPES pH 7.4 containing 5 mM MgCl$_2$). The assay was conducted in a final volume of 200 μL, in the presence of 1% (v/v) dimethyl sulphoxide (DMSO). Total binding of [$^3$H]NMS was determined in the absence of competing compound and non-specific binding of [$^3$H]NMS was determined in the presence of 1 μM atropine. The plates were incubated for 16 hours at room temperature and then read on Wallac Microbeta™ using a normalised $^3$H protocol The pIC$_{50}$, defined as the negative logarithm of the concentration of compound required for 50% reduction in specific [$^3$H]-NMS binding, was determined. Table 1 shows the pIC$_{50}$ figures for some representative Examples.

TABLE 1

| Compound of Example No. | pIC$_{50}$ |
| --- | --- |
| 1 | 9.1 |
| 5 | 9.4 |
| 13 | 10.1 |

Table 2 gives IC$_{50}$ strengths for the compounds of the examples.

TABLE 2

| Example No. | M3 binding IC$_{50}$ | Example No. | M3 binding IC$_{50}$ | Example No. | M3 binding IC$_{50}$ |
| --- | --- | --- | --- | --- | --- |
| 1 | +++ | 21 | +++ | 41 | ++ |
| 2 | +++ | 22 | +++ | 42 | ++ |
| 3 | ++ | 23 | +++ | 43 | ++ |
| 4 | +++ | 24 | +++ | 44 | ++ |
| 5 | +++ | 25 | +++ | 45 | +++ |
| 6 | +++ | 26 | +++ | 46 | ++ |
| 7 | ++ | 27 | ++ | 47 | ++ |
| 8 | +++ | 28 | ++ | 48 | ++ |
| 9 | +++ | 29 | ++ | 49 | +++ |
| 10 | +++ | 30 | +++ | 50 | +++ |
| 11 | +++ | 31 | ++ | 51 | ++ |
| 12 | +++ | 32 | ++ | 52 | +++ |
| 13 | +++ | 33 | ++ | 53 | ++ |
| 14 | +++ | 34 | ++ | 54 | +++ |
| 15 | +++ | 35 | ++ | 55 | ++ |
| 16 | +++ | 36 | ++ | 56 | ++ |
| 17 | +++ | 37 | +++ | 57 | ++ |
| 18 | +++ | 38 | +++ | 58 | +++ |
| 19 | +++ | 39 | ++ | 59 | ++ |
| 20 | +++ | 40 | +++ | 60 | +++ |
| 61 | +++ | | | | |

M3 Binding IC$_{50}$ < 2 nM "+++";
IC$_{50}$ 2-10 nM "++";
IC$_{50}$ > 10 nM "+";
NT—Not Tested.

Measurement of Plasma Protein Binding

The extent of plasma protein binding was determined via equilibrium dialysis of a compound between human plasma and aqueous buffer at 37° C. and determination of the concentration of compound in the plasma and buffer by HPLC-MS/MS.

Method

Dialysis cells (molecular weight cut-off 5000) were prepared by rinsing with water followed by soaking in the dialysis buffer for a minimum of 1 hour. The dialysis buffer was isotonic buffered saline pH 7.4. Stock solutions of compound in dimethylsulphoxide were prepared at a concentration of 0.5 mM. Frozen pooled Human plasma was obtained from volunteers.

The stock DMSO solution of a compound was added to the plasma at a ratio of 10 μl of DMSO to each ml of plasma. This gave a 1% DMSO in plasma solution with each compound at a concentration of 5 μM.

Dialysis cells were then prepared and one half of the cell filled with 750 μl of dialysis buffer and the other half of the cell with 750 μl of plasma solution of compound. Once prepared the cells were sealed and placed in an incubator box at 37° C. These cells were then rotated for a minimum of 4 hours to equilibrate.

After equilibration 500 μl of the buffer samples were removed and added to HPLC vials along with 100 μl of plasma (sample in 6-fold diluted plasma), and 100 μl of the plasma samples were removed and added to HPLC vials along with 500 μl of dialysis buffer (sample in 6-fold diluted plasma).

The samples were then analysed using HPLC-MS/MS. A four point calibration curve was obtained by dilutions of the stock solutions with 6-fold diluted plasma at concentrations of 0.013 μM, 0.05 μM, 0.25 μM and 1.25 μM which were injected in this order followed by the buffer sample and then the plasma sample.

Calculation

The concentration of compound in the samples were determined using MassLynx version 4.1 software (produced by Waters/Micromass) that automatically calculated a calibration curve and the concentration of compound in the cells. Plasma protein binding was determined from the calibration curve as the percentage of compound bound in human plasma (% bound) using the following equation;

$$\% \text{ bound} = 100 - 100 \left( \frac{\frac{\text{buffer peak area}}{\text{buffer injection volume}}}{5 \left( \frac{\text{plasma peak area}}{\text{plasma injection volume}} \right)} \right)$$

Table 3 shows the measured human plasma protein binding figure using the procedure described above for some representative Examples.

TABLE 3

| Compound of Example No. | % bound |
|---|---|
| 11 | 95.2 |
| 13 | 93.2 |
| 15 | 96.1 |
| 17 | 97.6 |
| 20 | 98.2 |
| 21 | 99.4 |

Methacholine Induced Bronchoconstriction in Vivo

Dunkin-Hartley guinea-pigs (300-600 g) were supplied by a designated breeding establishment. Animals were dosed with test compound or vehicle either by inhalation in conscious guinea-pigs or by intratracheal instillation (0.5 ml/kg) under recoverable gaseous anaesthesia (5% halothane). Animals were allowed to recover from the anaesthesia prior to the measurement of bronchoconstriction. Up to 48 hours post-dosing guinea-pigs were terminally anaesthetized with sodium pentobarbitone (60 mg/kg), the trachea cannulated for artificial ventilation and the jugular vein was cannulated for intravenous administration of methacholine. The guinea-pigs were ventilated using a constant volume respiratory pump (Harvard Rodent Ventilator model 683) at a rate of 60 breath/min and a tidal volume of 5 ml/kg during surgical preparation. Lung function (lung resistance and compliance) was measured in anaesthetised and ventilated guinea-pigs using a pulmonary measurement Flexivent system (SCIREQ, Montreal, Canada) connected to the tracheal cannulae. The animals were ventilated (quasi-sinusoidal ventilation pattern) at 60 breaths/min at a tidal volume of 5 ml/kg. A positive end expiratory pressure of 2-3 $cmH_2O$ was applied. Respiratory resistance was measured using the Flexivent "snapshot" facility (1 second duration, 1 Hz frequency). Lung resistance and compliance was measured before and after intravenous administration of methacholine (3, 10 and 30 ug/kg). The peak increase in resistance following methacholine challenge was calculated and the effect of the test compound on methacholine-induced lung function changes was calculated. Percentage inhibition of bronchoconstriction was calculated at each dose of methacholine as follows:

$$\frac{[\text{Change in resistance in vehicle treated group} - \text{Change in resistance in compound treated group}]}{[\text{Change in resistance in vehicle treated group}]} \times 100$$

Inhibition of Pilocarpine Induced Salivation by i.n. Administered Compounds.

Guinea pigs (450-550 g) supplied by Harlan U K or David Hall, Staffs U K and acclimatised to the in-house facilities for a minimum of three days before use. Guinea pigs were randomly assigned into treatment groups and weighed. Each animal was lightly anaesthetised (4% Halothane) and administered compound or vehicle intranasally (0.5 ml/kg) at up to 24 hours before challenge with pilocarpine. At the test time point, guinea pigs were terminally anaesthetised with urethane (25% solution in H20, 1.5 g/kg). Once sufficient anaesthesia had developed (absence of toe pinch reflex) each animal had an absorbent pad placed in the mouth for 5 minutes to dry residual saliva, this pad was removed and replaced with a new pre-weighed pad for 5 minutes to establish a reading of baseline saliva production. At the end of this 5 minute period the pad was removed and weighed. A new pre-weighed pad was inserted into the mouth before each animal received s.c. pilocarpine administered under the skin at the back of the neck (0.6 mg/kg @ 2 ml/kg). The pad was removed, weighed and replaced with a new pre-weighed pad every 5 minutes up to 15 minutes.

Saliva production was calculated by subtracting the pre-weighed weight of the pad from each 5 minute period post weighed pad and these numbers added together to produce an accumulation of saliva over 15 minutes. Each 5 minute period could be analysed in addition to the whole 15 minute recording period. Baseline production of saliva was assumed to be constant and multiplied by three to produce a reading for baseline saliva production over 15 minutes.

Inhibition of saliva produced by the compound could be calculated by using the following equation:

(1−(Test-baseline)/(*Veh*-baseline))*100.

The invention claimed is:
1. A compound having the following formula:

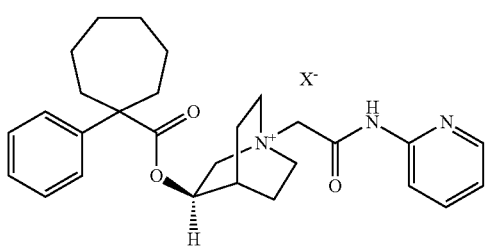

wherein X is a pharmaceutically acceptable anion of a mono- or polyvalent acid.

2. The compound according to claim 1, wherein X⁻ is selected from the group consisting of chloride, bromide, and formate.

3. A pharmaceutical composition comprising the compound according to claim 1, in association with a pharmaceutically acceptable adjuvant, diluents or carrier.

4. A process for the preparation of a pharmaceutical composition, which comprises mixing the compound according to claim 1 with a pharmaceutically acceptable adjuvant, diluents or carrier.

5. A compound having the following formula:

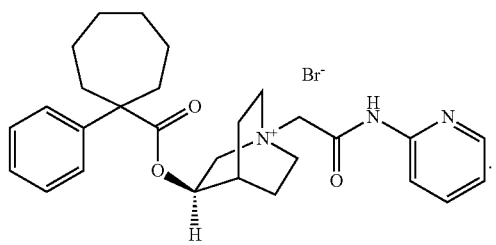

6. A pharmaceutical composition comprising the compound according to claim 5, in association with a pharmaceutically acceptable adjuvant, diluent or carrier.

7. A process for the preparation of a pharmaceutical composition, which comprises mixing the compound according to claim 5 with a pharmaceutically acceptable adjuvant, diluent or carrier.

* * * * *